US012600738B2

(12) United States Patent
Hong et al.

(10) Patent No.: US 12,600,738 B2
(45) Date of Patent: Apr. 14, 2026

(54) QUINOLINONE DERIVATIVE COMPOUND SELECTIVELY BINDING TO CYSTEINE, PEPTIDE CONJUGATE THEREOF, AND ANTIBODY-DRUG CONJUGATE COMPRISING SAME

(71) Applicants: INSTITUTE FOR BASIC SCIENCE, Daejeon (KR); KOREA ADVANCED INSTITUTE OF SCIENCE AND TECHNOLOGY, Daejeon (KR)

(72) Inventors: Sungwoo Hong, Daejeon (KR); Jaebong Jang, Daejeon (KR); Hangyeol Choi, Daejeon (KR); Myojeong Kim, Daejeon (KR)

(73) Assignees: INSTITUTE FOR BASIC SCIENCE;, Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 495 days.

(21) Appl. No.: 18/023,920

(22) PCT Filed: Aug. 25, 2021

(86) PCT No.: PCT/KR2021/011382
§ 371 (c)(1),
(2) Date: Feb. 28, 2023

(87) PCT Pub. No.: WO2022/045773
PCT Pub. Date: Mar. 3, 2022

(65) Prior Publication Data

US 2023/0322821 A1 Oct. 12, 2023

(30) Foreign Application Priority Data

Aug. 28, 2020 (KR) ........................ 10-2020-0109479

(51) Int. Cl.
*C07F 9/30* (2006.01)
*A61K 47/68* (2017.01)

(52) U.S. Cl.
CPC .......... *C07F 9/304* (2013.01); *A61K 47/6889* (2017.08)

(58) Field of Classification Search
None
See application file for complete search history.

(56) References Cited

U.S. PATENT DOCUMENTS 4,124,588 A * 11/1978 Hardtmann ............... C07F 9/60 987/95

FOREIGN PATENT DOCUMENTS

EP 0640612 A1 * 3/1995 ............. A61P 43/00
KR 10-2016-0031552 A 3/2016

OTHER PUBLICATIONS

Pieta et al. Novel synthesis and cytotoxic activity of 1,4-disubstituted 3-methylidene-3,4-dihydroquinolin-2(1H)-ones. RSC Advances (2015), vol. 5, No. 95, pp. 78324-78335. (Year: 2015).*

(Continued)

*Primary Examiner* — Jeffrey S Lundgren
*Assistant Examiner* — Sara Elizabeth Townsley
(74) *Attorney, Agent, or Firm* — Hauptman Ham, LLP

(57) ABSTRACT

The present disclosure relates to a quinolinone derivative compound selectively binding to cysteine, an amino acid- or peptide-conjugate thereof, and an antibody-drug conjugate comprising same. Since a conjugate with high chemoselectivity and high yield is formed through a radical pathway induced by visible light, the present disclosure can be applied in various ways to bioconjugation.

17 Claims, 7 Drawing Sheets

(56) References Cited

OTHER PUBLICATIONS

Kim et al. Visible-Light-Induced Pyridylation of Remote C(sp3)-H Bonds by Radical Translocation of N-Alkoxypyridinium Salts. Angew. Chem. Int. Ed. 57, 15517-15522 (2018). (Year: 2018).*

Inwon Kim et al., "Direct Phosphonation of Quinolinones and Coumarins Driven by the Photochemical Activity of Substrates and Products", Organic Letters, 2017, vol. 19, No. 6, 5 pages, cited in the Specification and NPL No. 6.

Inwon Kim et al., "Visible-Light-Induced Pyridylation of Remote C(sp3)-H Bonds by Radical Translocation of N-Alkoxypyridinium Salts", Angewandte Chemie International Edition, 2018, vol. 57, No. 47, pp. 15517-15522, cited in the Specification and NPL No. 6.

Yu-Long Zhao et al., "[NiCI2(dppp)]-Catalyzed Cross-Coupling of Aryl Halides with Dialkyl Phosphite, Diphenylphosphine Oxide, and Diphenylphosphine", Chemistry—A European Journal, 2012, vol. 18, No. 31, pp. 9622-9627, cited in NPL No. 6.

Honglin Zhang et al, "Silver-catalyzed cascade radical cyclization: direct approach to 3,4-disubstituted dihydroquinolin-2(1H)-ones through activation of P—H bond and functionalization of C(sp2)-H bond", The Journal of organic chemistry, 2016, vol. 81, No. 5, 16 pages, cited in NPL No. 6.

Hangyeol Choi et al., "Visible-Light-Induced Cysteine-Specific Bioconjugation: Biocompatible Thiol-Ene Click Chemistry", Angewandte Chemie International Edition, Aug. 31, 2020, vol. 59, No. 50, 10 pages, cited in NPL No. 6.

International Search Report issued Dec. 6, 2021, corresponding to International Application No. PCT/KR20201/011382, 6 pages.

* cited by examiner

6m, 81% (60%)

6n, 68% (58%)

6o, 67% (65%)

6p, 75% (60%)

6q, 68% (54%)

6r, 77% (57%)

6s, 80% (75%)[a]

6t, 68% (55%)

6u, 70% (67%)
*from* *Insulin β fragment (17-24)*

6v, 62% (52%)[a]
*from* *Src fragment*

[a] Conjugation of free-cysteine-containing polypeptides

12b, BSA-$\mathbf{Q}_{PEG}$

[b] $Q_{CAT}$ (10 mol%) was used.
[c] NaOAc buffer (pH 3.5) was used instead of phosphate buffer.

12c, BSA-biotin

QUINOLINONE DERIVATIVE COMPOUND SELECTIVELY BINDING TO CYSTEINE, PEPTIDE CONJUGATE THEREOF, AND ANTIBODY-DRUG CONJUGATE COMPRISING SAME

CROSS-REFERENCE TO RELATED APPLICATION

The present application is a national stage filing under 35 U.S.C § 371 of PCT application number PCT/KR2021/011382 filed on Aug. 25, 2021 which is based upon and claims the benefit of priorities to Korean Patent Application No. 10-2020-0109479 filed on Aug. 28, 2020 in the Korean Intellectual Property Office. All of the aforementioned applications are hereby incorporated by reference in their entireties.

TECHNICAL FIELD

The present disclosure relates to a quinolinone derivative compound which selectively binds to cysteine, a peptide conjugate thereof, and an antibody-drug conjugate including the same.

BACKGROUND ART

Bioconjugation induced by visible light is in the spotlight in that it is environmentally sustainable and may be performed under mild reaction conditions. It may be used in a strategy to produce a reactive radical species from visible light to functionalize biomolecules.

However, a base or an oxidizing agent should be added to a visible-light-induced photocatalytic reaction, which causes a problem of being incompatible with characteristics of proteins and resistance of amino acid residues. In addition, since there is a problem in that the solubility of a reagent and a photocatalyst in an aqueous solution is low, many photochemical methods which were developed for conjugation of a biomolecular material still have limitations in acting only in an organic medium. Therefore, a study on a photocatalyst which has excellent activity in an aqueous solution and may show activity without the need for an additive such as various oxidizing agents is demanded.

Traditionally, bioconjugation depends on a cysteine (Cys) amino acid having very high reactivity. Cysteine is one of two amino acids containing sulfur, and since, unlike methionine (Met), it is easily modified using acid-base chemistry, it has been used as a means for attaching a tag or a chemical functional group.

In particular, a strategy to use excellent nucleophilicity of a thiol (—SH) group to proceed with a thiol-Michael addition in maleimide was used. However, there are problems of poor chemical selectivity in the presence of a nucleophilic amino acid and the progress of a retro-Michael reaction due to the instability of a thiosuccinimide ring. The retro-Michael reaction as such may cause the release of a drug (payload) in a non-target area when the cysteine bioconjugation is used as an antibody-drug conjugate, and thus, a very dangerous side effect can be shown.

RELATED ART (Non-patent document 1) Kim, I.; Min, M.; Kang, D.; Kim, K.; Hong, S. Org. Lett. 2017, 19, 1394.

(Non-patent document 2) Kim et al., Angew. Chem. Int. Ed, 2018, 57, 15517-15522

DISCLOSURE

Technical Problem

In order to improve the stability of the protein conjugate, the present inventors formed a C—S bond by a thiol-ene reaction using a radical reaction, and studied a photocatalyst for cysteine selective bioconjugation, thereby contriving the present disclosure.

An object of the present disclosure is to provide a quinolinone derivative compound for deriving cysteine-selective bioconjugation under mild conditions, without a use of a metal, an oxidizing agent, or an external photocatalyst.

Another object of the present disclosure is to provide a photocatalyst having excellent water compatibility, which does not compete with other nucleophilic residues through a radical reaction using visible light to provide an effect of preventing by-product production in vivo.

Another object of the present disclosure is to provide effective high selectivity in a powerful and rapid cysteine conjugation reaction by selectively producing a radical in a cysteine residue.

Still another object of the present disclosure is to provide excellent utilization as an antibody-drug conjugate due to high selectivity to cysteine.

Technical Solution

In one general aspect, a quinolinone derivative compound which selectively binds to cysteine represented by the following Chemical Formula 1 is provided:

[Chemical Formula 1]

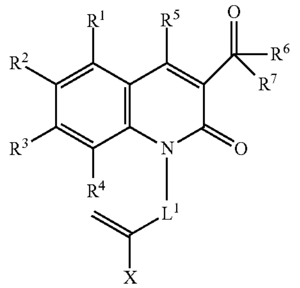

wherein $R^1$ to $R^5$ are independently of one another hydrogen, C1-C20 alkyl, C3-C20 cycloalkyl, C3-C20 heterocycloalkyl, C1-C20 alkoxy, C6-C20 aryl, or C3-C20 heteroaryl;

$R^6$ and $R^7$ are independently of each other hydrogen, C1-C20 alkyl, C1-C20 alkoxy, C6-C20 aryl, or C3-C20 heterocycloalkyl;

$L^1$ is C4-C20 alkylene or C1-C20 oxyalkylene;

X is hydrogen, halogen, C1-C10 alkyl, C1-C7 haloalkyl, C1-C10 alkoxy, C1-C10 haloalkoxyl, or C6-C20 aryl;

the heteroaryl and the heterocycloalkyl independently of each other contain one or more heteroatoms selected from nitrogen, oxygen, and sulfur; and alkyl, cycloalkyl, heterocycloalkyl, alkoxy, aryl, and heteroaryl of $R^1$ to $R^5$ may be further substituted by —OH, —OR', —COR', —NR'R", —NR'COR", —NHCOR', —$NHCOCH_2NR'R"$, and —NR'PO(OR")(OH).

In an exemplary embodiment of the present disclosure, in the quinolinone derivative compound which selectively binds to cysteine represented by Chemical Formula 1, $R^1$ to $R^5$ may be independently of one another hydrogen, C1-C7 alkyl, C3-C10 cycloalkyl, C3-C10 heterocycloalkyl, C1-C7 alkoxy, C6-C10 aryl, or C3-C10 heteroaryl;

$R^6$ and $R^7$ may be independently of each other hydrogen, C1-C7 alkyl, C1-C7 alkoxy, C6-C10 aryl, or C3-C10 heterocycloalkyl;

$L^1$ may be C4-C10 alkylene or C1-C20 oxyalkylene;

X may be hydrogen, halogen, C1-C7 alkyl, C1-C7 haloalkyl, C1-C7 alkoxy, C1-C7 haloalkoxy, or C6-C10 aryl;

the heteroaryl and the heterocycloalkyl may independently of each other contain one or more heteroatoms selected from nitrogen, oxygen, and sulfur; and alkyl, cycloalkyl, heterocycloalkyl, alkoxy, aryl, and heteroaryl of $R^1$ to $R^5$ may be further substituted by —OH, —OR', —COR', —NR'R", —NR'COR", —NHCOR', —$NHCOCH_2NR'R"$, and —NR'PO(OR")(OH).

In an exemplary embodiment of the present disclosure, $R^1$ to $R^5$ may be independently of one another hydrogen, C1-C7 alkyl, C1-C7 alkoxy, C6-C10 aryl, or C3-C10 heteroaryl;

$R^6$ and $R^7$ may be independently of each other hydrogen, C1-C7 alkyl, C1-C7 alkoxy, or C6-C10 aryl;

$L^1$ may be C4-C10 alkylene or include 1 to 10—$OCH_2CH_2$-units;

X may be hydrogen, halogen, C1-C7 alkyl, C1-C7 haloalkyl, C1-C7 alkoxy, or C1-C7 haloalkoxy;

the heteroaryl may independently of each other contain one or more heteroatoms selected from nitrogen, oxygen, and sulfur; and alkyl, alkoxy, aryl, and heteroaryl of $R^1$ to $R^5$ may be further substituted by —OH, —OR', —COR', —NR'R", —NR'COR", —NHCOR', —$NHCOCH_2NR'R"$, and —NR'PO(OR")(OH).

In an exemplary embodiment of the present disclosure, $R^1$ to $R^5$ may be independently of one another hydrogen, C1-C7 alkyl, or C1-C7 alkoxy;

$R^6$ and $R^7$ may be independently of each other C1-C7 alkoxy or C6-C10 aryl;

$L^1$ may be C4-C10 alkylene or include 1 to 10—$OCH_2CH_2$-units;

X may be hydrogen, halogen, C1-C7 alkyl, or C1-C7 haloalkyl; and alkyl, alkoxy, or aryl of $R^1$ to $R^5$ may be further substituted by —OH, —OR', —COR', —NR'R", —NR'COR", —NHCOR', —$NHCOCH_2NR'R"$, and —NR'PO(OR")(OH).

In another general aspect, an amino acid- or peptide conjugate represented by the following Chemical Formula 2 is provided:

[Chemical Formula 2]

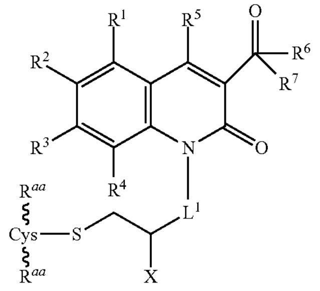

wherein

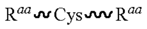

is a single amino acid, oligopeptide, polypeptide, or protein including cysteine or a pseudo-cysteine residue;

$R^1$ to $R^5$ are independently of one another hydrogen, C1-C20 alkyl, C3-C20 cycloalkyl, C3-C20 heterocycloalkyl, C1-C20 alkoxy, C6-C20 aryl, or C3-C20 heteroaryl;

$R^6$ and $R^7$ are independently of each other hydrogen, C1-C20 alkyl, C1-C20 alkoxy, C6-C20 aryl, or C3-C20 heterocycloalkyl;

$L^1$ is C4-C20 alkylene or C1-C20 oxyalkylene;

X is hydrogen, halogen, C1-C10 alkyl, C1-C7 haloalkyl, C1-C10 alkoxy, C1-C10 haloalkoxyl, or C6-C20 aryl;

the heteroaryl and the heterocycloalkyl independently of each other contain one or more heteroatoms selected from nitrogen, oxygen, and sulfur;

alkyl, cycloalkyl, heterocycloalkyl, alkoxy, aryl, and heteroaryl of $R^1$ to $R^5$ may be further substituted by any one or more selected from the group consisting of —OR', —COR', —NR'R", —NR'COR", —NHCOR', —$NHCOCH_2NR'R"$, and NR'PO(OR")(OH); and R' and R" are independently of each other any one selected from the group consisting of hydrogen, C1-C7 alkyl, C3-C6 cycloalkyl, C3-C6 alkenyl, and C3-C6 alkynyl.

In an exemplary embodiment of the present disclosure,

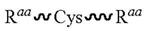

may be a single amino acid, oligopeptide, polypeptide, or protein including cysteine or a pseudo-cysteine residue;

$R^1$ to $R^5$ may be independently of one another hydrogen, C1-C7 alkyl, C3-C10 cycloalkyl, C3-C10 heterocycloalkyl, C1-C7 alkoxy, C6-C10 aryl, or C3-C10 heteroaryl;

$R^6$ and $R^7$ may be independently of each other hydrogen, C1-C7 alkyl, C1-C7 alkoxy, C6-C10 aryl, or C3-C10 heterocycloalkyl;

$L^1$ may be C4-C10 alkylene or C1-C20 oxyalkylene;

X may be hydrogen, halogen, C1-C7 alkyl, C1-C7 haloalkyl, C1-C7 alkoxy, C1-C7 haloalkoxy, or C6-C10 aryl;

the heteroaryl and the heterocycloalkyl may independently of each other contain one or more heteroatoms selected from nitrogen, oxygen, and sulfur; and alkyl, cycloalkyl, heterocycloalkyl, alkoxy, aryl, and heteroaryl of $R^1$ to $R^5$ may be further substituted by —OH, —OR', —COR', —NR' R", —NR' COR", —NHCOR', —$NHCOCH_2NR'R"$, and —NR'PO(OR")(OH).

In an exemplary embodiment of the present disclosure,

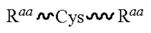

may be a single amino acid, oligopeptide, polypeptide, or protein cysteine or a pseudo-cysteine residue;

$R^1$ to $R^5$ may be independently of one another hydrogen, C1-C7 alkyl, C1-C7 alkoxy, C6-C10 aryl, or C3-C10 heteroaryl;

$R^6$ and $R^7$ may be independently of each other hydrogen, C1-C7 alkyl, C1-C7 alkoxy, or C6-C10 aryl;

$L^1$ may be C4-C10 alkylene or include 1 to 10—$OCH_2CH_2$-units;

X may be hydrogen, halogen, C1-C7 alkyl, C1-C7 haloalkyl, C1-C7 alkoxy, or C1-C7 haloalkoxy;

the heteroaryl may independently of each other contain one or more heteroatoms selected from nitrogen, oxygen, and sulfur; and alkyl, alkoxy, aryl, and heteroaryl of $R^1$ to $R^5$ may be further substituted by —OH, —OR', —COR', —NR'R", —NR'COR", —NHCOR', —$NHCOCH_2NR'R"$, and —NR'PO(OR")(OH).

In an exemplary embodiment of the present disclosure,

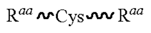

may be a single amino acid or protein including cysteine or a pseudo-cysteine residue;

$R^1$ to $R^5$ may be independently of one another hydrogen, C1-C7 alkyl, or C1-C7 alkoxy;

$R^6$ and $R^7$ may be independently of each other C1-C7 alkoxy or C6-C10 aryl;

$L^1$ may be C4-C10 alkylene or include 1 to 10—$OCH_2CH_2$-units;

X may be hydrogen, halogen, C1-C7 alkyl, or C1-C7 haloalkyl; and alkyl, alkoxy, or aryl of $R^1$ to $R^5$ may be further substituted by —OH, —OR', —COR', —NR'R", —NR-'COR", —NHCOR', —$NHCOCH_2NR'R"$, and —NR'PO(OR")(OH).

In an exemplary embodiment of the present disclosure, the protein may be an antibody, a fragment of antigenic polypeptide, or an artificial antibody.

In an exemplary embodiment of the present disclosure, an amino acid- or peptide conjugate represented by the following Chemical Formula 3 or Chemical Formula 4 is provided:

[Chemical Formula 3]

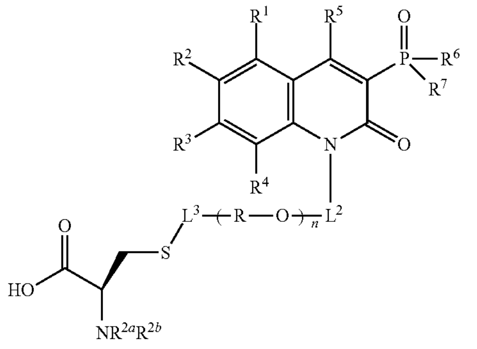

[Chemical Formula 4]

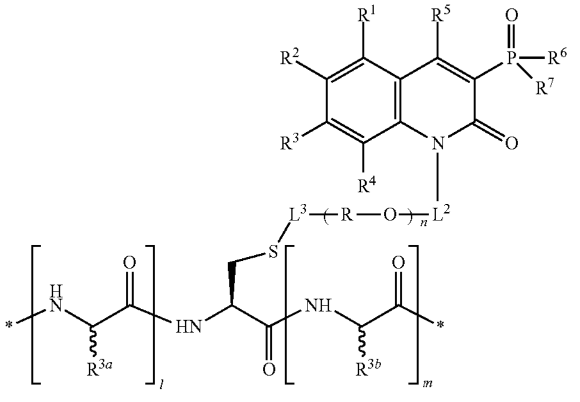

wherein $R^1$ to $R^7$ are as defined Chemical Formula 2, $L^2$, $L^3$, and R are C1-C5 alkylene, $L^2$, $L^3$, and R may be further substituted by one or more selected from halogen, C1-C10 alkyl, C1-C10 alkoxy, C1-C10 haloalkoxy, C6-C20 aryl, and combinations thereof, in Chemical Formula 3, $R^{2a}$ and $R^{2b}$ are independently of each other hydrogen or an acetyl group, in Chemical Formula 4, $R^{3a}$ and $R^{3b}$ are identical or different side chains of amino acid, and n is an integer of 0 to 10, and l and m are integers of 0 to 400.

In still another general aspect, an antibody-drug conjugate includes the amino acid- or peptide conjugate.

In an exemplary embodiment of the present disclosure, the drug may be an immunomodulatory compound, an anticancer compound, an antiviral agent, an antibacterial agent, an antifungal agent, an anthelmintic agent, or a combination thereof.

Advantageous Effects

The quinolinone derivative compound of the present disclosure includes an alkene moiety for cysteine-selective bioconjugation, thereby selectively producing a thiyl radical in a cysteine residue under visible light conditions to induce a thiol-ene reaction, which allows peptide or protein conjugation including cysteine.

The compound according to the present disclosure shows photocatalytic activity to visible light, whereby environmental sustainability is excellent, no external oxidizing agent is required, and thus, a side reaction of peptide including an oxidation-sensitive residue is prevented.

The compound according to the present disclosure has excellent compatibility with an aqueous medium so that a photochemical reaction in an aqueous solution may proceed well, and a reaction in vivo may be derived in a high yield under mild conditions without a further additive.

The compound according to the present disclosure undergoes a radical reaction using visible light, thereby improving instability due to the progress of a retro-Michael reaction in a cysteine conjugation using a conventional thiol-Michael reaction and showing high chemical selectivity even when other nucleophilic amino acids are present.

BEST MODE

Figure 1:
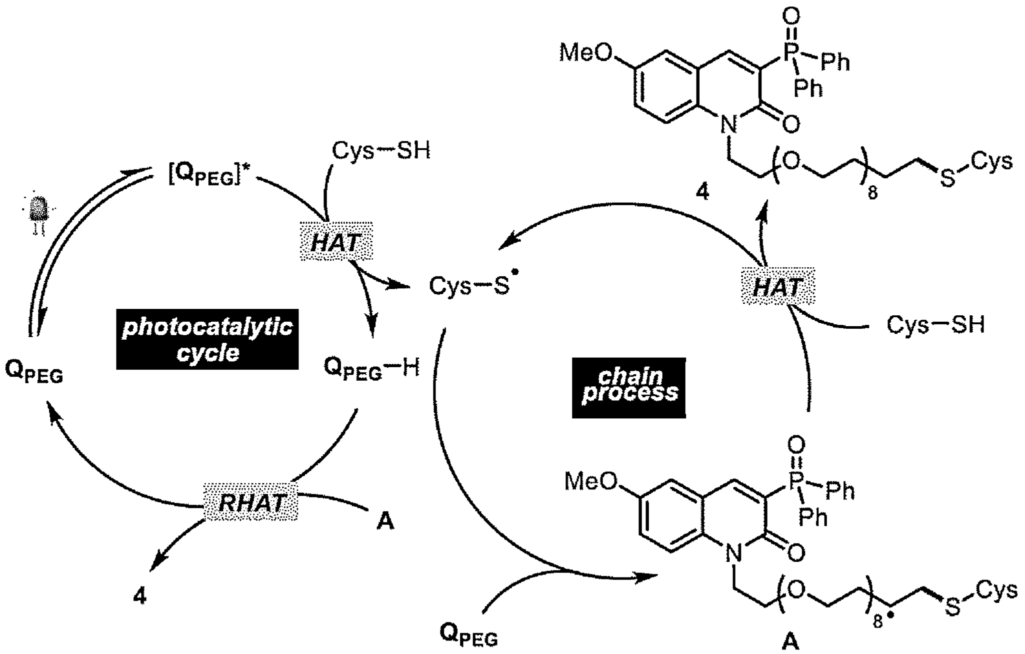
FIG. 1 shows the mechanism of a cysteine-specific conjugation of a quinolinone derivative compound $Q_{PEG}$ according to the present disclosure.
Figure 2A:
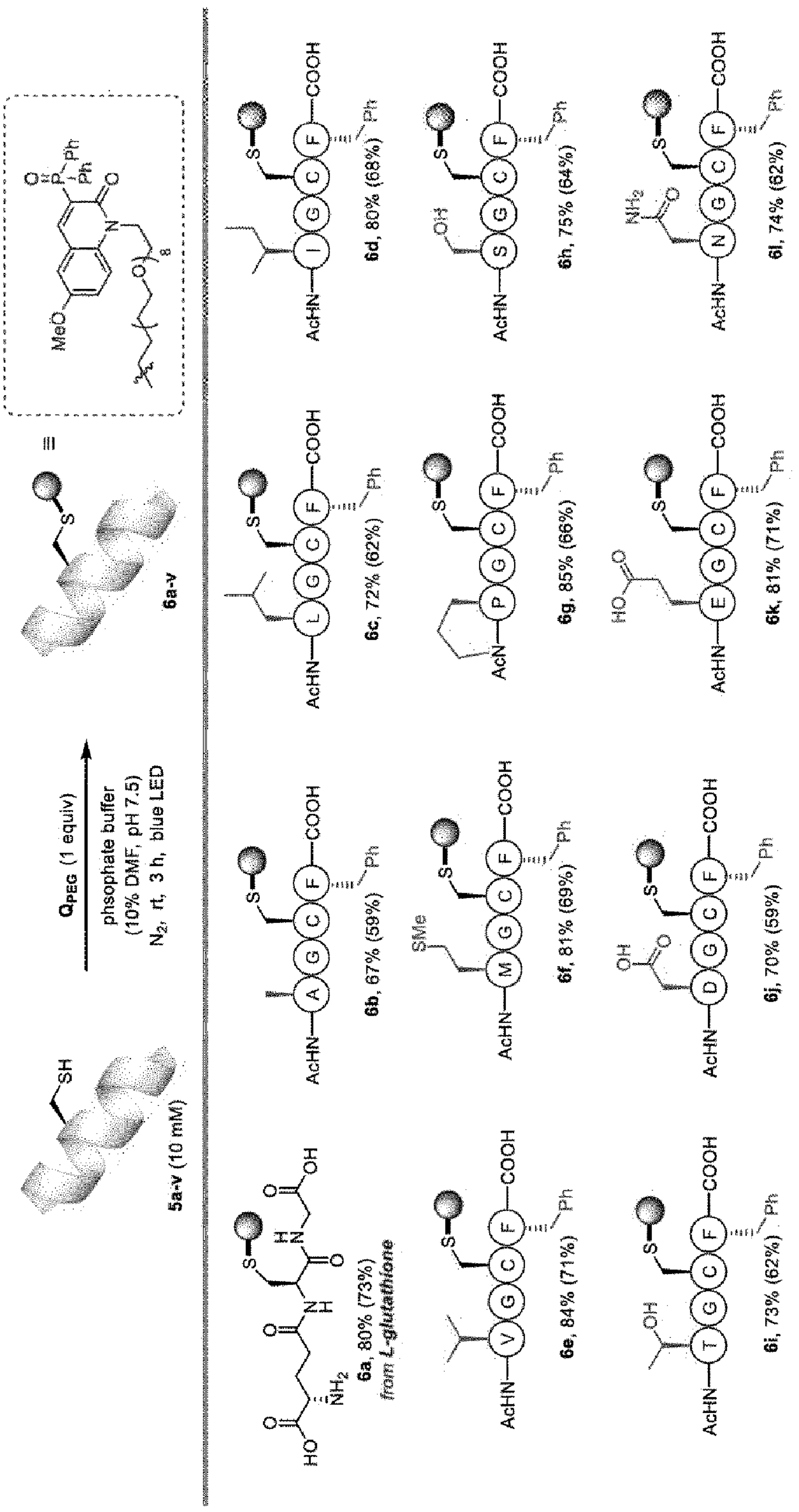
FIGS. 2*a* and 2*b* show the results of forming a peptide conjugate including the quinolinone derivative compound according to the present disclosure and cysteine.
Figure 2B:
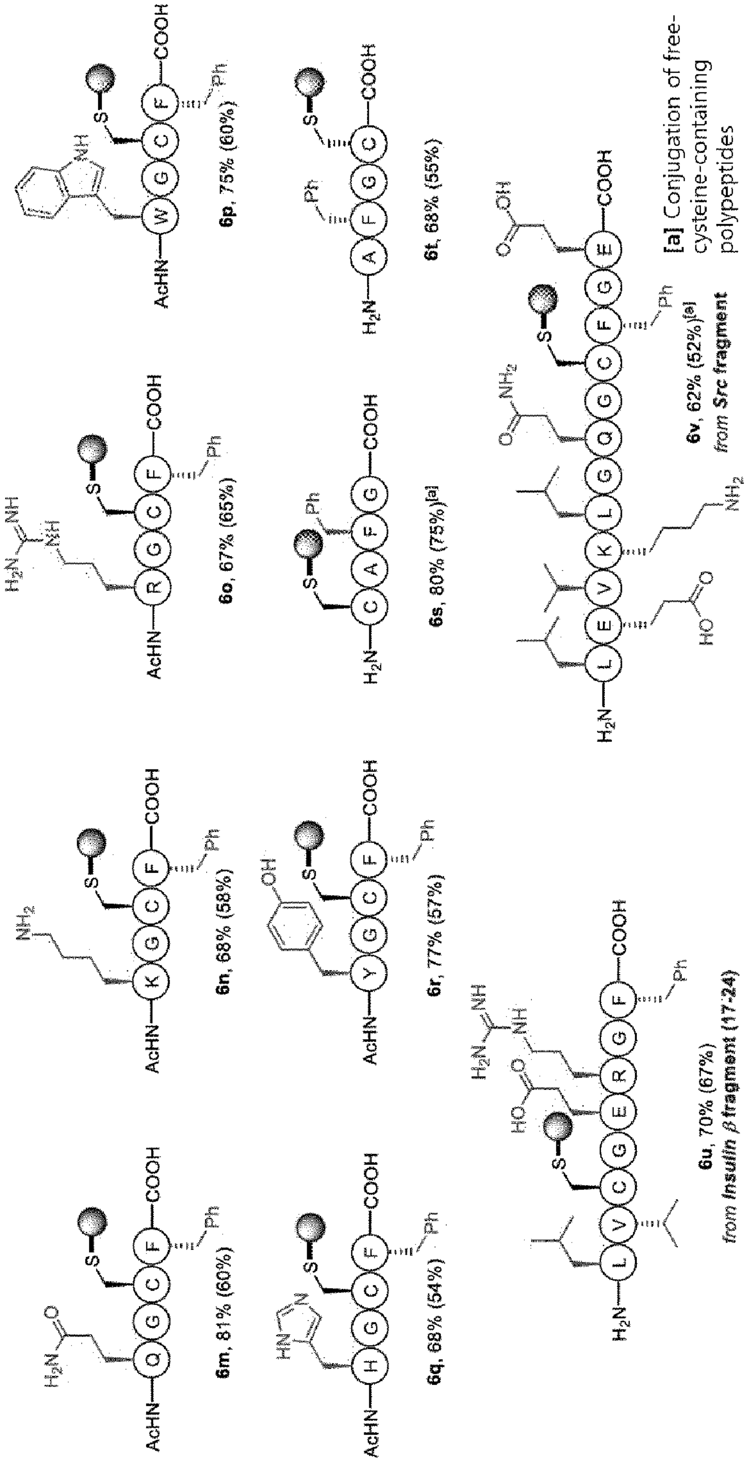

Hereinafter, the present disclosure will be described in detail. Herein, unless otherwise defined, all technical and scientific terms have the meaning commonly understood by those of ordinary skill in the art, and the terms used in the description of the present disclosure are only for effectively describing a certain example and are not intended to limit the present disclosure In addition, in the following description, description for well-known effects and configurations that may obscure the gist of the present disclosure unnecessarily will be omitted.

Hereinafter, units used in the present specification without particular mention are based on weights, and as an example, a unit of % or ratio refers to a wt % or a weight ratio.

In addition, in describing constituent elements of the present disclosure, terms such as first, second, A, B, (a), and (b) may be used. These terms are used only to differentiate the constituent elements from other constituent elements, and the nature, sequence, order, or the like of the corresponding constituent elements is not limited by these terms.

In addition, the singular form used in the specification of the present disclosure may be intended to include a plural form, unless otherwise indicated in the context.

"Alkyl", "alkoxy", and a substituent containing "alkyl" described in the present specification refer to a hydrocarbon radical in a linear or branched form having 1 to 20 carbon atoms.

"Alkenyl" described in the present specification is an organic radical derived from a hydrocarbon containing one or more double bonds.

"Alkynyl" in the present specification is an organic radical derived from a hydrocarbon containing one or more double bonds.

"Haloalkyl" described in the present specification refers to one or more hydrogens of the alkyl being substituted by one or more halogens, preferably fluorines.

"Aryl" described in the present specification is an organic radical derived from an aromatic hydrocarbon by removal of one hydrogen, refers to a monocyclic or fused ring system containing appropriately 4 to 7, preferably 5 or 6 ring atoms in each ring, and includes even a form in which a plurality of aryls are connected by a single bond. A specific example thereof includes phenyl, naphthyl, biphenyl, terphenyl, anthryl, indenyl, fluorenyl, phenanthryl, triphenylenyl, pyrenyl, perylenyl, cryceny, naphthacenyl, fluoranthenyl, and the like. The naphthyl includes 1-naphthyl and 2-naphthyl, anthryl includes 1-anthryl, 2-anthryl, and 9-anthryl, and fluorenyl includes all of 1-fluorenyl, 2-fluorenyl, 3-fluorenyl, 4-fluorenyl, and 9-fluorenyl.

"Heteroaryl" described in the present specification refers to an aryl group containing 1 to 4 heteroatoms selected from the group consisting of B, N, O, S, P(=O), Si, and P as an aromatic ring backbone atom, and carbons as remaining aromatic ring backbone atoms, and is a 5- or 6-membered monocyclic heteroaryl and a polycyclic heteroaryl fused with one or more benzene rings, which may be partially saturated. In addition, the heteroaryl in the present disclosure also includes a form in which one or more heteroaryls are linked by a single bond.

The present disclosure relates to a quinolinone derivative compound producing an excellent cysteine-selective conjugate, and may be represented by the following Chemical Formula 1:

[Chemical Formula 1]

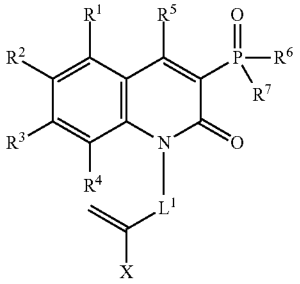

wherein $R^1$ to $R^5$ are independently of one another hydrogen, C1-C20 alkyl, C3-C20 cycloalkyl, C3-C20 heterocycloalkyl, C1-C20 alkoxy, C6-C20 aryl, or C3-C20 heteroaryl;

$R^6$ and $R^7$ are independently of each other hydrogen, C1-C20 alkyl, C1-C20 alkoxy, C6-C20 aryl, or C3-C20 heterocycloalkyl;

$L^1$ is C4-C20 alkylene or C1-C20 oxyalkylene;

X is hydrogen, halogen, C1-C10 alkyl, C1-C7 haloalkyl, C1-C10 alkoxy, C1-C10 haloalkoxyl, or C6-C20 aryl;

the heteroaryl and the heterocycloalkyl independently of each other contain one or more heteroatoms selected from nitrogen, oxygen, and sulfur; and alkyl, cycloalkyl, heterocycloalkyl, alkoxy, aryl, and heteroaryl of $R^1$ to $R^5$ may be further substituted by —OH, —OR', —COR', —NR'R", —NR'COR", —NHCOR', —$NHCOCH_2NR'R"$, and —NR'PO(OR")(OH).

The quinolinone derivative compound which selectively binds to cysteine of the present disclosure binds to the thiol group of cysteine in high selectivity and yield under mild conditions, thereby forming a cysteine conjugate. Furthermore, it may selectively react with oligopeptide, polypeptide, and protein including cysteine, and may easily produce an antibody-drug conjugate including a peptide conjugate produced as a result of the reaction.

The quinolinone derivative compound including the alkene moiety of the present disclosure starts from an organic photocatalyst Q1 which was developed by the present inventors:

$Q_1$

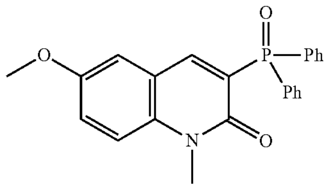

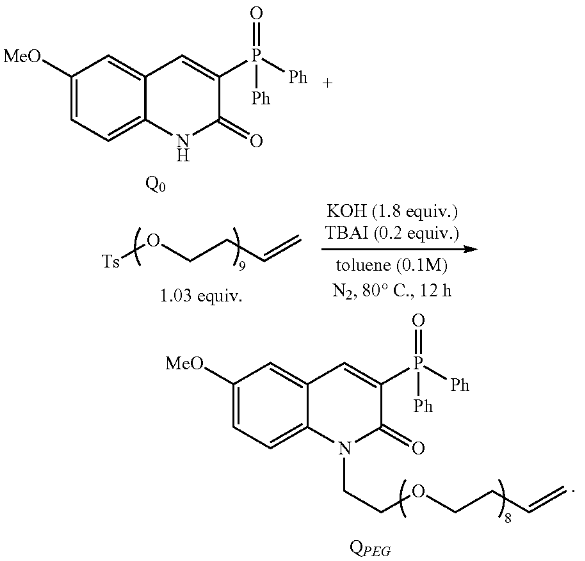

$Q_0$ 1.03 equiv.

$Q_{PEG}$

The quinolinone derivative compound according to the present disclosure is prepared by imparting an alkene moiety according to the above method from $Q_0$ obtained by removing a methyl group from $Q_1$, and this will be described in detail in Example I.

In addition, $Q_{CAT}$ may be prepared according to the following method from $Q_0$ obtained by removing a methyl group from $Q_1$, and this will be described later in detail in Example IV:

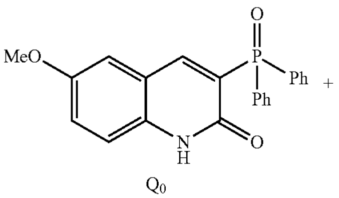

$Q_0$

-continued

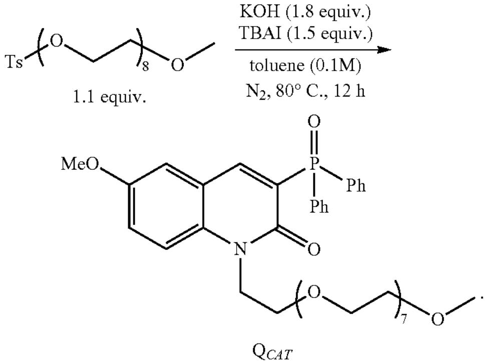

1.1 equiv.

$Q_{CAT}$

When visible light is irradiated, the quinolinone derivative compound according to the present disclosure may selectively produce a radical in a cysteine residue by hydrogen atom transfer (HAT). Here, the visible light may be preferably blue light in a range of 380 to 500 nm.

When quinolinone derivative compound according to the present disclosure is exposed to visible light without addition of an external oxidizing agent, it produces the radical, is characterized by showing excellent functional group resistance even in a peptide to which amino acids other than cysteine have been added, and may provide an effect of preventing a side reaction of peptide including an oxidation-sensitive residue and excellent cysteine selectivity.

In addition, the present disclosure provides an amino acid- or peptide conjugate represented by the following Chemical Formula 2:

[Chemical Formula 2]

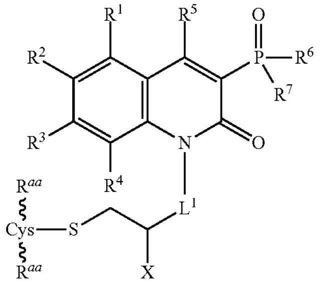

wherein

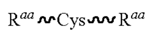

is a single amino acid, oligopeptide, polypeptide, or protein including cysteine or a pseudo-cysteine residue;

$R^1$ to $R^5$ are independently of one another hydrogen, C1-C20 alkyl, C3-C20 cycloalkyl, C3-C20 heterocycloalkyl, C1-C20 alkoxy, C6-C20 aryl, or C3-C20 heteroaryl;

$R^6$ and $R^7$ are independently of each other hydrogen, C1-C20 alkyl, C1-C20 alkoxy, C6-C20 aryl, or C3-C20 heterocycloalkyl;

$L^1$ is C4-C20 alkylene or C1-C20 oxyalkylene;

X is hydrogen, halogen, C1-C10 alkyl, C1-C7 haloalkyl, C1-C10 alkoxy, C1-C10 haloalkoxyl, or C6-C20 aryl;

the heteroaryl and the heterocycloalkyl independently of each other contain one or more heteroatoms selected from nitrogen, oxygen, and sulfur; and alkyl, cycloalkyl, heterocycloalkyl, alkoxy, aryl, and heteroaryl of $R^1$ to $R^5$ may be further substituted by any one or more selected from the group consisting of —OR', —COR', —NR'R", —NR'COR", —NHCOR', —$NHCOCH_2NR'R"$, and NR'PO(OR")(OH), and R' and R" are independently of each other any one selected from the group consisting of hydrogen, C1-C7 alkyl, C3-C6 cycloalkyl, C3-C6 alkenyl, and C3-C6 alkynyl.

The amino acid- or peptide conjugate may be prepared by a thiol-ene reaction of the quinolinone derivative compound according to the present disclosure and a single amino acid- or peptide. The peptide means that a peptide bond formed by bonding two or more amino acids is included, and may include oligopeptide, polypeptide, or protein.

The thiol-ene reaction is a reaction initiated by a radical, and may be described as a reaction of bonding a thiyl radical by a double bond and a Michael addition reaction of thiol by a catalyst in a defective part of an electron in a carbon double bond. Specifically, a method of reacting a compound containing a thiol group, for example, cysteine with olefin or an alkyne-containing reactant to be bonded to other functional groups of peptide at a rapid reaction rate is provided. In the present disclosure, the reaction proceeds under mild conditions, and is not limited by pH.

In an exemplary embodiment of the present disclosure, the thiol-ene reaction for preparing the amino acid- or peptide conjugate may proceed in acetonitrile or DMF alone, or a mixed solvent thereof with a buffer at 1:1 to 1:10, but the solvent is not particularly limited thereto as long as it may dissolve the quinolinone derivative compound as a reactant. The buffer may be a phosphate buffer, a sodium acetate buffer, a HEPES buffer, a tris buffer, or the like.

The amino acid- or peptide conjugate according to the present disclosure may be used as a fluorescent photosensitizer to visible light.

In addition, the present disclosure provides an amino acid- or peptide conjugate represented by the following Chemical Formula 3 or Chemical Formula 4:

[Chemical Formula 3]

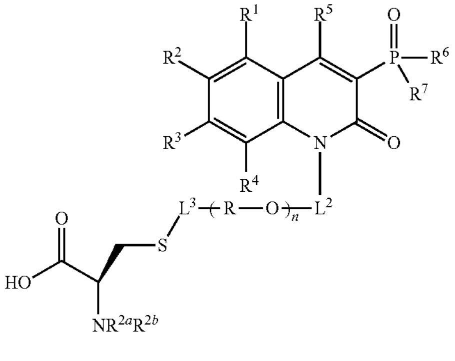

-continued

[Chemical Formula 4]

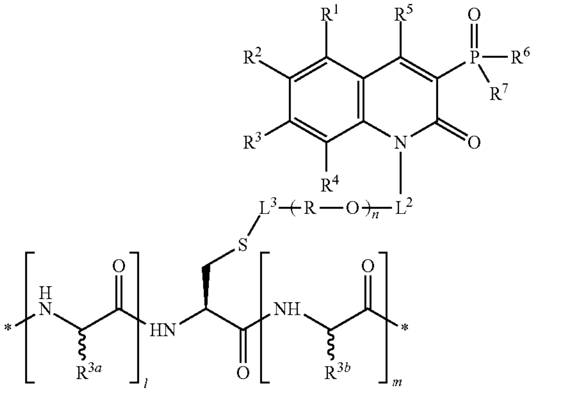

wherein $R^1$ to $R^7$ are as defined in claim 5, $L^2$, $L^3$, and R are C1-C5 alkylene, $L^2$, $L^3$, and R may be further substituted by one or more selected from halogen, C1-C10 alkyl, C1-C10 alkoxy, C1-C10 haloalkoxyl, C6-C20 aryl, and combinations thereof, in Chemical Formula 3, $R^{2a}$ and $R^{2b}$ are independently of each other hydrogen or an acetyl group, in Chemical Formula 4, $R^{3a}$ and $R^{3b}$ are identical or different side chains of amino acid, and n is an integer of 0 to 10, and 1 and m are integers of 0 to 400.

Preferably, 1 and m may be 0 to 300, more preferably 0 to 100.

In the case of the amino acid conjugate according to Chemical Formula 3, the amino acid is a cysteine-bonded form, preferably N-acetylated cysteine. In addition, the peptide conjugate according to Chemical Formula 4 includes cysteine or pseudo-cysteine, and may include serine (S), threonine (T), aspartic acid (D), asparagine (N), glutamic acid (E), glutamine (Q), lysine (K), arginine (R), glycine (G), alanine (A), phenylalanine (F), leucine (L), isoleucine (I), valine (V), methionine (M), proline (P), tryptophan (W), tyrosine (Y), or histidine (H) as other amino acids, but is not particularly limited thereto.

In a specific exemplary embodiment of the present disclosure, the peptide conjugate may include 2 to 20-mer oligopeptide, 50 to 100-mer polypeptide, or 500-mer or higher protein. The peptide conjugate includes one or two or more cysteine or pseudo-cysteine residues, and may be produced by one or two or more quinolinone derivative compounds and a thiol-ene reaction. Accordingly, the peptide conjugate may be in the form in which a plurality of the quinolinone derivative compounds according to the present disclosure are branched and bonded.

The present disclosure provides an antibody-drug conjugate including the amino acid- or peptide conjugate described above. The drug may be an immunomodulatory compound, an anticancer compound, an antiviral agent, an antibacterial agent, an antifungal agent, an anthelmintic agent, or a combination thereof.

The immunomodulatory compound may be selected from the group consisting of aminocaproic acid, azathioprine, bromocriptine, chloroquine, chlorambucil, cyclosporine, cyclosporine A, danazol, dehydroepiandrosterone (DHEA), dexamethasone, etanercept, hydroxychloroquine, hydrocortisone, infliximab, meloxicam, methotrexate, cyclophosphamide, mycophenolate mofetil, prednisone, sirolimus, and tacrolimus. The anticancer compound may be selected from the group consisting of methotrexate, taxol, L-asparaginase, mercaptopurine, thioguanine, hydroxyurea, cytarabine, cyclophosphamide, ifosfamide, nitrosourea, cisplatin, carboplatin, mitomycin, dacarbazine, procarbazine, topotecan, nitrogen mustard, cytoxan, etoposide, 5-fluorouracil, bischloroethylnitrosourea (BCNU), irinotecan, camptothecin, bleomycin, doxorubicin, idarubicin, daunorubicin, dactinomycin, plicamycin, mitoxantrone, asparaginase, vinblastine, vincristine, vinorelbine, paclitaxel, docetaxel, chlorambucil, melphalan, carmustine, lomustine, busulfan, treosulfan, decarbazine, etoposide, teniposide, topotecan, 9-aminocamptothecin, crisnatol, mitomycin C, trimetrexate, mycophenolic acid, tiazofurin, ribavirin, 5-ethynyl-1-beta-Dribofuranosylimidazole-4-carboxamide (EICAR), hydroxyurea, deferoxamine, floxuridine, doxifluridine, raltitrexed, cytarabine (ara C), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, photosensitizer Pe4, demethoxyhypocrellin A, Interferon-α, Interferon-γ, tumor necrosis factor, Gemcitabine, velcade, revamid, thalamid, lovastatin, 1-methyl-4-phenylpyridinium ion, staurosporine, actinomycin D, dactinomycin, bleomycin A2, bleomycin B2, peplomycin, epirubicin, pirarubicin, zorubicin, mitoxantrone, verapamil, and thapsigargin.

The antiviral agent may be selected from the group consisting of pencicyclovir, valacyclovir, ganciclovir, foscarnet, ribavirin, idoxuridine, vidarabine, trifluridine, acyclovir, famciclovir, amantadine, rimantadine, cidofovir, antisense oligonucleotide, immunoglobulin, and interferon.

The antibacterial agent may be selected from the group consisting of chloramphenicol, vancomycin, metronidazole, trimethoprim, sulfamethizole, quinupristin, dalfopristin, rifampin, spectinomycin, and nitrofurantoin. The antifungal agent may be selected from the group consisting of amphotericin B, Candicidin, filipin, hamycin, natamycin, nystatin, rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, Itraconazole, Posaconazole, Ravuconazole, Terconazole, Voriconazole, Abafungin, Amorolfin, Butenafine, Naftifine, Terbinafine, Anidulafungin, Caspofungin, Micafungin, benzoic acid, ciclopirox, flucytosine, griseofulvin, haloprogin, tolnaftate, undecylenic acid, crystal violet, balsam of peru, Ciclopirox olamine, Piroctone olamine, Zinc pyrithione, and selenium sulfide.

The helminthic may be selected from the group consisting of mebendazole, pyrantel pamoate, thiabendazole, diethylcarbamazine, ivermectin, niclosamide, praziquantel, albendazole, rifampin, amphotericin B, melarsoprol, eflornithine, metronidazole, tinidazole, and miltefosine.

The antibody-drug conjugate including Chemical Formula 2 according to the present disclosure may be used for treating a subject by delivering a drug to the target cell of the subject, using a preparation method of a composition known to a person skilled in the art.

The composition may be a liquid solution or suspension, and may be prepared in an injectable form. The antibody-drug conjugate may be blended with a pharmaceutically acceptable carrier, and an appropriate carrier is usually a slowly metabolizing macromolecule, and for example, may include protein, polysaccharide, polylactic acid, polyglycolic acid, polymeric amino acid, amino acid copolymer, lipid aggregate, and the like The above composition may also include a diluent, for example, water, brine, glycerol, or ethanol. An auxiliary material, for example, a wetting agent or an emulsifying agent, a pH buffer material, or the like may also be present. Protein may be formulated into a vaccine in a neutral or salt form. The composition may be administrated parenterally by injection; and the injection may be subcutaneous or intramuscular. An additional formulation may be, for example, appropriate for other administration forms, for example, by suppository or orally. An oral composition may be administered as a solution, a suspension, a tablet, a pill, a capsule, or a sustained-release formulation.

The composition is administered in a manner compatible with a dosage formulation. The composition includes a therapeutically effective amount of antibody-drug conjugate compound. The therapeutically effective amount refers to a composition which is effective for treatment or prevention of a disease or disorder and is administered in a single dose or on a multiple dose schedule. An administered dose varies with a subject to be treated, the health and physical conditions of the subject, a protection degree to be desired, and other related factors. The precise required amount of active components follows the doctor's judgment.

In addition, the present disclosure provides the quinolinone derivative compound represented by the following Chemical Formula 5:

[Chemical Formula 5]

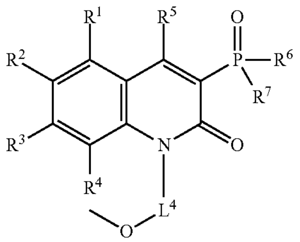

- $R^1$ to $R^5$ are independently of one another hydrogen, C1-C20 alkyl, C3-C20 cycloalkyl, C3-C20 heterocycloalkyl, C1-C20 alkoxy, C6-C20 aryl, or C3-C20 heteroaryl;
- $R^6$ and $R^7$ are independently of each other hydrogen, C1-C20 alkyl, C1-C20 alkoxy, C6-C20 aryl, or C3-C20 heterocycloalkyl;
- $L^4$ is C4-C20 alkylene or C1-C20 oxyalkylene;
- X is hydrogen, halogen, C1-C10 alkyl, C1-C7 haloalkyl, C1-C10 alkoxy, C1-C10 haloalkoxy, or C6-C20 aryl; and
- the heteroaryl and the heterocycloalkyl independently of each other may contain one or more heteroatoms selected from nitrogen, oxygen, and sulfur.

In a preferred exemplary embodiment of the present disclosure, in Chemical Formula 5, $L^4$ may include 1 to 10—$OCH_2CH_2$— units.

The quinolinone derivative compound represented by Chemical Formula 5 shows photocatalytic activity by visible light, and may derive a cysteine-selective conjugation reaction of an alkene substrate. When excited by visible light, the quinolinone derivative compound according to the present disclosure acts as a photocatalyst under hydration synthesis conditions without a metal, an oxidizing agent, or an external photocatalyst, by hydrogen atom transfer (HAT).

Here, any alkene substrate may be used without limitation as long as it may proceed with a thiol-ene reaction with the thiol group of cysteine, and preferably, may include an unsubstituted vinyl group.

Hereinafter, the present disclosure will be described in more detail through the following examples. However, the following examples are only a reference for describing the present disclosure in detail, and the present disclosure is not limited thereto and may be implemented in various forms.

MODE FOR INVENTION

[Preparation Example 1] Preparation of Compound $Q_0$

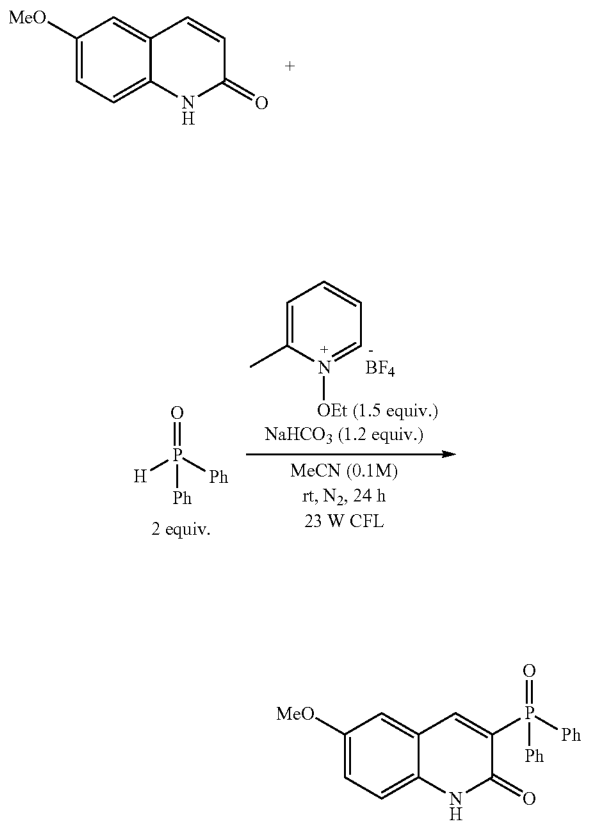

$Q_0$ 701 mg (4 mmol) of 6-methoxyquinolin-2(1H)-one, 2 equivalents of diphenyl phosphine oxide, 1.5 equivalents of N-ethoxy-2-methylpyridinium tetrafluoroborate, and 1.2 equivalents of sodium bicarbonate were put into a two-neck round bottom flask, which was filled with nitrogen. The mixture was treated with anhydrous acetonitrile (40 ml) under a nitrogen atmosphere, and stirred in 23 W CFL conditions at room temperature for 24 hours. The reaction was monitored by TLC, and after the reaction was completed, the mixture was filtered with acetonitrile (20 ml), and the filtered solid was dried under vacuum to obtain a light green solid, $Q_0$ (880 mg, 59%).

[Example I] Preparation of Quinolinone Derivative Compound

Preparation of Compound $Q_{ENE}$

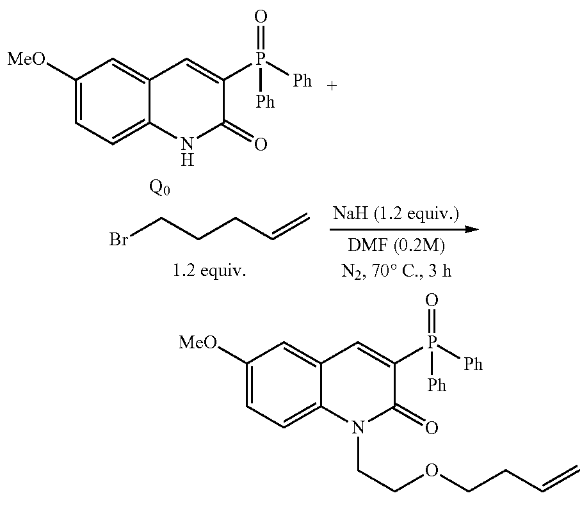

$Q_{ENE}$ 5 mg (1.0 mmol) of 3-(diphenylphosphoryl)-6-methoxyquinolin-2 (1H)-one ($Q_0$), 1.2 equivalents of 5-bromopenten-1-ene, and 1.2 equivalents of sodium hydride were put into two-neck round bottom flask, which was filled with nitrogen. Dimethylformamide (DMF, 5 ml) was added to the flask by a syringe, and then stirring was performed at 70° C. for 3 hours. After the reaction was completed, distilled water was added to the flask at 0° C., the mixture was diluted with ethyl acetate (20 ml), and washed with water (20 ml×2). An organic phase was removed by a rotary evaporator, and the residues were purified by RP-HPLC using water and methanol to obtain 111 mg (25%) of a $Q_{ENE}$ compound.

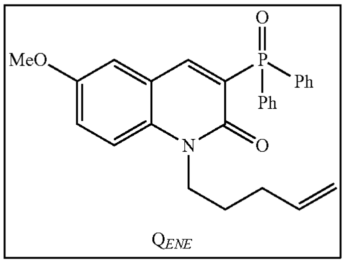 [SMILES: C=CCCCn1c(=O)c(P(=O)(c2ccccc2)c2ccccc2)cc2cc(OC)ccc21]

$Q_{ENE}$ $^1H$ NMR (600 MHz, $CD_3OD$) δ 8.56 (d, J=14.7 Hz, 1H), 7.88-7.80 (m, 4H), 7.63 (td, J=7.4, 1.5 Hz, 2H), 7.58-7.50 (m, 6H), 7.41 (dd, J=9.3, 2.9 Hz, 1H), 7.38 (d, J=3.0 Hz, 1H), 5.82 (ddt, J=17.0, 10.2, 6.7 Hz, 1H), 5.01 (dq, J=17.0, 1.5 Hz, 1H), 4.95 (dt, J=10.2, 1.5 Hz, 1H), 4.28-4.21 (m, 2H), 3.89 (s, 3H), 2.12 (q, J=7.2 Hz, 2H), 1.75 (p, J=7.6 Hz, 2H). $^{13}C$ NMR (150 MHz, $CDCl_3$) δ 159.7 (d, J=11.8 Hz), 154.6, 148.4 (d, J=5.5 Hz), 137.1, 135.4, 131.9 (d, J=10.5 Hz), 131.7 (d, J=109.6 Hz), 131.7 (d, J=2.8 Hz), 128.1 (d, J=12.9 Hz), 125.2 (d, J=106.2 Hz), 122.0, 120.7 (d, J=12.6 Hz), 115.4, 115.4, 111.2, 55.6, 41.9, 30.8, 26.4. $^{31}P$ NMR (162 MHz, $CDCl_3$) δ 25.0. HRMS (ESI+) m/z calcd. For $[C_{27}H_{26}NNaO_3P]^+$: 466.1543, found: 466.1538. IR: 3047, 2934, 1629, 1562, 1233. MP: 169° C.

Preparation of Compound $Q_{PEG}$

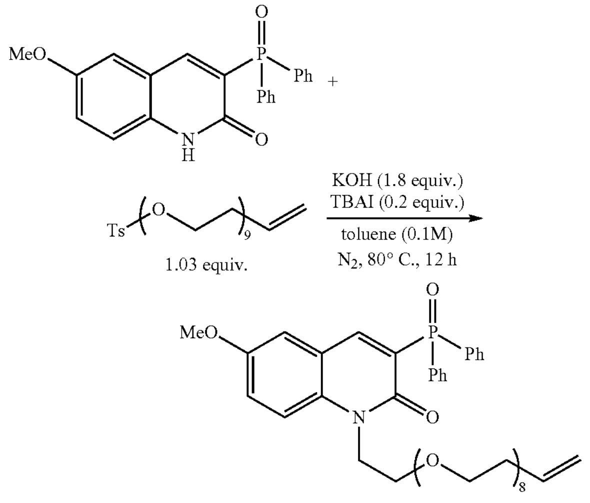

$Q_{PEG}$ $Q_0$, tosylate (1.03 equiv.), potassium hydroxide (1.8 equiv.), and tetra-n-butylammonium bromide (0.2 equiv.) were put into a two-neck round bottom flask, which was filled with nitrogen. Toluene (22 ml) was injected into the flask with a syringe, and stirring was performed at 80° C. for 12 hours. After the reaction was completed, the solvent was removed by a rotary evaporator, distilled water was put into the mixture, and extraction through 2-propanol/chloroform (1:4)(50 ml×3) was performed. After the solvent was removed, the residue was purified by RP-HPLC using water and methanol, thereby obtaining 540 mg (33%) of a $Q_{PEG}$ compound.

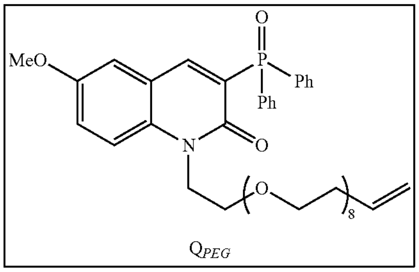

$Q_{PEG}$ $^1H$ NMR (400 MHz, $CD_3OD$) δ 8.58 (d, J=14.7 Hz, 1H), 7.86 (ddt, J=12.8, 7.1, 1.4 Hz, 4H), 7.68 (d, J=9.2 Hz, 1H), 7.65-7.58 (m, 2H), 7.53 (ddd, J=8.6, 6.8, 3.2 Hz, 4H), 7.38-7.31 (m, 2H), 5.81 (ddt, J=17.0, 10.2, 6.7 Hz, 1H), 5.06 (dq, J=17.0, 1.8 Hz, 1H), 4.99 (dq, J=10.2, 1.8, 1.1 Hz, 1H), 4.44 (t, J=5.7 Hz, 2H), 3.87 (s, 3H), 3.73 (t, J=5.7 Hz, 2H), 3.65-3.39 (m, 30H), 2.29 (qt, J=6.7, 1.5 Hz, 2H). $^{13}C$ NMR (100 MHz, $CD_3OD$) δ 161.5 (d, J=12.0 Hz), 156.7, 150.3 (d, J=6.0 Hz), 137.6 (d, J=1.8 Hz), 136.5, 133.6 (d, J=2.9 Hz), 133.1 (d, J=10.7 Hz), 132.3 (d, J=110.9 Hz), 129.7 (d, J=12.9 Hz), 124.8 (d, J=111.0 Hz), 124.1, 122.1 (d, J=12.9 Hz), 118.5, 116.7, 112.1, 71.7, 71.7, 71.6, 71.5, 71.5, 71.5, 71.2, 69.3, 56.3, 43.5, 35.2. $^{31}P$ NMR (162 MHz, $CD_3OD$) δ 29.3. HRMS (ESI+) m/z calcd. For $[C_{42}H_{56}NNaO_{11}P]^+$: 804.3483, found: 804.3482. IR: 2862, 1636, 1564, 1436, 1235, 1101. MP: 61° C.

[Example II] Preparation of Cysteine-Quinolinone Derivative Conjugate

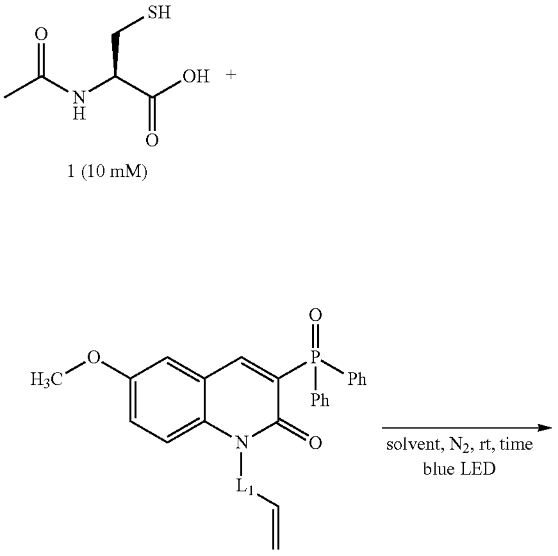

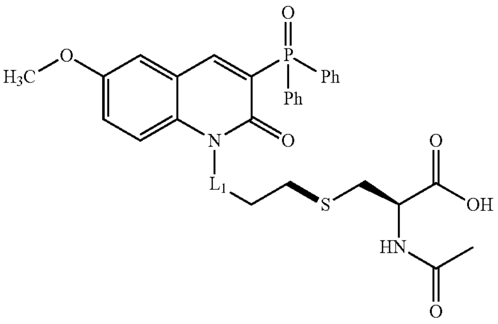

A pH 7.5 phosphate buffer including 0 to 100% v/v acetonitrile ($CH_3CN$) or dimethylformamide (DMF) was put into a test tube and was subjected to a degassing process according to Freeze-pump-thaw, N-acetyl cysteine (10 mM) and a quinolinone derivative (1 equiv.) were added to the buffer solution, irradiation with a blue light source (440 nm, 8.5 W, Kessil blue LED) was performed at room temperature under a nitrogen atmosphere, and stirring was performed to proceed with the reaction. After the reaction was completed, 0.5 ml (DABCO, 2 equiv.) of a 1,4-diazabicyclo[2.2.2] octane stock solution was added, the solvent was removed by a rotary evaporator, and purification was performed with RP-HPLC to prepare a conjugate.

Example II-1. Preparation of Compound S5

8.2 mg (68%) of Compound S5 was prepared in the same manner as in the above preparation method, except that only acetonitrile was used as the solvent.

S5

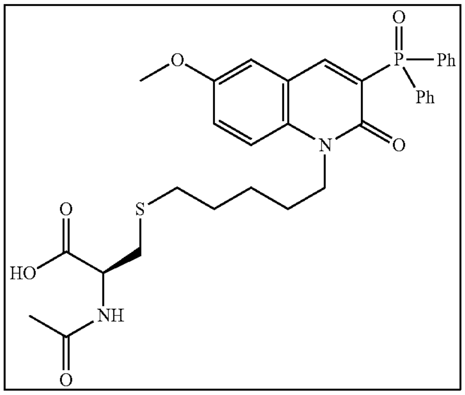

N-acetyl-S-(5-(3-(diphenylphosphoryl)-6-methoxy-2-oxoquinolin-1(2H)-yl)pentyl)-L-cysteine $^1$H NMR (400 MHz, $CD_3OD$) δ 8.55 (d, J=14.7 Hz, 1H), 7.90-7.78 (m, 4H), 7.61 (td, J=7.3, 1.5 Hz, 2H), 7.56-7.46 (m, 5H), 7.36 (dd, J=9.3, 2.9 Hz, 1H), 7.31 (d, J=2.9 Hz, 1H), 4.55 (dd, J=8.0, 4.8 Hz, 1H), 4.21 (t, J=7.5 Hz, 2H), 3.85 (s, 3H), 2.96 (dd, J=13.8, 4.8 Hz, 1H), 2.78 (dd, J=14.0, 8.0 Hz, 1H), 2.48 (t, J=7.2 Hz, 2H), 1.97 (s, 3H), 1.65 (p, J=7.6 Hz, 2H), 1.56 (p, J=7.2 Hz, 2H), 1.45-1.33 (m, 2H). $^{13}$C NMR (100 MHz, $CD_3OD$) δ 173.8, 173.2, 161.3 (d, J=10.3 Hz), 156.7, 150.0 (d, J=5.9 Hz), 136.7, 133.6 (d, J=2.9 Hz), 133.0 (dd, J=10.5, 1.8 Hz), 132.2 (d, J=111.4 Hz), 129.7 (d, J=12.9 Hz), 124.8 (d, J=111.7 Hz), 124.3, 122.2 (d, J=12.8 Hz), 117.6, 112.4, 56.3, 53.7, 43.2, 34.4, 33.0, 30.1, 28.2, 26.7, 22.4. $^{31}$P NMR (162 MHz, $CD_3OD$) δ 29.5. HRMS (ESI+) m/z calcd. 607.2026 For $[C_{32}H_{36}N_2O_6PS]^+$: 607.2030.

Example II-2. Preparation of Compound 4

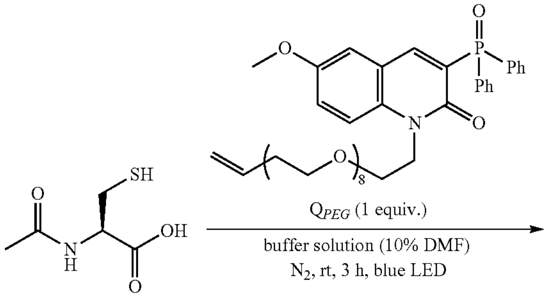

1 (10 mM)

-continued

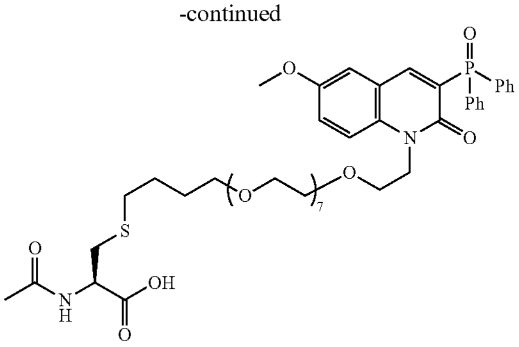

4

Compound 4 (14.7 mg, 78%) was prepared in the same manner as in the above preparation method, except that a phosphate buffer (PB) and DMF were used at 9:1 as the solvent.

4

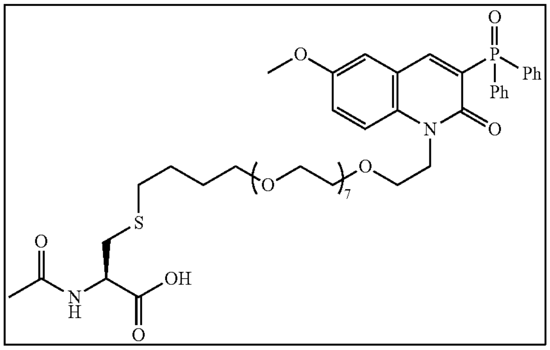

N-Acetyl-L-cysteine-Q$_{PEG}$ $^1$H NMR (600 MHz, $CD_3OD$) δ 8.59 (d, J=14.7 Hz, 1H), 7.90-7.81 (m, 4H), 7.71 (d, J=9.2 Hz, 1H), 7.65-7.60 (m, 2H), 7.53 (td, J=7.8, 2.9 Hz, 4H), 7.41-7.34 (m, 2H), 4.57 (dd, J=8.1, 4.8 Hz, 1H), 4.46 (t, J=5.7 Hz, 2H), 3.88 (s, 3H), 3.75 (t, J=5.7 Hz, 2H), 3.65-3.40 (m, 30H), 3.01 (dd, J=13.8, 4.8 Hz, 1H), 2.82 (dd, J=13.8, 8.1 Hz, 1H), 2.58 (d, J=6.6 Hz, 2H), 1.99 (s, 3H), 1.63 (tt, J=6.6, 3.4 Hz, 4H). $^{13}$C NMR (100 MHz, $CD_3OD$) δ 174.0, 173.2, 161.5 (d, J=12.0 Hz), 156.7, 150.4 (d, J=6.1 Hz), 137.5 (d, J=1.7 Hz), 133.6 (d, J=2.9 Hz), 133.1 (d, J=10.7 Hz), 132.3 (d, J=110.8 Hz), 129.7 (d, J=12.8 Hz), 124.7 (d, J=110.8 Hz), 124.1, 122.1 (d, J=12.9 Hz), 118.5, 112.1, 71.7, 71.7, 71.5, 71.5, 71.5, 71.5, 71.4, 71.2, 69.3, 56.3, 53.8, 43.5, 34.5, 32.9, 29.7, 27.2, 22.4. $^{31}$P NMR (162 MHz, $CD_3OD$) δ 28.8. HRMS (ESI+) m/z calcd. For $[C_{47}H_{66}N_2O_{14}PS]^+$: 945.3967, found: 945.3970.

[Example III] Preparation of Peptide Conjugate

A pH 7.5 phosphate buffer (PB, 20 mM) or a sodium acetate buffer (pH 3.5, 20 mM) and 10% v/v DMF were put into a test tube, and a degassing process was performed according to Freeze-pump-thaw. Each of peptides 5a to 5v (10 mM) and $Q_{PEG}$ (1 equiv.) were added to the buffer solution under a nitrogen atmosphere, and the mixture was irradiated with a blue light source (440 nm, 8.5 W, Kessil blue LED) at room temperature and stirred to proceed with the reaction. After the reaction was completed, 0.5 mL (DABCO, 2 equiv.) of a 1,4-diazabicyclo[2.2.2]octane stock solution was added, the solvent was removed by a rotary evaporator, and purification was performed with RP-HPLC to prepare a conjugate.

Example III-1. Preparation of Glutathione-$Q_{PEG}$ (6a)

17.5 mg (73%) of Compound 6a was obtained in the same manner as in the preparation method described in Example III.

6a

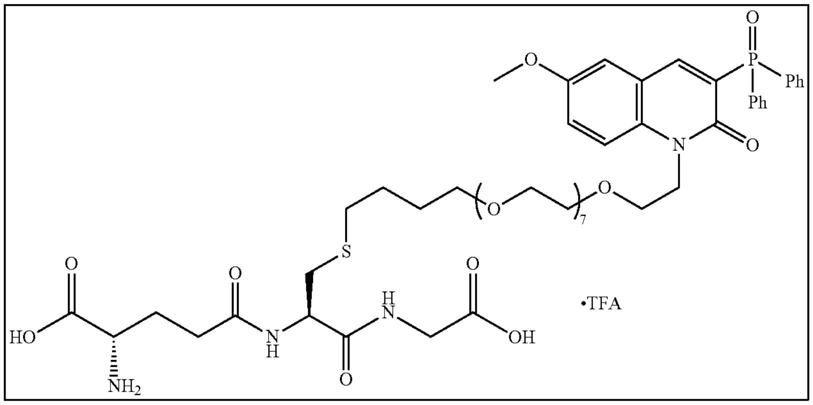

$^{1}H$ NMR (600 MHz, $CD_3OD$) δ 8.55 (d, J=14.7 Hz, 1H), 7.88-7.81 (m, 4H), 7.72 (d, J=9.3 Hz, 1H), 7.65-7.61 (m, 2H), 7.57-7.51 (m, 4H), 7.38 (dd, J=9.2, 3.0 Hz, 1H), 7.36 (d, J=2.9 Hz, 1H), 4.58 (dd, J=9.1, 5.1 Hz, 1H), 4.48 (t, J=5.7 Hz, 2H), 4.05 (t, J=6.3 Hz, 1H), 3.92 (d, J=2.7 Hz, 2H), 3.88 (s, 3H), 3.76 (t, J=5.7 Hz, 2H), 3.63-3.51 (m, 22H), 3.50-3.43 (m, 8H), 3.01 (dd, J=14.0, 5.1 Hz, 1H), 2.74 (dd, J=14.0, 9.1 Hz, 1H), 2.57 (t, J=6.9 Hz, 4H), 2.27-2.20 (m, 1H), 2.19-2.11 (m, 1H), 1.68-1.60 (m, 4H). $^{13}C$ NMR (150 MHz, $CD_3OD$) δ 174.4, 173.2, 172.6, 171.6, 162.5 (d, J=35.1 Hz), 161.6 (d, J=11.6 Hz), 156.8, 150.4 (d, J=6.0 Hz), 137.5, 133.6 (d, J=2.9 Hz), 133.1 (dd, J=10.4, 1.7 Hz), 132.3 (d, J=111.0 Hz), 129.7 (d, J=12.8 Hz), 124.8 (d, J=110.9 Hz), 124.1, 122.1 (d, J=13.2 Hz), 118.5, 118.0 (d, J=291.6 Hz), 112.2, 71.7, 71.7, 71.5, 71.5, 71.4, 71.1, 69.3, 56.3, 54.3, 53.7, 43.5, 41.8, 34.8, 32.8, 32.5, 29.7, 27.2, 27.1. $^{31}P$ NMR (162 MHz, $CD_3OD$) δ 29.5. $^{19}F$ NMR (376 MHz, $CD_3OD$) 5-77.0. HRMS (ESI+) m/z calcd. For $[C_{52}H_{74}N_4O_{17}PS]^+$: 1089.4502. found: 1089.4498.

Example III-2. Preparation of AGCF-$Q_{PEG}$ (6b)

14.3 mg (59%) of Compound 6b was obtained according to the above preparation method.

6b

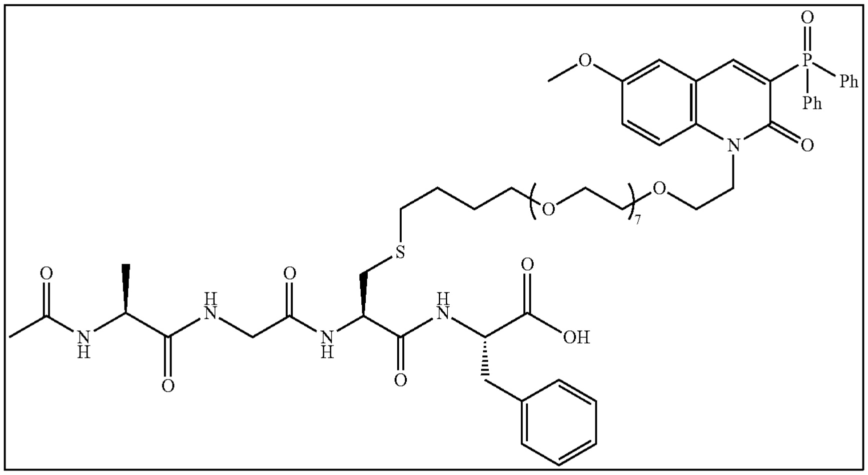

$^{1}$H NMR (600 MHz, $CD_3OD$) δ 8.58 (d, J=14.6 Hz, 1H), 7.89-7.80 (m, 4H), 7.71 (d, J=9.2 Hz, 1H), 7.62 (td, J=7.4, 1.4 Hz, 2H), 7.53 (td, J=7.8, 2.7 Hz, 4H), 7.41-7.35 (m, 2H), 7.27-7.21 (m, 4H), 7.21-7.16 (m, 1H), 4.64 (t, J=8.4, 5.2 Hz, 1H), 4.49 (dd, J=8.8, 5.3 Hz, 1H), 4.46 (t, J=5.6 Hz, 2H), 4.27 (q, J=7.2 Hz, 1H), 3.90 (d, J=16.7 Hz, 1H), 3.88 (s, 3H), 3.82 (d, J=16.7 Hz, 1H), 3.75 (t, J=5.6 Hz, 2H), 3.62-3.49 (m, 22H), 3.48-3.41 (m, 8H), 3.19 (dd, J=14.0, 5.2 Hz, 1H), 3.02 (dd, J=14.0, 8.4 Hz, 1H), 2.89 (dd, J=13.9, 5.3 Hz, 1H), 2.71 (dd, J=13.9, 8.8 Hz, 1H), 2.56-2.46 (m, 2H), 1.98 (s, 3H), 1.66-1.53 (m, 4H), 1.36 (d, J=7.2 Hz, 3H). $^{13}$C NMR (150 MHz, $CD_3OD$) δ 175.8, 174.1, 173.5, 172.4, 171.5, 161.6 (d, J=13.2 Hz), 156.7, 150.4 (d, J=5.9 Hz), 138.3, 137.6, 133.6 (d, J=2.5 Hz), 133.1 (d, J=10.5 Hz), 132.3 (d, J=110.4 Hz), 130.4, 129.7 (d, J=12.7 Hz), 129.4, 127.8, 124.7 (d, J=110.4 Hz), 124.1, 122.1 (d, J=13.0 Hz), 118.5, 112.1, 71.7, 71.7, 71.6, 71.5, 71.5, 71.5, 71.5, 71.5, 71.1, 69.4, 56.3, 55.2, 54.3, 51.1, 43.6, 43.6, 38.4, 34.5, 32.7, 29.7, 27.2, 22.6, 17.6. $^{31}$P NMR (162 MHz, $CD_3OD$) δ 28.9. HRMS (ESI+) m/z calcd. For $[C_{61}H_{82}N_5NaO_{17}PS]^+$: 1242.5056, found: 1242.5062.

Example III-3. Preparation of LGCF-$Q_{PEG}$ (6c)

15.7 mg (62%) of Compound 6c was obtained according to the above preparation method.

6c

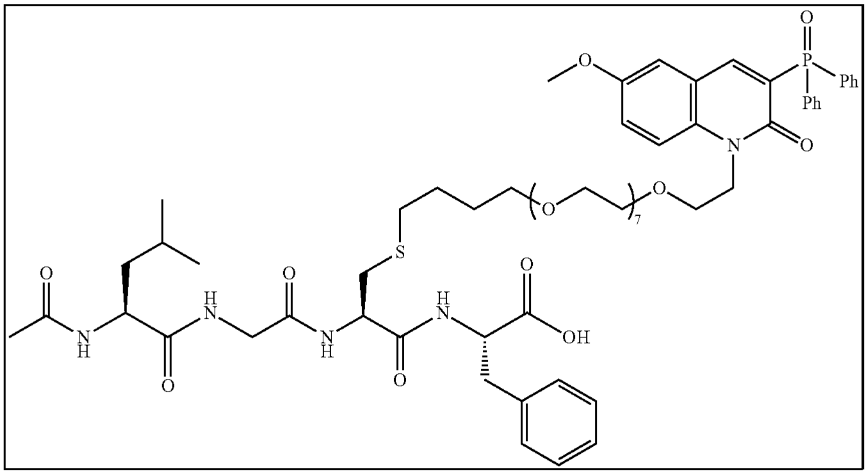

$^1H$ NMR (600 MHz, $CD_3OD$) δ 8.58 (d, J=14.7 Hz, 1H), 7.85 (ddt, J=12.8, 7.0, 1.4 Hz, 4H), 7.75-7.68 (m, 1H), 7.68-7.58 (m, 2H), 7.53 (td, J=7.5, 3.2 Hz, 4H), 7.38 (dd, J=9.7, 2.0 Hz, 2H), 7.31-7.12 (m, 5H), 4.64 (dd, J=8.3, 5.1 Hz, 1H), 4.53-4.43 (m, 3H), 4.35-4.29 (m, 1H), 3.92 (d, J=16.7 Hz, 1H), 3.88 (s, 3H), 3.80 (d, J=16.7 Hz, 1H), 3.75 (t, J=5.6 Hz, 2H), 3.63-3.50 (m, 22H), 3.49-3.41 (m, 8H), 3.19 (dd, J=14.0, 5.1 Hz, 1H), 3.02 (dd, J=14.0, 8.3 Hz, 1H), 2.89 (dd, J=13.9, 5.4 Hz, 1H), 2.71 (dd, J=14.0, 8.7 Hz, 1H), 2.55-2.43 (m, 2H), 1.99 (s, 3H), 1.76-1.53 (m, 7H), 0.95 (dd, J=16.0, 6.2 Hz, 6H). $^{13}C$ NMR (150 MHz, $CD_3OD$) δ 175.6, 174.1, 173.7, 172.4, 171.4, 161.6 (d, J=11.8 Hz), 156.7, 150.4 (d, J=6.0 Hz), 138.3, 137.6, 133.6 (d, J=2.8 Hz), 133.1 (d, J=10.5 Hz), 132.3 (d, J=110.9 Hz), 130.4, 129.7 (d, J=13.0 Hz), 129.4, 127.8, 124.7 (d, J=110.8 Hz), 124.1, 122.1 (d, J=12.8 Hz), 118.5, 112.1, 71.7, 71.5 71.5, 71.5, 71.5, 71.5, 71.5, 71.1, 69.4, 56.3, 55.2, 54.3, 53.9, 43.6, 43.6, 41.6, 38.4, 34.5, 32.7 (d, J=2.7 Hz), 29.7, 27.2 (d, J=1.8 Hz), 25.9, 23.4, 22.5, 22.1. $^{31}P$ NMR (162 MHz, $CD_3OD$) δ 28.8. HRMS (ESI+) m/z calcd. For $[C_{64}H_{88}N_5NaO_{17}PS]^+$: 1284.5526, found: 1284.5518.

Example III-4. Preparation of IGCF-$Q_{PEG}$ (6d)

6d

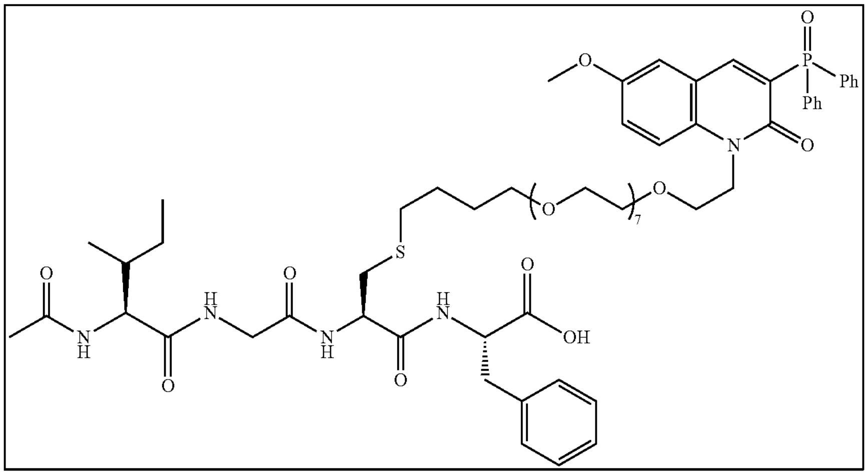

$^1H$ NMR (600 MHz, $CD_3OD$) δ 8.57 (d, J=14.7 Hz, 1H), 7.85 (ddd, J=12.8, 8.2, 1.4 Hz, 4H), 7.71 (d, J=9.2 Hz, 1H), 7.63 (td, J=7.4, 1.5 Hz, 2H), 7.53 (td, J=7.8, 3.0 Hz, 4H), 7.41-7.34 (m, 2H), 7.29-7.15 (m, 5H), 4.65 (dd, J=8.5, 5.2 Hz, 1H), 4.52-4.43 (m, 3H), 4.14 (d, J=7.3 Hz, 1H), 3.93 (d, J=16.7 Hz, 1H), 3.88 (s, 3H), 3.81 (d, J=16.7 Hz, 1H), 3.75 (t, J=5.7 Hz, 2H), 3.62-3.50 (m, 22H), 3.50-3.41 (m, 8H), 3.19 (dd, J=13.9, 5.2 Hz, 1H), 3.02 (dd, J=13.9, 8.5 Hz, 1H), 2.88 (dd, J=13.9, 5.4 Hz, 1H), 2.71 (dd, J=13.9, 8.7 Hz, 1H), 2.66 (s, 1H), 2.51 (q, J=6.6 Hz, 2H), 1.99 (s, 3H), 1.89-1.78 (m, 1H), 1.66-1.53 (m, 4H), 1.27-1.17 (m, 1H), 0.95 (d, J=6.8 Hz, 3H), 0.92 (t, J=7.3 Hz, 3H). $^{13}C$ NMR (100 MHz, $CD_3OD$) δ 174.5, 174.1, 173.7, 172.4, 171.4, 161.6 (d, J=11.9 Hz), 156.7, 150.4 (d, J=6.1 Hz), 138.3, 137.5 (d, J=1.6 Hz), 133.6 (d, J=2.9 Hz), 133.1 (d, J=10.7 Hz), 132.3 (d, J=110.8 Hz), 130.5, 129.7 (d, J=12.8 Hz), 129.4, 127.8, 124.7 (d, J=112.7 Hz), 122.1 (d, J=13.1 Hz), 118.5, 112.1, 71.7, 71.7, 71.5, 71.5, 71.5, 71.4, 71.4, 71.4, 71.4, 71.1, 69.4, 60.1, 56.3, 55.2, 54.3, 43.5, 40.4, 38.4, 37.6, 34.4, 32.7, 29.7, 27.2, 26.2, 22.5, 15.9, 11.5. $^{31}P$ NMR (162 MHz, $CD_3OD$) δ 28.9. HRMS (ESI+) m/z calcd. For $[C_{64}H_{88}N_5Na_2O_{17}PS]^+$: 653.7709, found: 653.7709.

Example III-5. Preparation of VGCF-$Q_{PEG}$ (6e)

6e

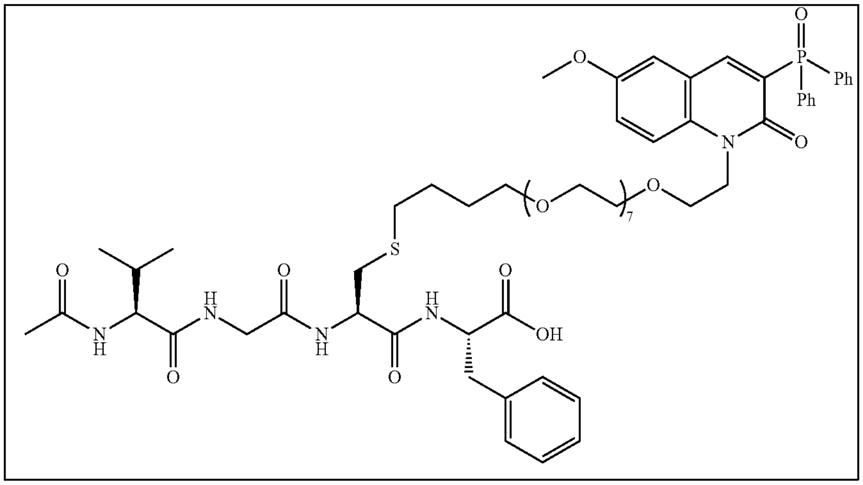

17.7 mg (71%) of Compound 6e was obtained according to the above preparation method.

$^{1}$H NMR (600 MHz, $CD_3OD$) δ 8.59 (d, J=14.7 Hz, 1H), 7.89-7.81 (m, 5H), 7.71 (d, J=9.1 Hz, 1H), 7.63 (td, J=7.3, 1.5 Hz, 2H), 7.53 (td, J=7.7, 3.1 Hz, 4H), 7.41-7.33 (m, 2H), 7.28-7.20 (m, 4H), 7.21-7.15 (m, 1H), 4.64 (dd, J=8.3, 5.2 Hz, 1H), 4.50 (dd, J=8.7, 5.4 Hz, 1H), 4.46 (t, J=5.7 Hz, 2H), 4.09 (d, J=7.1 Hz, 1H), 3.94 (d, J=16.7 Hz, 1H), 3.88 (s, 3H), 3.82 (d, J=16.7 Hz, 1H), 3.75 (t, J=5.7 Hz, 2H), 3.61-3.50 (m, 22H), 3.49-3.42 (m, 8H), 3.19 (dd, J=14.0, 5.2 Hz, 1H), 3.02 (dd, J=14.0, 8.3 Hz, 1H), 2.88 (dd, J=13.9, 5.4 Hz, 1H), 2.71 (dd, J=13.9, 8.7 Hz, 1H), 2.56-2.46 (m, 2H), 2.14-2.05 (m, 1H), 2.00 (s, 3H), 1.65-1.54 (m, 4H), 0.98 (t, J=7.1 Hz, 6H). $^{13}$C NMR (150 MHz, $CD_3OD$) δ 174.4, 174.3, 173.7, 172.4, 171.4, 161.5 (d, J=11.9 Hz), 156.7, 150.4 (d, J=5.7 Hz), 138.3, 137.6, 133.6, 133.1 (d, J=10.6 Hz), 132.3 (d, J=110.7 Hz), 130.5, 129.7 (d, J=12.9 Hz), 129.4, 127.8, 124.7 (d, J=110.7 Hz), 124.1, 122.1 (d, J=12.8 Hz), 118.5, 112.1, 71.7, 71.6, 71.5, 71.5, 71.1, 69.4, 61.1 (d, J=3.8 Hz), 56.3 (d, J=6.7 Hz), 55.2, 54.3 (d, J=3.5 Hz), 43.6, 43.5, 38.4, 34.5, 32.7, 31.3, 29.7, 27.2, 22.5, 19.7, 18.9. $^{31}$P NMR (162 MHz, $CD_3OD$) δ 28.8. HRMS (ESI+) m/z calcd. For $[C_{63}H_{86}N_5NaO_{17}PS]^+$: 1270.5369, found: 1270.5363.

Example III-6. Preparation of MGCF-$Q_{PEG}$ (6f)

6f

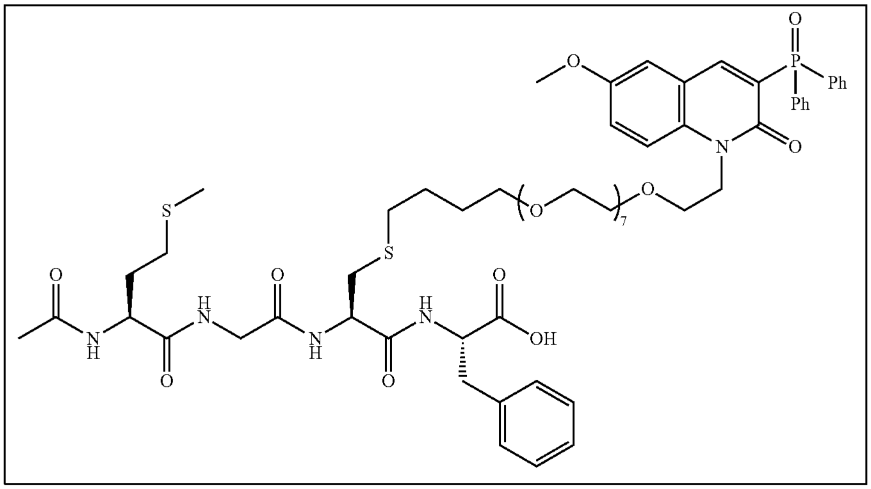

17.7 mg (69%) of Compound 6f was obtained according to the above preparation method.

$^{1}$H NMR (600 MHz, $CD_3OD$) δ 8.59 (d, J=14.7 Hz, 1H), 7.88-7.82 (m, 4H), 7.71 (d, J=9.1 Hz, 1H), 7.65-7.58 (m, 2H), 7.56-7.50 (m, 4H), 7.40-7.34 (m, 2H), 7.28-7.20 (m, 4H), 7.21-7.15 (m, 1H), 4.64 (dd, J=8.4, 5.2 Hz, 1H), 4.50 (dd, J=8.7, 5.4 Hz, 1H), 4.46 (t, J=5.7 Hz, 2H), 4.42 (dd, J=8.6, 5.5 Hz, 1H), 3.91 (d, J=16.7 Hz, 1H), 3.88 (s, 3H), 3.84 (d, J=16.7 Hz, 1H), 3.75 (t, J=5.7 Hz, 2H), 3.62-3.49 (m, 22H), 3.49-3.40 (m, 8H), 3.19 (dd, J=13.9, 5.3 Hz, 1H), 3.02 (dd, J=13.9, 8.4 Hz, 1H), 2.89 (dd, J=13.9, 5.4 Hz, 1H), 2.71 (dd, J=14.0, 8.7 Hz, 1H), 2.63-2.46 (m, 4H), 2.15-2.07 (m, 1H), 2.08 (s, 3H), 1.99 (s, 3H), 2.00-1.90 (m, 1H), 1.65-1.53 (m, 4H). $^{13}$C NMR (150 MHz, $CD_3OD$) δ 174.6, 174.2, 173.7, 172.4, 171.4, 161.5 (d, J=11.9 Hz), 156.7, 150.4 (d, J=5.9 Hz), 138.3, 137.6 (d, J=1.6 Hz), 133.6 (d, J=2.6 Hz), 133.1 (d, J=10.8 Hz), 132.3 (d, J=110.9 Hz), 130.5, 129.7 (d, J=13.0 Hz), 129.5, 127.8, 124.7 (d, J=110.7 Hz), 124.1, 122.1 (d, J=13.1 Hz), 118.5, 112.1, 71.7, 71.7, 71.7, 71.6, 71.5, 71.5, 71.5, 71.5, 71.5, 71.2, 69.4, 56.3, 55.2, 54.4, 54.3, 43.6, 43.6, 38.4, 34.5, 32.7, 32.2, 31.1, 29.7, 27.2, 22.6, 15.2. $^{31}$P NMR (162 MHz, $CD_3OD$) δ 29.4. HRMS (ESI+) m/z calcd. For $[C_{63}H_{86}N_5NaO_{17}PS_2]^+$: 1302.5090, found: 1302.5091.

Example III-7. Preparation of PGCF-$Q_{PEG}$ (6g)

6g

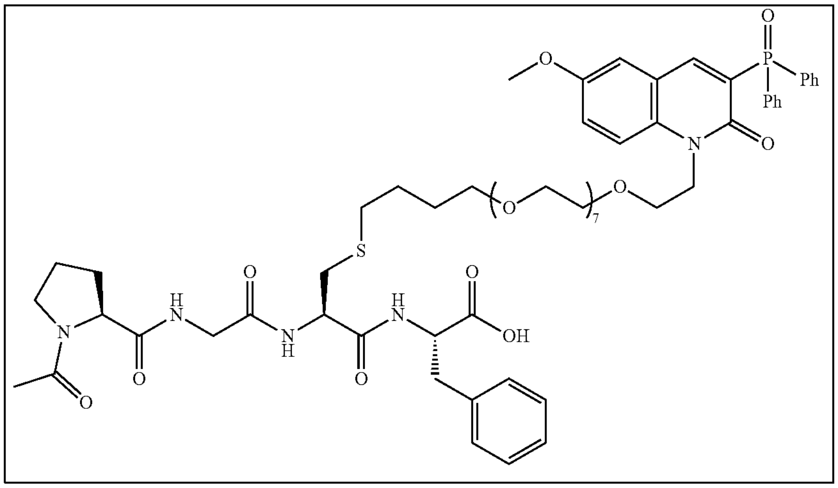

16.4 mg (66%) Compound 6g was obtained according to the above preparation method.

$^{1}H$ NMR (400 MHz, $CD_3OD$) δ 8.51 (d, J=14.8 Hz, 1H), 7.89-7.79 (m, 4H), 7.69 (d, J=9.3 Hz, 1H), 7.67-7.60 (m, 2H), 7.59-7.50 (m, 4H), 7.39 (dd, J=9.3, 3.0 Hz, 1H), 7.35 (d, J=2.9 Hz, 1H), 7.25-7.16 (m, 4H), 7.16-7.09 (m, 1H), 4.51 (t, J=5.5 Hz, 2H), 4.48-4.41 (m, 2H), 4.32 (dd, J=8.1, 5.1 Hz, 1H), 4.05 (d, J=16.9 Hz, 1H), 3.88 (s, 3H), 3.82-3.72 (m, 3H), 3.68-3.60 (m, 2H), 3.60-3.51 (m, 22H), 3.50-3.41 (m, 8H), 3.19 (dd, J=13.6, 4.7 Hz, 1H), 2.98 (dd, J=13.7, 7.2 Hz, 1H), 2.87 (dd, J=14.0, 4.8 Hz, 1H), 2.74 (dd, J=13.9, 9.7 Hz, 1H), 2.57-2.43 (m, 2H), 2.26-2.15 (m, 1H), 2.15-1.91 (m, 6H), 1.68-1.53 (m, 4H). $^{13}C$ NMR (150 MHz, $CD_3OD$) δ 175.4, 174.7, 172.5, 172.3, 171.7, 161.6 (d, J=11.8 Hz), 156.7, 150.4 (d, J=6.1 Hz), 138.5, 137.4, 133.6 (d, J=2.7 Hz), 133.1 (d, J=10.6 Hz), 132.2 (d, J=110.8 Hz), 130.5, 129.7 (d, J=12.8 Hz), 129.4, 127.7, 124.7 (d, J=110.9 Hz), 124.2, 122.1 (d, J=13.0 Hz), 118.4, 112.1, 71.7, 71.6, 71.4, 71.4, 71.4, 71.3, 71.3, 71.3, 71.3, 71.3, 71.3, 71.1, 69.3, 61.9, 56.3, 55.5, 54.6, 49.2, 43.7, 43.4, 38.5, 34.4, 32.6, 30.8, 29.7, 27.2, 25.9, 22.5. $^{31}P$ NMR (162 MHz, $CD_3OD$) δ 28.9. HRMS (ESI+) m/z calcd. For $[C_{63}H_{84}N_5NaO_{17}PS]^+$: 1268.5213, found: 1268.5213.

Example III-8. Preparation of SGCF-$Q_{PEG}$ (6h)

6h

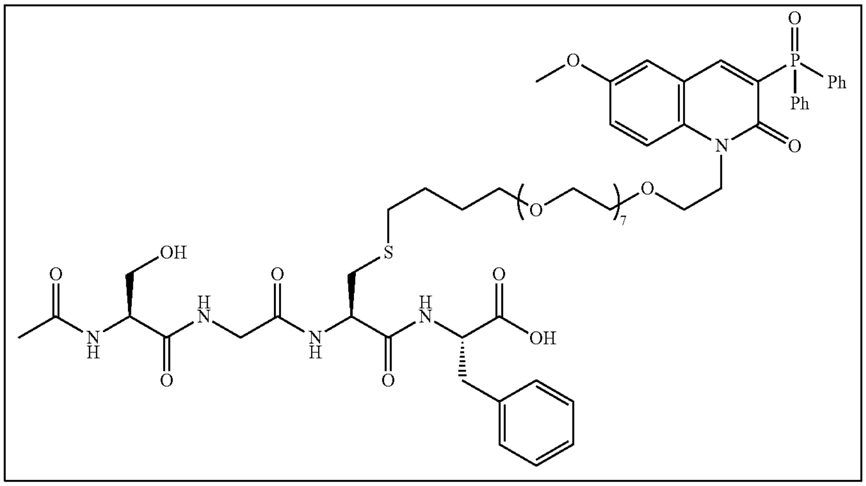

15.0 mg (57%) of Compound 6h was obtained according to the above preparation method.

$^{1}$H NMR (600 MHz, $CD_3OD$) δ 8.58 (d, J=14.6 Hz, 1H), 7.91-7.81 (m, 4H), 7.69 (dd, J=9.4, 3.5 Hz, 1H), 7.62 (t, J=7.5 Hz, 2H), 7.53 (td, J=7.8, 2.7 Hz, 4H), 7.41-7.32 (m, 2H), 7.28-7.20 (m, 4H), 7.20-7.15 (m, 1H), 4.64 (dd, J=8.4, 5.3 Hz, 1H), 4.51 (dd, J=8.9, 5.3 Hz, 1H), 4.45 (q, J=4.2, 2.4 Hz, 2H), 4.40-4.35 (m, 1H), 3.93 (d, J=16.9 Hz, 1H), 3.91-3.82 (m, 5H), 3.77 (dd, J=11.0, 5.4 Hz, 1H), 3.74 (t, J=5.7 Hz, 2H), 3.64-3.49 (m, 22H), 3.49-3.41 (m, 8H), 3.18 (dd, J=13.9, 5.3 Hz, 1H), 3.01 (dd, J=13.9, 8.4 Hz, 1H), 2.89 (dd, J=14.0, 5.3 Hz, 1H), 2.68 (dd, J=14.0, 8.9 Hz, 1H), 2.57-2.46 (m, 2H), 2.02 (s, 3H), 1.67-1.51 (m, 4H). $^{13}$C NMR (150 MHz, $CD_3OD$) δ 174.0, 173.7, 173.4, 172.4, 171.5, 161.6 (d, J=12.2 Hz), 156.7, 150.3 (d, J=5.9 Hz), 138.2, 137.5, 133.6 (d, J=2.6 Hz), 133.1 (d, J=10.5 Hz), 132.3 (d, J=110.6 Hz), 130.4, 129.7 (d, J=12.7 Hz), 129.4, 127.8, 124.7 (d, J=111.8 Hz), 122.0 (d, J=12.9 Hz), 118.5, 112.1, 71.7, 71.5, 71.5, 71.5, 71.5, 71.4, 71.1, 69.3, 63.0, 57.3, 56.3, 55.1, 54.3, 43.7, 43.5, 38.3, 34.5, 32.7, 29.7, 27.2, 22.6. $^{31}$P NMR (162 MHz, $CD_3OD$) δ 28.9. HRMS (ESI+) m/z calcd. For $[C_{61}H_{82}N_5O_{18}NaPS]^+$: 1258.5005, found 1258.5004.

Example III-9. Preparation of TGCF-$Q_{PEG}$ (6i)

6i

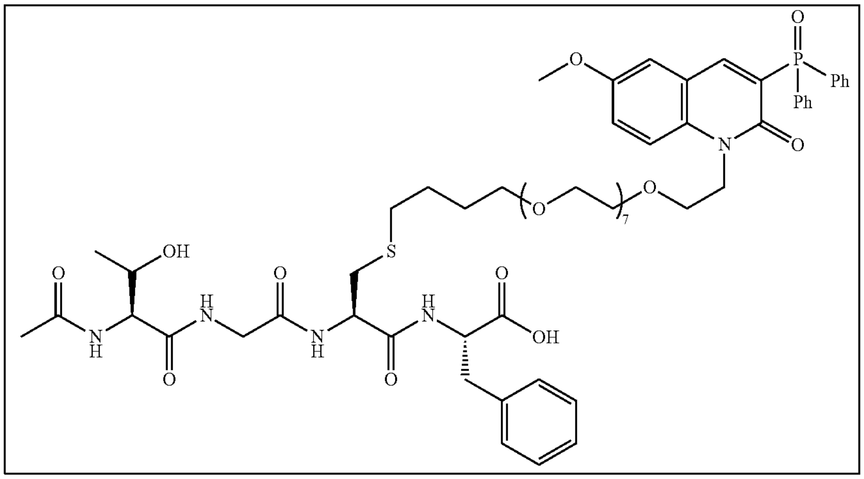

15.6 mg (62%) of Compound 6i was obtained according to the above preparation method.

$^1$H NMR (600 MHz, $CD_3OD$) δ 8.58 (d, J=14.7 Hz, 1H), 7.88-7.81 (m, 4H), 7.72 (d, J=9.1 Hz, 1H), 7.63 (td, J=7.4, 1.4 Hz, 2H), 7.53 (td, J=7.8, 2.9 Hz, 4H), 7.42-7.35 (m, 2H), 7.28-7.16 (m, 5H), 4.64 (dd, J=8.4, 5.3 Hz, 1H), 4.51 (dd, J=8.8, 5.4 Hz, 1H), 4.47 (t, J=5.7 Hz, 2H), 4.29 (d, J=3.8 Hz, 1H), 4.22 (qd, J=6.4, 3.8 Hz, 1H), 3.97 (d, J=16.8 Hz, 1H), 3.89 (s, 3H), 3.83 (d, J=16.8 Hz, 1H), 3.75 (t, J=5.7 Hz, 2H), 3.61-3.50 (m, 22H), 3.49-3.42 (m, 8H), 3.18 (dd, J=14.0, 5.3 Hz, 1H), 3.01 (dd, J=14.0, 8.4 Hz, 1H), 2.89 (dd, J=13.9, 5.4 Hz, 1H), 2.68 (dd, J=13.9, 8.8 Hz, 1H), 2.58-2.45 (m, 2H), 2.05 (s, 3H), 1.67-1.54 (m, 4H), 1.20 (d, J=6.3 Hz, 3H). $^{13}$C NMR (150 MHz, $CD_3OD$) δ 174.1, 173.9, 173.5, 172.4, 171.5, 161.6 (d, J=11.2 Hz), 156.7, 150.4 (d, J=6.0 Hz), 138.2, 137.6, 133.6 (d, J=2.7 Hz), 133.1 (d, J=10.6 Hz), 132.3 (d, J=110.8 Hz), 130.4, 129.7 (d, J=12.8 Hz), 129.5, 127.8, 124.7 (d, J=112.2 Hz), 122.1 (d, J=12.9 Hz), 118.5, 112.1, 71.7, 71.7, 71.6, 71.5, 71.5, 71.5, 71.5, 71.1, 69.4, 68.3, 60.7, 56.3, 55.2, 54.2, 43.6, 43.6, 38.3, 34.5, 32.7, 29.7, 27.2, 22.6, 20.0. $^{31}$P NMR (162 MHz, $CD_3OD$) δ 28.9. HRMS (ESI+) m/z calcd. For $[C_{62}H_{84}N_5NaO_{18}PS]^+$: 1272.5162, found 1272.5157.

Example III-10. Preparation of DGCF-$Q_{PEG}$ (6j)

6j

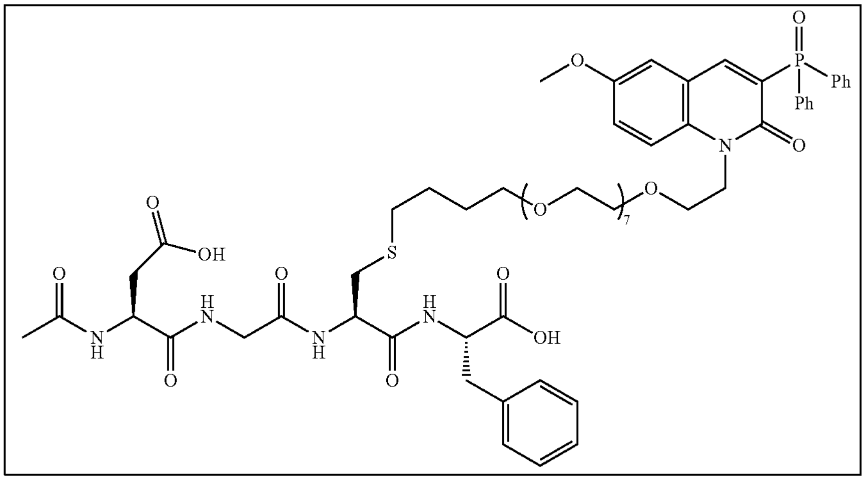

14.8 mg (59%) of Compound 6j was obtained according to the above preparation method.

$^1$H NMR (600 MHz, $CD_3OD$) δ 8.58 (d, J=14.7 Hz, 1H), 7.90-7.80 (m, 4H), 7.71 (d, J=9.2 Hz, 1H), 7.65-7.59 (m, 2H), 7.53 (td, J=7.7, 2.7 Hz, 4H), 7.40-7.34 (m, 2H), 7.29-7.15 (m, 5H), 4.68 (t, J=6.4 Hz, 1H), 4.64 (dd, J=8.4, 5.4 Hz, 1H), 4.51 (dd, J=9.0, 5.4 Hz, 1H), 4.46 (t, J=5.7 Hz, 2H), 3.96 (d, J=16.9 Hz, 1H), 3.88 (s, 3H), 3.78 (d, J=16.9 Hz, 1H), 3.75 (t, J=5.7 Hz, 2H), 3.63-3.49 (m, 22H), 3.49-3.40 (m, 8H), 3.18 (dd, J=14.0, 5.4 Hz, 1H), 3.02 (dd, J=14.0, 8.4 Hz, 1H), 2.91 (dd, J=14.0, 5.4 Hz, 1H), 2.88-2.77 (m, 2H), 2.72 (dd, J=14.0, 9.0 Hz, 1H), 2.57-2.46 (m, 2H), 2.00 (s, 2H), 1.66-1.54 (m, 4H). $^{13}$C NMR (150 MHz, $CD_3OD$) δ 174.2, 174.1, 173.7, 173.6, 172.5, 171.5, 161.7 (d, J=11.0 Hz), 156.7, 150.4 (d, J=5.8 Hz), 138.3, 137.6, 133.6, 133.1 (d, J=10.6 Hz), 132.3 (d, J=110.6 Hz), 130.4, 129.7 (d, J=12.7 Hz), 129.5, 127.8, 124.7 (d, J=110.6 Hz), 124.1, 122.1 (d, J=12.6 Hz), 118.5, 112.1, 71.7, 71.5, 71.5, 71.5, 71.1, 69.3, 56.4, 55.2, 54.4, 51.5, 43.8, 43.6, 38.4, 36.6, 34.4, 32.7, 29.7, 27.2, 22.7. $^{31}$P NMR (162 MHz, $CD_3OD$) δ 28.8. HRMS (ESI+) m/z calcd. For $[C_{62}H_{82}N_5NaO_{19}PS]_+$: 1286.4955. Found 1286.4955.

Example III-11. Preparation of EGCF-$Q_{PEG}$ (6k)

6k

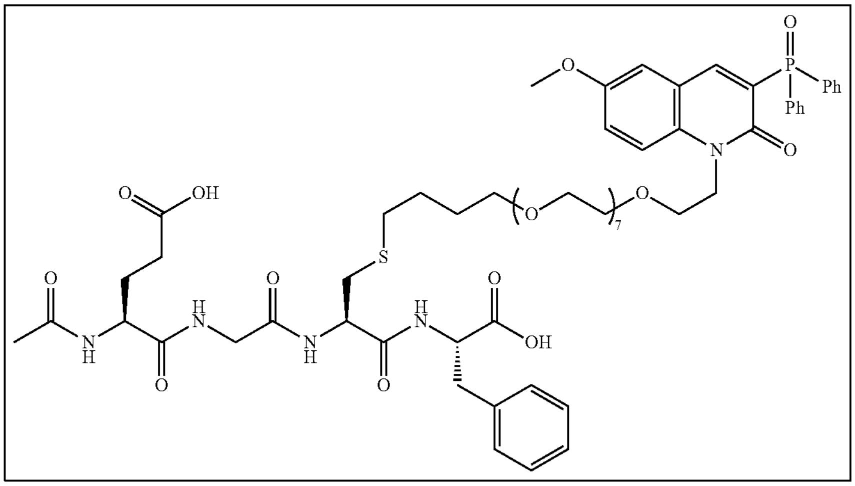

18.1 mg (71%) of Compound 6k was obtained according to the above preparation method.

$^{1}$H NMR (600 MHz, $CD_3OD$) δ 8.58 (d, J=14.7 Hz, 1H), 7.93-7.77 (m, 4H), 7.70 (dt, J=9.4, 2.1 Hz, 1H), 7.63 (td, J=7.3, 1.6 Hz, 2H), 7.53 (td, J=7.6, 3.2 Hz, 4H), 7.45-7.31 (m, 2H), 7.31-7.12 (m, 5H), 4.65 (dd, J=8.4, 5.2 Hz, 1H), 4.50 (dd, J=8.7, 5.4 Hz, 1H), 4.46 (t, J=5.7 Hz, 2H), 4.32 (dd, J=8.3, 5.8 Hz, 1H), 3.92 (d, J=16.7 Hz, 1H), 3.88 (s, 3H), 3.83 (d, J=16.7 Hz, 1H), 3.74 (t, J=5.7 Hz, 2H), 3.66-3.49 (m, 22H), 3.49-3.40 (m, 8H), 3.19 (dd, J=13.9, 5.2 Hz, 1H), 3.02 (dd, J=13.9, 8.4 Hz, 1H), 2.89 (dd, J=13.9, 5.4 Hz, 1H), 2.70 (dd, J=13.9, 8.7 Hz, 1H), 2.56-2.45 (m, 2H), 2.42 (t, J=7.5 Hz, 2H), 2.18-2.05 (m, 1H), 1.99 (s, 4H), 1.67-1.54 (m, 4H). $^{13}$C NMR (150 MHz, $CD_3OD$) δ 176.3, 174.5, 174.1, 173.7, 172.4, 171.4, 161.5 (d, J=11.9 Hz), 156.7, 150.4 (d, J=6.0 Hz), 138.2, 137.5 (d, J=1.5 Hz), 133.6 (d, J=2.9 Hz), 133.1 (d, J=10.7 Hz), 132.3 (d, J=110.7 Hz), 130.4, 129.7 (d, J=12.8 Hz), 129.4, 127.8, 124.7 (d, J=113.1 Hz), 122.1 (d, J=13.0 Hz), 118.5, 112.1, 71.7, 71.5, 71.5, 71.5, 71.5, 71.5, 71.5, 71.4, 71.1, 69.3, 56.3, 55.1, 54.7, 54.3, 43.6, 43.5, 38.3, 34.4, 32.7, 31.1, 29.7, 27.9, 27.2, 22.6. $^{31}$P NMR (162 MHz, $CD_3OD$) δ 28.8. HRMS (ESI+) m/z calcd. For $[C_{63}H_{84}N_5NaO_{19}PS]^+$: 1300.5111, found: 1300.5118.

Example III-12. Preparation of NGCF-$Q_{PEG}$ (6l)

6i

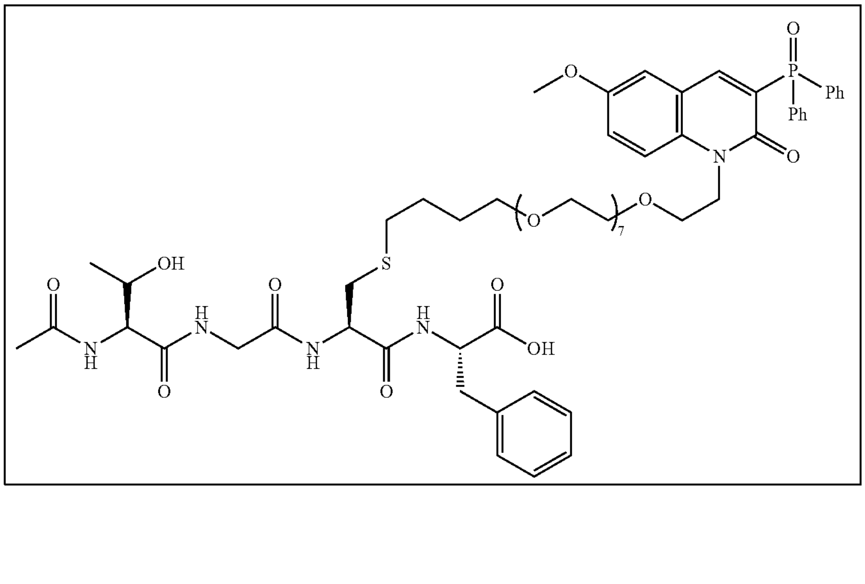

15.6 mg (62%) Compound 61 was obtained according to the above preparation method.

$^{1}$H NMR (600 MHz, $CD_3OD$) δ 8.58 (d, J=14.7 Hz, 1H), 7.85 (ddt, J=12.8, 7.0, 1.4 Hz, 4H), 7.70 (d, J=9.2 Hz, 1H), 7.65-7.59 (m, 2H), 7.56-7.50 (m, 4H), 7.39-7.33 (m, 2H), 7.28-7.18 (m, 4H), 7.18 (td, J=5.1, 4.7, 2.5 Hz, 1H), 4.67 (t, J=6.1 Hz, 1H), 4.64 (dd, J=8.0, 5.4 Hz, 1H), 4.52 (dd, J=9.3, 5.2 Hz, 1H), 4.45 (t, J=5.7 Hz, 2H), 3.96 (d, J=17.0 Hz, 1H), 3.88 (s, 3H), 3.79 (d, J=16.9 Hz, 1H), 3.74 (t, J=5.7 Hz, 2H), 3.62-3.49 (m, 22H), 3.49-3.41 (m, 8H), 3.18 (dd, J=13.9, 5.4 Hz, 1H), 3.03 (dd, J=13.9, 8.1 Hz, 1H), 2.90 (dd, J=13.9, 5.2 Hz, 1H), 2.83-2.71 (m, 3H), 2.57-2.47 (m, 2H), 2.00 (s, 3H), 1.64-1.54 (m, 4H). $^{13}$C NMR (150 MHz, $CD_3OD$) δ 174.7, 174.2, 174.0, 173.4, 172.5, 171.7, 161.5 (d, J=11.6 Hz), 156.7, 150.4 (d, J=6.1 Hz), 138.3, 137.5, 133.6 (d, J=2.9 Hz), 133.1 (d, J=10.8 Hz), 132.3 (d, J=110.8 Hz), 130.5, 129.7 (d, J=12.8 Hz), 129.4, 127.8, 124.8 (d, J=110.8 Hz), 124.1, 122.1 (d, J=13.1 Hz), 118.5, 112.1, 71.7, 71.7, 71.5, 71.5, 71.5, 71.5, 71.5, 71.4, 71.1, 69.3, 56.4, 55.2, 54.7, 51.6, 43.9, 43.5, 38.5, 37.7, 34.4, 32.7, 29.7, 27.3, 22.7. $^{31}$P NMR (162 MHz, $CD_3OD$) δ 29.4. HRMS (ESI+) m/z calcd. For $[C_{62}H_{83}N_6NaO_{18}PS]^+$: 1285.5114, found: 1285.5114.

Example III-13. Preparation of QGCF-$Q_{PEG}$ (6m)

6m

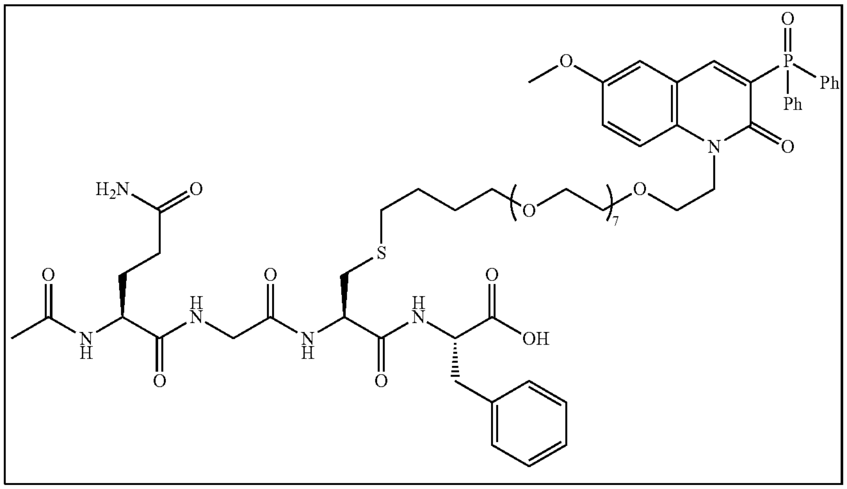

5.37 mg (60%) Compound 6m was obtained according to the above preparation method.

$^{1}H$ NMR (600 MHz, $CD_3OD$) δ 8.58 (d, J=14.7 Hz, 1H), 7.88-7.81 (m, 4H), 7.72 (d, J=9.2 Hz, 1H), 7.66-7.60 (m, 2H), 7.56-7.50 (m, 4H), 7.41-7.35 (m, 2H), 7.27-7.20 (m, 4H), 7.18 (td, J=6.8, 1.8 Hz, 1H), 4.62 (dd, J=8.3, 5.2 Hz, 1H), 4.53-4.44 (m, 3H), 4.28 (dd, J=7.9, 6.3 Hz, 1H), 3.92-3.84 (m, 2H) 3.89 (s, 3H), 3.75 (t, J=5.7 Hz, 2H), 3.61-3.50 (m, 22H), 3.49-3.40 (m, 8H), 3.19 (dd, J=13.9, 5.2 Hz, 1H), 3.01 (dd, J=13.9, 8.3 Hz, 1H), 2.89 (dd, J=14.0, 5.3 Hz, 1H), 2.70 (dd, J=14.0, 8.8 Hz, 1H), 2.57-2.46 (m, 2H), 2.37-2.28 (m, 2H), 2.13-2.04 (m, 1H), 2.01-1.94 (m, 1H), 1.99 (s, 3H), 1.65-1.54 (m, 4H). $^{13}C$ NMR (150 MHz, $CD_3OD$) δ 177.7, 174.5, 174.5, 173.6, 172.3, 171.5, 161.6 (d, J=12.0 Hz), 156.7, 150.4 (d, J=6.1 Hz), 138.4, 137.6, 133.6 (d, J=2.8 Hz), 133.1 (d, J=10.7 Hz), 132.3 (d, J=110.8 Hz), 130.5, 129.7 (d, J=12.8 Hz), 129.4, 127.8, 124.8 (d, J=110.9 Hz), 124.1, 122.1 (d, J=12.9 Hz), 118.5, 112.1, 71.7, 71.5, 71.5, 71.5, 71.5, 71.5, 71.5, 71.1, 69.4, 56.4, 55.4, 54.9, 54.4, 43.6, 43.6, 38.5, 34.5, 32.8, 32.5, 29.7, 28.5, 27.2, 22.6. $^{31}P$ NMR (162 MHz, $CD_3OD$) δ 29.4. HRMS (ESI+) m/z calcd. For $[C_{63}H_{85}N_6NaO_{18}PS]^+$: 1299.5271, found: 1299.5273.

Example III-14. Preparation of KGCF-$Q_{PEG}$ (6n)

14.7 mg (58%) of Compound 6n was obtained according to the above preparation method.

6n

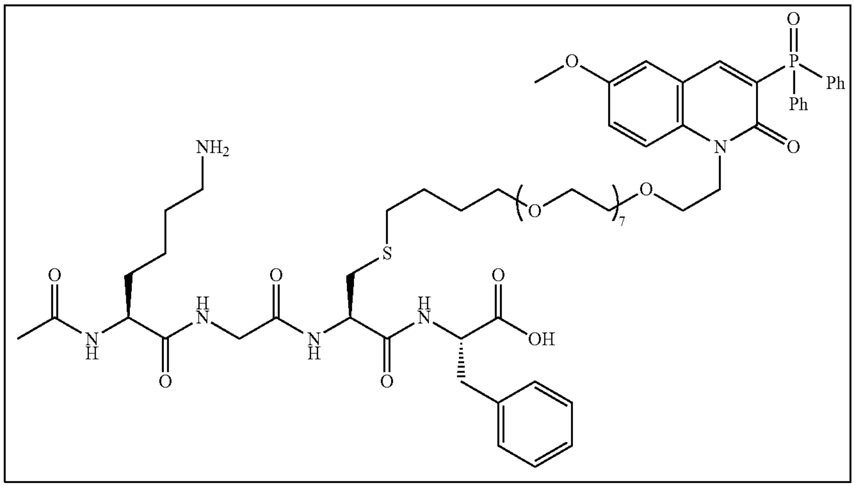

$^1H$ NMR (600 MHz, $CD_3OD$) δ 8.56 (d, J=14.8 Hz, 1H), 7.87-7.81 (m, 4H), 7.71 (d, J=9.3 Hz, 1H), 7.65-7.60 (m, 2H), 7.56-7.51 (m, 4H), 7.38 (dd, J=9.2, 3.0 Hz, 1H), 7.36 (d, J=2.9 Hz, 1H), 7.25-7.19 (m, 4H), 7.18-7.13 (m, 1H), 4.50-4.46 (m, 3H), 4.43 (dd, J=9.1, 4.8 Hz, 1H), 4.32-4.25 (m, 1H), 3.99-3.81 (m, 2H), 3.88 (s, 3H), 3.75 (t, J=5.7 Hz, 2H), 3.61-3.50 (m, 22H), 3.49-3.42 (m, 8H), 3.20 (dd, J=13.8, 5.0 Hz, 1H), 3.00 (dd, J=13.7, 7.6 Hz, 1H), 2.93-2.88 (m, 3H), 2.68 (dd, J=14.0, 9.1 Hz, 1H), 2.55-2.50 (m, 2H), 1.98 (s, 3H), 1.88-1.81 (m, 1H), 1.75-1.55 (m, 7H), 1.52-1.45 (m, 2H). $^{13}C$ NMR (150 MHz, $CD_3OD$) δ 176.7, 174.6, 173.4, 171.8, 171.6, 161.6 (d, J=11.6 Hz), 156.8, 150.4 (d, J=6.1 Hz), 139.1, 137.5, 133.6, 133.1 (d, J=10.6 Hz), 132.3 (d, J=110.7 Hz), 130.7, 129.7 (d, J=12.7 Hz), 129.2, 127.5, 124.8 (d, J=110.9 Hz), 124.2, 122.1 (d, J=13.0 Hz), 118.5, 112.2 (d, J=4.6 Hz), 71.8, 71.7, 71.5, 71.5, 71.4, 71.4, 71.4, 71.1, 69.3, 56.9, 56.4, 54.8, 54.8, 43.5, 43.4, 40.5, 39.0, 34.7, 32.9, 32.2, 29.7, 28.0, 27.3, 23.4, 22.6. $^{31}P$ NMR (162 MHz, $CD_3OD$) δ 29.4. HRMS (ESI+) m/z calcd. For $[C_{64}H_{90}N_6O_{17}PS]^+$: 1277.5815, found: 1277.5815.
Example III-15. Preparation of RGCF-$Q_{PEG}$ (6o)
6o
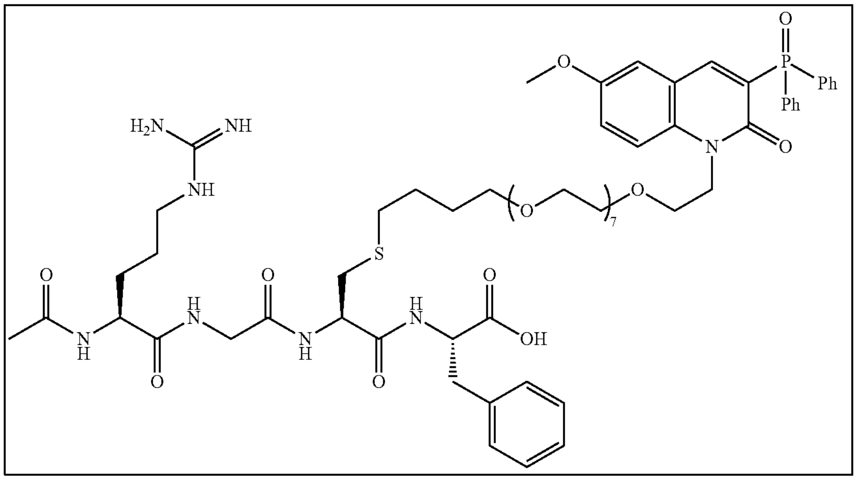

16.9 mg (65%) of Compound 6o was obtained according to the above preparation method.

$^1H$ NMR (600 MHz, $CD_3OD$) δ 8.58-8.51 (m, 1H), 7.88-7.80 (m, 4H), 7.73-7.68 (m, 1H), 7.66-7.60 (m, 2H), 7.56-7.50 (m, 4H), 7.39-7.36 (m, 1H), 7.36-7.34 (m, 1H), 7.23-7.18 (m, 4H), 7.17-7.12 (m, 1H), 4.47 (t, J=5.7 Hz, 2H), 4.43 (dd, J=7.1, 5.1 Hz, 1H), 4.41-4.38 (m, 1H), 4.32 (t, J=6.8 Hz, 1H), 3.96-3.85 (m, 2H), 3.88 (d, J=1.3 Hz, 3H), 3.75 (t, J=5.7 Hz, 2H), 3.62-3.50 (m, 22H), 3.49-3.41 (m, 8H), 3.20 (dd, J=13.7, 5.0 Hz, 1H), 3.16 (t, J=7.0 Hz, 2H), 3.01 (dd, J=13.6, 7.1 Hz, 1H), 2.92 (dd, J=13.9, 4.5 Hz, 1H), 2.65 (dd, J=13.9, 9.6 Hz, 1H), 2.56-2.45 (m, 2H), 1.98 (s, 3H), 1.89-1.82 (m, 1H), 1.76-1.69 (m, 1H), 1.69-1.56 (m, 6H). $^{13}C$ NMR (150 MHz, $CD_3OD$) δ 177.8, 174.4, 173.4, 171.7, 171.6, 161.6 (d, J=11.7 Hz), 158.6, 156.7, 150.4 (d, J=6.2 Hz), 139.4, 137.5, 133.6, 133.1 (d, J=10.6 Hz), 132.3 (d, J=110.6 Hz), 130.8, 129.7 (d, J=12.8 Hz), 129.1, 127.4, 124.8 (d, J=110.9 Hz), 124.2, 122.1 (d, J=12.9 Hz), 118.5, 112.2, 71.7, 71.7, 71.5, 71.5, 71.4, 71.4, 71.1, 69.3, 57.4, 56.4, 55.1, 54.5, 43.5, 43.5, 42.0, 39.1, 34.5, 32.8, 30.0, 29.7, 27.3, 25.8, 22.6. $^{31}P$ NMR (162 MHz, $CD_3OD$) δ 29.5. HRMS (ESI+) m/z calcd. For $[C_{64}H_{90}N_8O_{17}PS]^+$: 1305.5877, found: 1305.5878.

Example III-16. Preparation of WGCF-$Q_{PEG}$ (6p)

6p

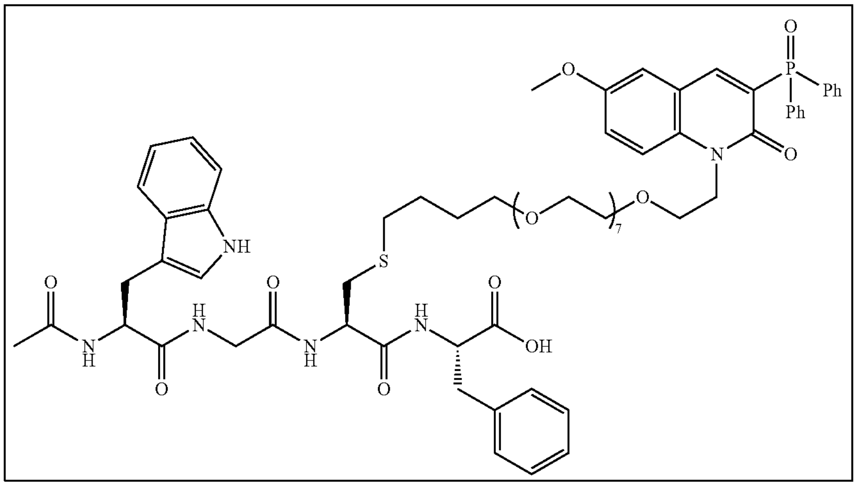

16.0 mg (60%) of Compound 6p was obtained according to the above preparation method.

$^{1}H$ NMR (600 MHz, $CD_3OD$) δ 8.58 (d, J=14.6 Hz, 1H), 7.89-7.80 (m, 4H), 7.72-7.66 (m, 1H), 7.65-7.59 (m, 2H), 7.57 (d, J=7.9 Hz, 1H), 7.56-7.49 (m, 4H), 7.39-7.33 (m, 2H), 7.31 (d, J=8.1 Hz, 1H), 7.28-7.19 (m, 4H), 7.17 (td, J=6.7, 2.0 Hz, 1H), 7.11 (s, 1H), 7.10-7.04 (m, 1H), 6.99 (t, J=7.5 Hz, 1H), 4.67-4.63 (m, 1H), 4.57 (t, J=7.1 Hz, 1H), 4.48 (dd, J=8.8, 5.4 Hz, 1H), 4.47-4.43 (m, 2H), 3.91-3.86 (m, 4H), 3.73 (t, J=5.7 Hz, 2H), 3.66 (d, J=16.7 Hz, 1H), 3.59-3.48 (m, 22H), 3.47-3.40 (m, 8H), 3.30-3.27 (m, 1H), 3.19 (dd, J=14.0, 5.2 Hz, 1H), 3.16-3.10 (m, 1H), 3.02 (dd, J=14.0, 8.4 Hz, 1H), 2.88 (dd, J=14.0, 5.4 Hz, 1H), 2.70 (dd, J=14.0, 8.8 Hz, 1H), 2.50 (td, J=6.9, 3.4 Hz, 2H), 1.92 (s, 3H), 1.65-1.51 (m, 4H). $^{13}C$ NMR (100 MHz, $CD_3OD$) δ 174.9, 172.4, 171.5, 156.7, 150.4 (d, J=5.9 Hz), 138.3, 138.0, 133.6 (d, J=2.8 Hz), 133.1 (d, J=10.8 Hz), 132.3 (d, J=111.0 Hz), 130.4, 129.7 (d, J=12.8 Hz), 129.4, 128.8, 127.8, 125.3, 124.5, 124.1, 122.4, 122.1 (d, J=12.8 Hz), 119.8, 119.3, 118.5, 112.3, 112.1, 111.0, 71.7, 71.5, 71.5, 71.5, 71.4, 71.1, 56.4, 56.3, 54.4, 43.7, 43.5, 38.4, 34.4, 32.8, 29.7, 28.6, 27.2, 22.6. $^{31}P$ NMR (162 MHz, $CD_3OD$) δ 28.8. HRMS (ESI+) m/z calcd. For $[C_{69}H_{87}N_6NaO_{17}PS]^+$: 1357.5478, found: 1357.5476.

Example III-17. Preparation of HGCF-$Q_{PEG}$ (6q)

6q

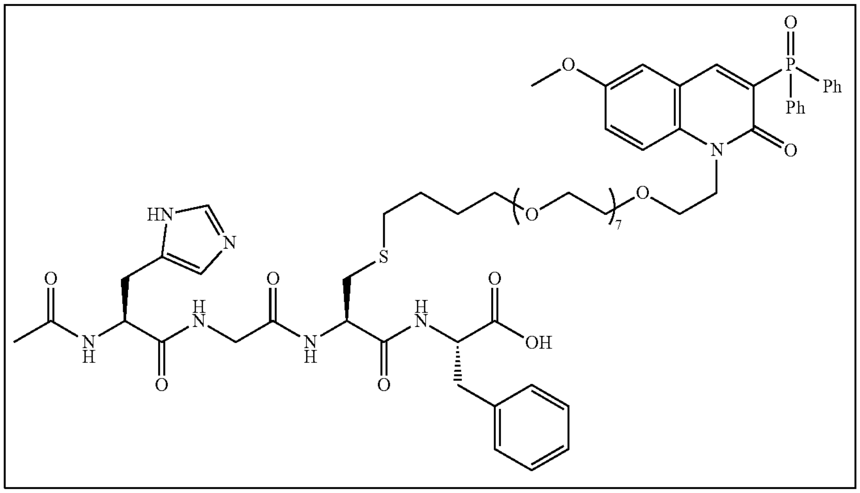

17.5 mg (68%) of Compound 6q was obtained according to the above preparation method.

$^{1}$H NMR (600 MHz, $CD_3OD$) δ 8.75 (d, J=1.5 Hz, 1H), 8.53 (d, J=14.8 Hz, 1H), 7.88-7.81 (m, 4H), 7.70 (d, J=9.3 Hz, 1H), 7.66-7.60 (m, 2H), 7.56-7.50 (m, 4H), 7.40-7.36 (m, 2H), 7.35 (d, J=2.9 Hz, 1H), 7.27-7.20 (m, 4H), 7.19-7.14 (m, 1H), 4.71 (t, J=6.5 Hz, 1H), 4.65 (dd, J=8.5, 5.2 Hz, 1H), 4.52 (dd, J=8.7, 5.2 Hz, 1H), 4.47 (t, J=5.7 Hz, 2H), 3.96-3.88 (m, 2H), 3.88 (s, 3H), 3.75 (t, J=5.7 Hz, 2H), 3.61-3.50 (m, 22H), 3.49-3.42 (m, 8H), 3.28 (dd, J=15.4, 6.1 Hz, 1H), 3.20 (dd, J=13.9, 5.1 Hz, 1H), 3.14 (dd, J=15.4, 6.9 Hz, 1H), 3.02 (dd, J=14.0, 8.5 Hz, 1H), 2.92 (dd, J=13.9, 5.2 Hz, 1H), 2.70 (dd, J=13.9, 8.8 Hz, 1H), 2.57-2.48 (m, 2H), 1.97 (s, 3H), 1.64-1.55 (m, 4H). $^{13}$C NMR (150 MHz, $CD_3OD$) δ 174.21, 173.41, 172.69, 172.37, 171.72, 161.61 (d, J=11.5 Hz), 156.74, 150.37 (d, J=6.3 Hz), 138.30, 137.49, 135.13, 133.62 (d, J=2.9 Hz), 133.07 (d, J=10.5 Hz), 132.22 (d, J=110.8 Hz), 130.80, 130.41, 129.72 (d, J=12.8 Hz), 129.45, 127.81, 124.73 (d, J=110.9 Hz), 124.16, 122.07 (d, J=13.1 Hz), 118.78, 118.44, 112.19, 71.71, 71.70, 71.48, 71.47, 71.45, 71.42, 71.40, 71.38, 71.09, 69.32, 56.35, 55.18, 54.47, 53.65, 43.51, 43.40, 38.30, 34.63, 32.88, 29.69, 28.09, 27.26, 22.62. $^{31}$P NMR (162 MHz, $CD_3OD$) δ 29.59. HRMS (ESI+) m/z calcd. For $[C_{64}H_{85}N_7O_{17}PS]^+$: 1286.5455, found: 1286.5461.

Example III-18. Preparation of YGCF-$Q_{PEG}$ (6r)

15.5 mg (59%) of Compound 6r was obtained according to the above preparation method.

$^{1}$H NMR (600 MHz, $CD_3OD$) δ 8.58 (d, J=14.7 Hz, 1H), 7.85 (ddd, J=12.8, 8.2, 1.4 Hz, 4H), 7.70 (d, J=9.2 Hz, 1H), 7.62 (td, J=7.4, 1.5 Hz, 2H), 7.53 (td, J=7.8, 2.9 Hz, 4H), 7.39-7.33 (m, 2H), 7.29-7.20 (m, 4H), 7.20-7.15 (m, 1H), 7.04 (d, J=8.5 Hz, 2H), 6.69 (d, J=8.5 Hz, 2H), 4.67-4.63 (m, 1H), 4.50 (dd, J=8.7, 5.4 Hz, 1H), 4.48-4.42 (m, 3H), 3.92 (d, J=16.7 Hz, 1H), 3.88 (s, 3H), 3.74 (t, J=5.7 Hz, 2H), 3.69 (d, J=16.7 Hz, 1H), 3.61-3.49 (m, 22H), 3.49-3.39 (m, 8H), 3.19 (dd, J=14.0, 5.2 Hz, 1H), 3.08-2.98 (m, 2H), 2.89 (dd, J=14.0, 5.4 Hz, 1H), 2.82 (dd, J=14.0, 8.6 Hz, 1H), 2.70 (dd, J=14.0, 8.7 Hz, 1H), 2.56-2.45 (m, 2H), 1.91 (s, 3H), 1.65-1.54 (m, 4H). $^{13}$C NMR (150 MHz, $CD_3OD$) δ 174.5, 174.2, 173.4, 172.4, 171.4, 161.5 (d, J=11.8 Hz), 157.3, 156.7, 150.4 (d, $J_{CP}$=6.1 Hz), 138.3, 137.6, 133.6 (d, J=2.9 Hz), 133.1 (d, J=10.6 Hz), 132.3 (d, J=110.7 Hz), 131.2, 130.5, 129.7 (d, J=13.0 Hz), 129.4, 129.0, 127.8, 124.7 (d, J=111.3 Hz), 124.1, 122.1 (d, J=12.8 Hz), 118.5, 116.2, 112.1, 71.8, 71.7, 71.6, 71.5, 71.5, 71.5, 71.5, 69.4, 57.1, 56.3, 55.2, 54.4, 43.6, 43.6, 38.4, 37.7, 34.5, 32.8, 29.7, 27.2, 22.6. $^{31}$P NMR (162 MHz, MeOD) δ 28.8. HRMS (ESI+) m/z calcd. For $[C_{67}H_{86}N_5NaO_{18}PS]^+$: 1334.5318, found 1334.5313.

6r

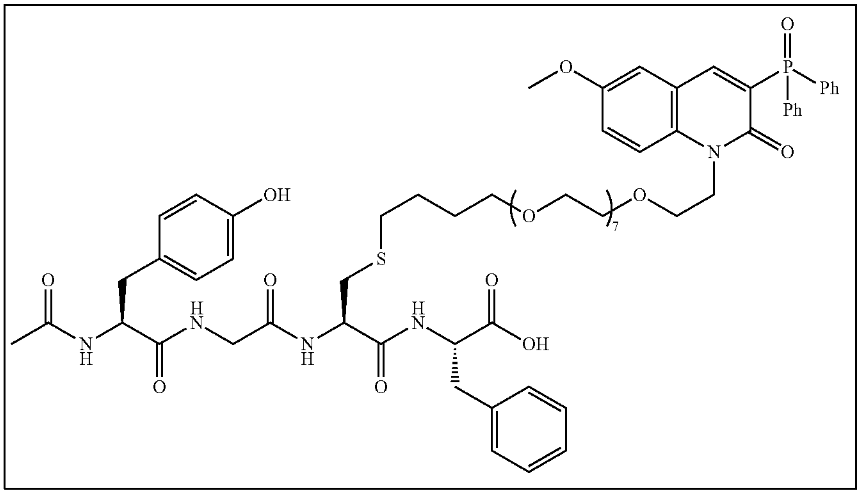

Example III-19. Preparation of CAFG-$Q_{PEG}$ (6s)

6s

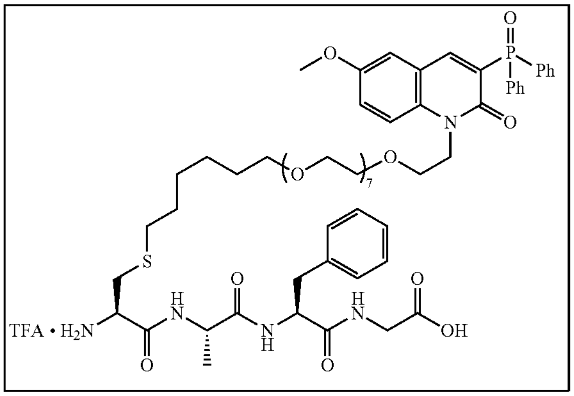

8.7 mg (75%) of Compound 6s was obtained according to the above preparation method.

$^1$H NMR (600 MHz, $CD_3OD$) δ 8.53 (d, J=14.8 Hz, 1H), 7.87-7.81 (m, 4H), 7.71 (d, J=9.3 Hz, 1H), 7.67-7.60 (m, 2H), 7.57-7.51 (m, 4H), 7.39 (dd, J=9.3, 2.9 Hz, 1H), 7.36 (d, J=2.9 Hz, 1H), 7.27-7.21 (m, 4H), 7.21-7.15 (m, 1H), 4.65 (dd, J=8.7, 5.5 Hz, 1H), 4.49 (t, J=5.6 Hz, 2H), 4.35 (q, J=7.1 Hz, 1H), 4.01 (dd, J=8.9, 5.4 Hz, 1H), 3.94-3.85 (m, 2H), 3.88 (s, 3H), 3.77 (t, J=5.6 Hz, 2H), 3.63-3.52 (m, 22H), 3.51-3.42 (m, 8H), 3.19 (dd, J=14.0, 5.5 Hz, 1H), 3.05 (dd, J=14.5, 5.4 Hz, 1H), 2.94 (dd, J=14.1, 8.7 Hz, 1H), 2.80 (dd, J=14.4, 8.9 Hz, 1H), 2.65-2.57 (m, 2H), 1.74-1.58 (m, 4H), 1.31 (d, J=7.2 Hz, 3H). $^{13}$C NMR (150 MHz, $CD_3OD$) δ 173.9, 173.5, 172.6, 168.9, 161.6 (d, J=11.2 Hz), 156.8, 150.4, 138.3, 137.5, 133.6, 133.1 (dd, J=10.7, 2.3 Hz), 132.2 (d, J=113.0 Hz), 130.4, 129.7 (d, J=12.7 Hz), 129.5, 127.8, 125.1 (d, J=110.9 Hz), 124.2, 122.1 (d, J=13.5 Hz), 118.4, 112.2, 71.8, 71.6, 71.4, 71.4, 71.3, 71.3, 71.3, 71.3, 71.2, 70.9, 69.3, 56.3, 55.7, 53.6, 50.8, 43.4, 41.8, 38.8, 33.9, 32.7, 29.2, 27.4, 18.1. $^{19}$F NMR (376 MHz, $CD_3OD$) 5-77.0. $^{31}$P NMR (162 MHz, $CD_3OD$) δ 29.5. HRMS (ESI+) m/z calcd. For $[C_{59}H_{80}N_5NaO_{16}PS]^+$: 1200.4951, found 1200.4949.

Example III-20. Preparation of AFGC-$Q_{PEG}$ (6t)

6t

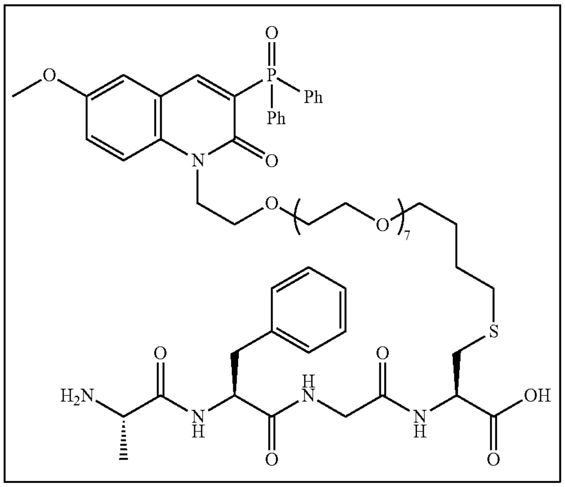

17.7 mg (71%) Compound 6t was obtained according to the above preparation method.

$^1$H NMR (600 MHz, DMSO-$d_6$) δ 11.68 (s, 1H), 8.99 (s, 1H), 8.70 (d, J=14.6 Hz, 1H), 8.65 (s, 1H), 7.81-7.75 (m, 4H), 7.64 (d, J=9.4 Hz, 1H), 7.62-7.56 (m, 3H), 7.55-7.47 (m, 5H), 7.35 (dd, J=9.3, 3.0 Hz, 1H), 7.28-7.14 (m, 5H), 4.38 (t, J=5.9 Hz, 2H), 4.30-4.24 (m, 1H), 4.13-4.07 (m, 1H), 3.95 (dd, J=16.8, 7.4 Hz, 1H), 3.82 (s, 3H), 3.63 (m, 3H), 3.51-3.40 (m, 25H), 3.40-3.30 (m, 8H), 3.13 (dd, J=14.0, 4.4 Hz, 1H), 2.97 (dd, J=13.9, 10.3 Hz, 1H), 2.90 (dd, J=13.3, 4.7 Hz, 1H), 2.72 (dd, J=13.3, 6.9 Hz, 1H), 2.52-2.43 (m, 2H), 1.58-1.42 (m, 4H), 1.20 (d, J=7.0 Hz, 3H). $^{13}$C NMR (150 MHz, DMSO-$d_6$) δ 172.4, 171.3, 170.8, 168.1, 159.4 (d, J=11.4 Hz), 154.3, 148.5, 138.3, 135.6, 132.4 (d, J=108.1 Hz), 131.8, 131.5 (d, J=10.3 Hz), 129.3, 128.3 (d, J=12.2 Hz), 128.1, 126.3, 124.6 (d, J=106.1 Hz), 122.1, 120.2 (d, J=12.9 Hz), 116.9, 111.6, 69.9, 69.9, 69.8, 69.8, 69.7, 69.7, 69.7, 69.4, 67.4, 55.7, 55.1, 54.1, 48.7, 42.3, 41.5, 36.0, 34.3, 31.5, 28.3, 25.8, 17.8. $^{31}$P NMR (162 MHz, DMSO-$d_6$) δ 23.7. HRMS (ESI+) m/z calcd. For $[C_{59}H_{81}N_5O_{16}PS]^+$: 1178.5131, found 1178.5123.

Example III-21. Preparation of Insulin β-fragment-$Q_{PEG}$ (6u)

6u

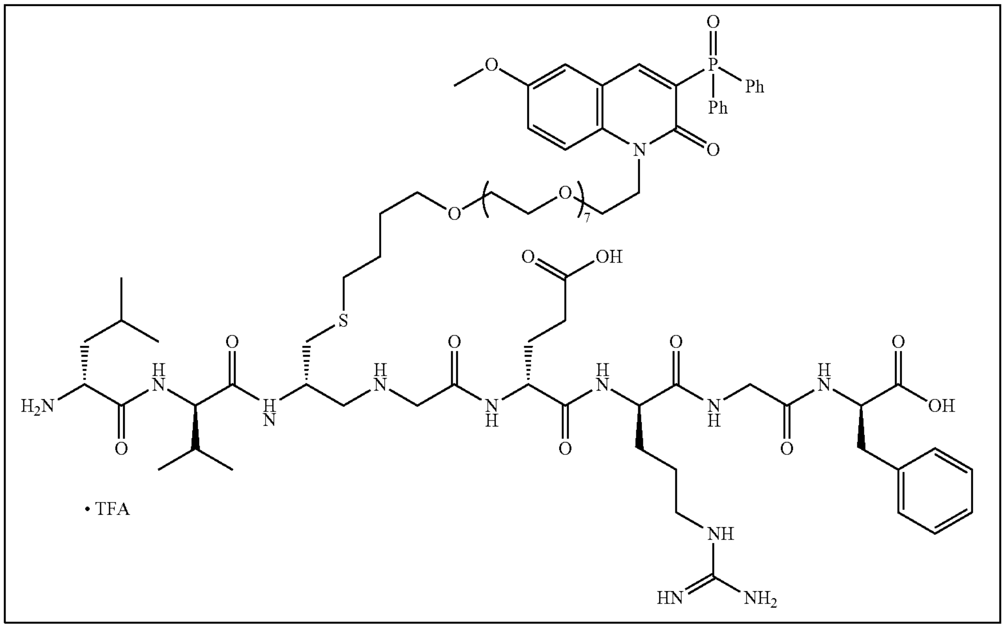

23.8 mg (67%) Compound 6u was obtained according to the above preparation method.

$^{1}$H NMR (600 MHz, $CD_3OD$) δ 8.51 (d, J=14.8 Hz, 1H), 7.87-7.81 (m, 4H), 7.70 (d, J=9.3 Hz, 1H), 7.66-7.60 (m, 2H), 7.57-7.50 (m, 4H), 7.37 (dd, J=9.3, 2.9 Hz, 1H), 7.34 (d, J=3.0 Hz, 1H), 7.28-7.23 (m, 2H), 7.23-7.17 (m, 3H), 4.66 (dd, J=8.2, 5.3 Hz, 1H), 4.47 (t, J=5.6 Hz, 2H), 4.41-4.32 (m, 3H), 4.28 (d, J=7.5 Hz, 1H), 4.05-4.00 (m, 1H), 3.97 (d, J=16.9 Hz, 1H), 3.90-3.86 (m, 5H), 3.83 (d, J=16.8 Hz, 1H), 3.75 (t, J=5.6 Hz, 2H), 3.62-3.50 (m, 22H), 3.50-3.43 (m, 8H), 3.23-3.13 (m, 3H), 3.00 (dd, J=13.9, 8.3 Hz, 1H), 2.94 (dd, J=13.7, 6.6 Hz, 1H), 2.82 (dd, J=13.7, 7.7 Hz, 1H), 2.62-2.53 (m, 2H), 2.47-2.38 (m, 2H), 2.19-1.99 (m, 3H), 1.96-1.87 (m, 1H), 1.80-1.58 (m, 10H), 1.02-0.91 (m, 12H). $^{13}$C NMR (150 MHz, $CD_3OD$) δ 176.6, 174.4, 173.9, 173.8, 173.3, 173.3, 171.8, 171.1, 170.9, 162.5 (q, J=34.5 Hz), 161.6 (d, J=11.7 Hz), 158.6, 156.7, 150.3 (d, J=6.2 Hz), 138.3, 137.5, 133.6 (d, J=2.7 Hz), 133.1 (d, J=10.5 Hz), 132.2 (d, J=110.8 Hz), 130.4, 129.7 (d, J=12.8 Hz), 129.5, 127.8, 124.7 (d, J=110.8 Hz), 124.1, 122.0 (d, J=12.8 Hz), 118.4, 118.0 (q, J=288.0 Hz), 112.2, 71.7, 71.7, 71.5, 71.4, 71.4, 71.4, 71.4, 71.4, 71.3, 71.0, 69.3, 60.4, 56.4, 55.2, 55.2, 54.6, 54.3, 52.9, 43.8, 43.5, 43.1, 41.9, 41.8, 38.4, 34.0, 33.0, 32.0, 31.3, 29.9, 29.6, 27.9, 27.2, 26.1, 25.3, 23.3, 22.1, 19.8, 18.9. $^{19}$F NMR (376 MHz, $CD_3OD$) δ-76.9. $^{31}$P NMR (162 MHz, $CD_3OD$) δ 29.5. HRMS (ESI+) m/z calcd. For $[C_{80}H_{118}N_{12}O_{22}PS]^+$: 1661.7936, found 1661.7941.

Example III-22. Preparation of Src Fragment-$Q_{PEG}$ (6v)

6v

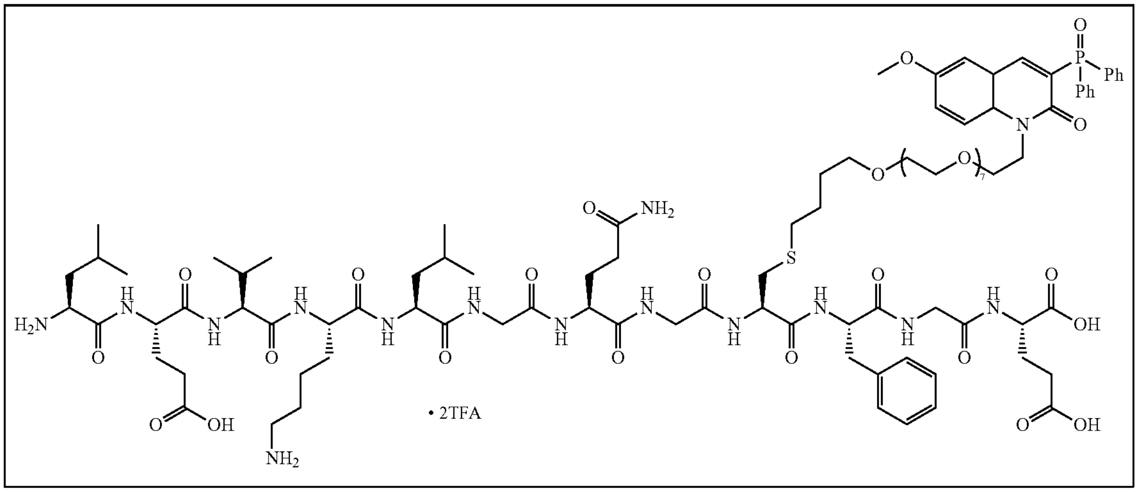

14.9 mg (52%) of Compound 6v was obtained according to the above preparation method.

$^1$H NMR (600 MHz, DMSO-$d_6$) δ 12.37 (br, 3H), 8.70 (d, J=14.6 Hz, 1H), 8.64 (d, J=7.6 Hz, 1H), 8.27 (d, J=7.9 Hz, 1H), 8.22 (t, J=5.7 Hz, 1H), 8.20-7.97 (m, 10H), 7.90 (d, J=8.6 Hz, 1H), 7.82-7.76 (m, 4H), 7.76-7.69 (m, 3H), 7.64 (d, J=9.4 Hz, 1H), 7.62-7.56 (m, 3H), 7.53-7.47 (m, 4H), 7.35 (dd, J=9.3, 3.0 Hz, 1H), 7.33-7.30 (m, 1H), 7.26-7.20 (m, 4H), 7.19-7.14 (m, 1H), 6.86-6.80 (m, 1H), 4.51-4.40 (m, 3H), 4.38 (t, J=5.9 Hz, 2H), 4.31-4.22 (m, 4H), 4.20 (dd, J=8.6, 6.4 Hz, 1H), 3.84-3.77 (m, 4H), 3.77-3.66 (m, 6H), 3.62 (t, J=5.8 Hz, 2H), 3.52-3.40 (m, 22H), 3.40-3.28 (m, 7H), 3.05 (dd, J=14.0, 4.6 Hz, 1H), 2.82 (dd, J=13.8, 9.4 Hz, 1H), 2.79-2.70 (m, 3H), 2.58-2.53 (m, 1H), 2.48-2.39 (m, 2H), 2.36-2.15 (m, 4H), 2.10 (t, J=8.0 Hz, 2H), 2.02-1.83 (m, 4H), 1.83-1.68 (m, 3H), 1.68-1.57 (m, 3H), 1.57-1.38 (m, 11H), 1.36-1.25 (m, 2H), 0.90-0.75 (m, 18H). $^{13}$C NMR (150 MHz, DMSO-$d_6$) δ 174.1, 174.0, 173.8, 173.2, 172.4, 171.5, 171.5, 171.0, 170.7, 170.5, 170.3, 168.9, 168.7, 168.7, 168.7, 159.4 (d, J=11.2 Hz), 158.2 (q, J=32.3 Hz), 154.4, 148.5, 137.7, 135.6, 132.7, 131.9 (d, J=12.8 Hz), 131.5 (d, J=10.4 Hz), 129.3, 128.1, 126.3, 124.6 (d, J=106.2 Hz), 122.1, 120.2 (d, J=12.7 Hz), 116.9, 116.9 (q, J=296.8 Hz) 111.6, 69.9, 69.9, 69.8, 69.8, 69.7, 69.7, 69.5, 67.4, 57.2, 55.7, 54.2, 52.4, 52.3, 52.2, 51.9, 51.2, 51.1, 50.8, 41.9, 41.7, 41.7, 41.5, 40.8, 40.3, 38.7, 37.3, 33.6, 31.4, 31.3, 31.1, 30.8, 30.3, 30.0, 28.3, 28.0, 27.6, 26.7, 26.5, 25.7, 24.1, 23.5, 23.1, 22.6, 22.3, 22.1, 21.5, 19.1, 17.8. $^{19}$F NMR (376 MHz, DMSO-$d_6$) δ−74.1. $^{31}$P NMR (162 MHz, DMSO-$d_6$) δ 23.7. HRMS (ESI+) m/z calcd. For $[C_{98}H_{146}N_{15}Na_3O_{29}PS]^{3+}$: 709.9860, found 709.9867.

Example III-23. Preparation of Oxytocin-($Q_{PEG}$)$_2$ (8)

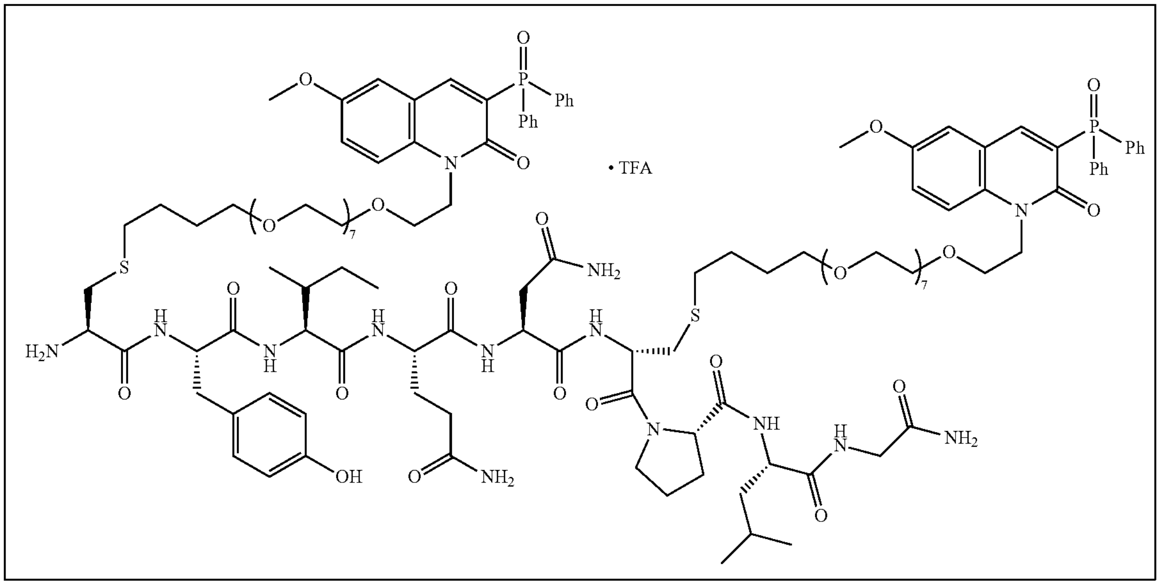

8

A pH 7.5 phosphate buffer (PB, 20 mM) or a sodium acetate buffer (pH 3.5, 20 mM) and 10% v/v DMF were put into a test tube, and a degassing process was performed according to Freeze-pump-thaw. Disulfide 7 (7a and 7b, 6.7 mM; 7c, 2 mM), $Q_{PEG}$ (2 equiv.), and tris(2-chloroethyl) phosphate (TCEP, 1 equiv.) were added to a buffer solution under a nitrogen atmosphere, and the mixture was stirred for 2 hours without light irradiation and for 3 hours with blue light source irradiation (440 nm, 8.5 W, Kessil blue LED) at room temperature to proceed with the reaction. After the reaction was completed, 0.5 mL (DABCO, 2 equiv.) of a 1,4-diazabicyclo[2.2.2]octane stock solution was added, the solvent was removed by a rotary evaporator, and purification was performed with RP-HPLC to prepare 12.8 mg (60%) of Compound 8.

$^1$H NMR (600 MHz, $CD_3OD$) δ 8.60-8.51 (m, 2H), 7.88-7.82 (m, 8H), 7.74-7.67 (m, 2H), 7.66-7.60 (m, 4H), 7.57-7.50 (m, 8H), 7.40-7.33 (m, 4H), 7.08 (d, J=8.5 Hz, 2H), 6.68 (d, J=8.5 Hz, 2H), 4.81 (t, J=7.2 Hz, 1H), 4.70 (td, J=8.3, 7.2, 5.1 Hz, 2H), 4.47 (t, J=5.7 Hz, 4H), 4.39 (dd, J=8.6, 4.5 Hz, 1H), 4.33-4.27 (m, 1H), 4.22 (dd, J=8.1, 6.0 Hz, 1H), 4.16-4.10 (m, 1H), 4.05-3.98 (m, 1H), 3.92 (d, J=17.0 Hz, 1H), 3.88 (s, 6H), 3.84-3.76 (m, 1H), 3.77-3.71 (m, 5H), 3.74-3.67 (m, 1H), 3.62-3.49 (m, 44H), 3.50-3.40 (m, 16H), 3.17-3.07 (m, 2H), 3.00 (dd, J=13.7, 6.8 Hz, 1H), 2.86-2.71 (m, 5H), 2.61 (q, J=6.5 Hz, 4H), 2.40-2.26 (m, 2H), 2.21 (dt, J=11.2, 7.1 Hz, 1H), 2.08 (dq, J=13.4, 6.7 Hz, 1H), 2.04-1.93 (m, 4H), 1.82 (s, 1H), 1.72-1.59 (m, 11H), 1.58-1.49 (m, 1H), 1.23-1.12 (m, 1H), 0.98-0.85 (m, 12H). $^{13}$C NMR (100 MHz, $CD_3OD$) δ 177.7, 174.9, 174.7, 174.6, 174.3, 173.8, 173.7, 173.4, 172.7, 171.9, 169.1, 161.6 (d, J=11.6 Hz), 157.4, 156.7, 150.4 (d, J=6.1 Hz), 137.5, 133.6, 133.1 (d, J=10.7 Hz), 132.3 (d, J=111.0 Hz), 131.3, 129.7 (d, J=12.9 Hz), 129.6, 128.8, 124.8 (d, J=110.6 Hz), 124.2, 122.1 (d, J=13.1 Hz), 118.4 (d, J=2.5 Hz), 116.4, 112.2, 71.8, 71.8, 71.7, 71.7, 71.5, 71.5, 71.4, 71.4, 71.4, 71.3, 71.3, 71.1, 71.0, 69.3, 69.3, 62.5, 60.0, 56.6, 56.4, 55.1, 53.7, 53.6, 52.7, 51.9, 43.5, 43.4, 43.4, 40.9, 37.9, 37.7, 34.1, 33.3, 32.9, 32.6, 30.4, 29.8, 29.2, 28.3, 27.5, 27.4, 26.3, 26.0, 23.6, 21.9, 16.2, 11.6. $^{19}$F NMR (376 MHz, $CD_3OD$) 5-77.0. $^{31}$P NMR (162 MHz, $CD_3OD$) δ 28.7. HRMS (ESI+) m/z calcd. For $[C_{127}H_{180}N_{14}Na_2O_{34}P_2S_2]^{2+}$: 1309.0761, found 1309.0762.

[Example IV] Preparation of Quinolinone Derivative $Q_{CAT}$ as Photocatalyst

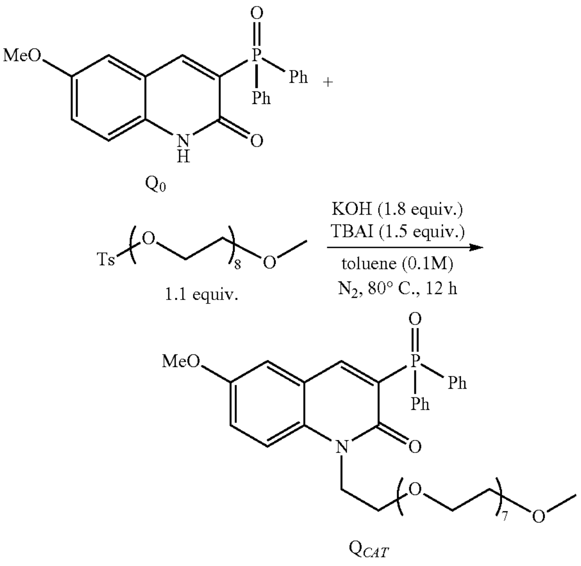

$Q_0$ (206 mg, 0.55 mmol), tosylate (1.1 equiv.), potassium hydroxide (1.8 equiv.), and tetra-n-butylammonium bromide (1.5 equiv.) were added to a round bottom flask dried with an oven, and the flask was filled with $N_2$. Toluene (5.5 ml)

was injected thereinto with a syringe at 0° C., and stirring was performed at 80° C. for 12 hours. After the reaction was completed, the solvent was removed with a rotary evaporator, and distilled water was added. Thereafter, extraction with $CH_2Cl_2$ (50 ml×3) was performed, the solvent was removed, and the residues were purified with flash chromatography of a silica phase ($MeOH/CH_2Cl_2$=1:30), thereby preparing $Q_{CAT}$ (140 mg, 34%).

$Q_{CAT}$

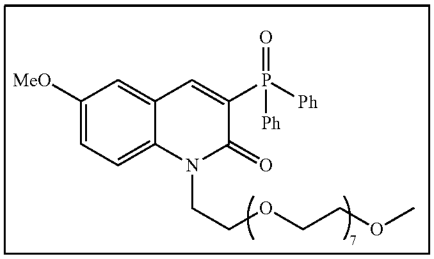

3-(diphenylphosphoryl)-6-methoxy-1-(2,5,8,11,14,17,20,23-octaoxapentacosan-25-yl)quinolin-2(1H)-one $^1H$ NMR (400 MHz, $CD_3OD$) δ 8.58 (d, J=14.7 Hz, 1H), 7.81-7.89 (m, 4H), 7.66-7.57 (m, 3H), 7.45-7.55 (m, 4H), 7.26-7.34 (m, 2H), 4.41 (t, J=5.7 Hz, 2H), 3.84 (s, 3H), 3.72 (t, J=5.6 Hz, 2H), 3.63-3.40 (m, 28H), 3.32 (s, 3H). $^{13}C$ NMR (100 MHz, $CD_3OD$) δ 161.4 (d, J=12.0 Hz), 156.6, 150.3 (d, J=5.9 Hz), 137.5 (d, J=1.5 Hz), 133.5 (d, J=2.9 Hz), 133.1 (d, J=10.7 Hz), 132.3 (d, J=110.7 Hz), 129.6 (d, J=12.8 Hz), 124.8 (d, J=110.6 Hz), 122.0 (d, J=12.9 Hz), 118.4, 112.0, 72.9, 71.7, 71.5, 71.5, 71.5, 71.5, 71.5, 71.4, 71.3, 69.3, 59.1, 56.3, 43.5. $^{31}P$ NMR (162 MHz, $CD_3OD$) δ 29.1. HRMS (ESI+) m/z calcd. For $[C_{39}H_{52}NNaO_{11}P]^+$: 764.3170, found: 764.3178. IR: 2865, 1634, 1564, 1436, 1235, 1098. MP: 88° C.

[Example V] Cysteine-Selective Conjugation Reaction of Biomolecule According to Photocatalysis of $Q_{CAT}$ A pH 7.5 phosphate buffer (PB, 20 mM) or a sodium acetate buffer (pH 3.5, 20 mM) and 10% v/v DMF were put into a test tube, and a degassing process was performed according to Freeze-pump-thaw. Tetramer peptide (10 mM), alkene substrates 9a to 9d (1.1 equiv.), and a photocatalyst $Q_{CAT}$ (5 mol % or 10 mol %) were added to the buffer under a nitrogen atmosphere, and the mixture was irradiated with a blue light source (440 nm, 8.5 W, Kessil blue LED) at room temperature and stirred to proceed with the reaction. After the reaction was completed, the solvent was removed with a rotary evaporator, and separation and purification with RP-HPLC were performed to prepare peptide conjugates 10a to 10d.

Compounds 9a to 9c corresponding to an alkene substrate were able to be obtained by the following Preparation Examples 2-1 to 2-3, and Compound 9d (CAS: 2595-07-5) was purchased from a reagent manufacturer (Astatech Pharmaceutical Co., Ltd., China) and was used without additional purification.

[Preparation Example 2-1] Preparation of Compound 9a

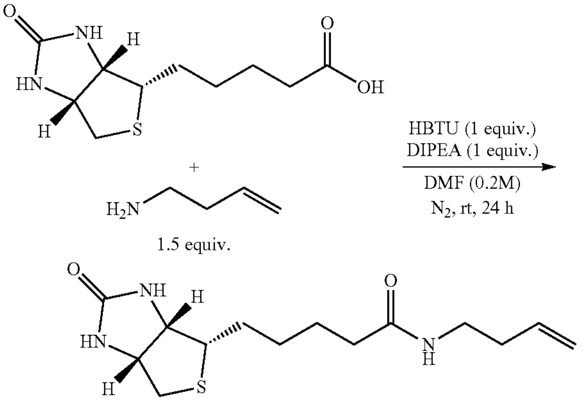

9a

Biotin (244 mg, 1.0 mmol) and 2-(1H-benzotriazol-1-yl)-1,1,3,3-tetramethyluronium hexafluorophosphate (HBTU) (1 equiv.) were put into a round bottom flask, the flask was filled with $N_2$, and DMF (5 ml), N,N-diisopropylethylamine (1 equiv.), and 3-buten-1-amine (1.5 equiv.) were injected into the flask with a syringe at 0° C. Thereafter, the flask was warmed up and stirred at room temperature for 24 hours to proceed with the reaction, and when the reaction was completed, the solvent was removed with a rotary evaporator, and distilled water was added. Thereafter, extraction with $CH_2Cl_2$ (50 ml×3) was performed, the solvent was removed, and the residues were recrystallized twice with MeOH (2 ml) and $Et_2O$ (200 ml) at −20° C. to prepare Compound 9a (296 mg, 100%).

[Preparation Example 2-2] Preparation of Compound 9b

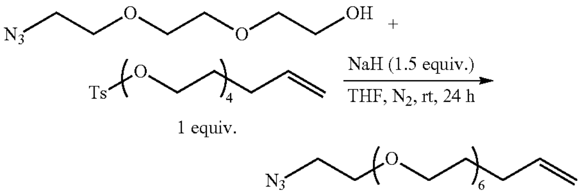

9b 2-(2-(2-azidoethoxy)ethoxy)ethan-1-ol (88 mg, 0.5 mmol) and sodium hydroxide (1.5 equiv.) were put into a round bottom flask, the flask was filled with $N_2$, and then THF (6 ml) and tosylate (1.0 equiv.) were injected into flask with a syringe at 0° C. After warming up the flask, stirring was performed at room temperature for 24 hours to proceed with the reaction, and after the reaction was completed, distilled water was added at 0° C., and THF was removed with a rotary evaporator. A water phase layer was extracted with $CH_2Cl_2$ (25 ml×3), and an organic layer was removed with a rotary evaporator. Thereafter, purification with flash chromatography of a silica phase ($MeOH/CH_2Cl_2$=1:30) was performed to prepare Compound 9b (110 mg, 61%).

[Preparation Example 2-3] Preparation of Compound 9c

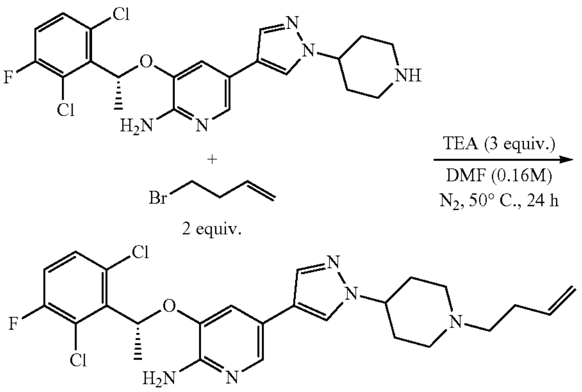

9c

Crizotinib (215 mg, 0.48 mmol) was put into a round flask, and the flask was filled with $N_2$. Thereafter, DMF (3 ml), triethylamine (3 equiv.), and 4-bromo-1-butene (2 equiv.) were injected into the flask with a syringe at 0° C. The flask was warmed up, stirring was performed at 50° C. for 24 hours to proceed with the reaction, and after the reaction was completed, the solvent was removed with a rotary evaporator. The reaction mixture was purified with flash chromatography of a silica phase ($MeOH/CH_2Cl_2$=1:10) to prepare Compound 9c (150 mg, 62%).

Example V-1. Preparation of AGCF-Biotin (10a)

10a

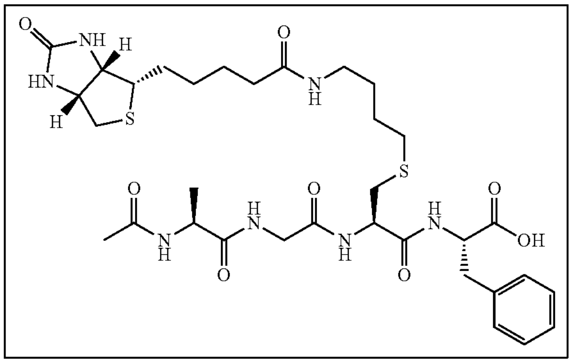

Compound 10a (10.5 mg, 71%) was obtained according to the preparation method of Example V.

$^1$H NMR (600 MHz, DMSO-$d_6$) δ 12.71 (br, 1H), 8.27 (d, J=7.9 Hz, 1H), 8.15-8.09 (m, 2H), 7.94 (d, J=8.4 Hz, 1H), 7.75 (t, J=5.6 Hz, 1H), 7.31-7.15 (m, 5H), 6.42 (s, 1H), 6.36 (br, 1H), 4.46-4.38 (m, 2H), 4.30 (dd, J=7.7, 5.0 Hz, 1H), 4.26-4.19 (m, 1H), 4.12 (dd, J=7.8, 4.4 Hz, 1H), 3.76-3.65 (m, 2H), 3.11-2.99 (m, 4H), 2.91 (dd, J=13.9, 8.7 Hz, 1H), 2.82 (dd, J=12.5, 5.1 Hz, 1H), 2.77 (dd, J=13.7, 4.8 Hz, 1H), 2.63-2.55 (m, 2H), 2.49-2.44 (m, 2H), 2.04 (t, J=7.4 Hz, 2H), 1.84 (s, 3H), 1.65-1.56 (m, 1H), 1.55-1.37 (m, 7H), 1.36-1.24 (m, 2H), 1.20 (d, J=7.1 Hz, 3H). $^{13}$C NMR (150 MHz, DMSO-$d_6$) δ 172.8, 172.5, 171.9, 170.1, 169.4, 168.6, 162.7, 137.4, 129.1, 128.2, 126.4, 61.0, 59.2, 55.4, 53.6, 52.3, 48.5, 41.9, 39.8, 37.9, 36.6, 35.2, 33.6, 31.1, 28.4, 28.2, 28.0, 26.4, 25.3, 22.5, 17.9. HRMS (ESI+) m/z calcd. For $[C_{33}H_{49}N_7NaO_8S2]^+$: 758.2976, found 758.2981.

Example V-2. Preparation of QGCF-azide (10b)

10b

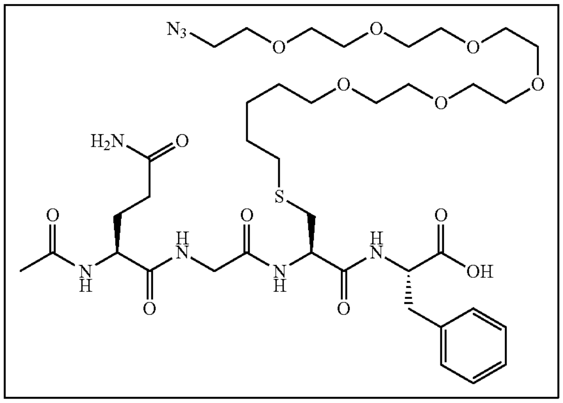

Compound 10b (7.9 mg, 50%) was obtained according to the preparation method of Example V.

$^1$H NMR (600 MHz, $CD_3OD$) δ 7.29-7.22 (m, 4H), 7.21-7.17 (m, 1H), 4.63 (dd, J=8.4, 5.2 Hz, 1H), 4.49 (dd, J=8.9, 5.3 Hz, 1H), 4.28 (t, J=7.1 Hz, 1H), 3.91 (d, J=16.8 Hz, 1H), 3.86 (d, J=16.7 Hz, 1H), 3.69-3.60 (m, 20H), 3.60-3.55 (m, 2H), 3.50-3.45 (m, 2H), 3.38 (t, J=5.0 Hz, 2H), 3.20 (dd, J=14.0, 5.2 Hz, 1H), 3.02 (dd, J=13.9, 8.4 Hz, 1H), 2.89 (dd, J=13.9, 5.2 Hz, 1H), 2.71 (dd, J=13.9, 8.9 Hz, 1H), 2.54-2.48 (m, 2H), 2.33 (t, J=7.5 Hz, 2H), 2.14-2.05 (m, 1H), 2.04-1.92 (m, 4H), 1.62-1.53 (m, 4H), 1.47-1.40 (m, 2H). $^{13}$C NMR (150 MHz, $CD_3OD$) δ 177.7, 174.5, 174.5, 173.6, 172.4, 171.5, 138.4, 130.5, 129.4, 127.8, 72.2, 71.6, 71.5, 71.1, 71.1, 55.4, 54.9, 54.4, 51.8, 43.6, 38.4, 34.5, 32.9, 32.5, 30.4, 30.2, 28.5, 26.4, 22.6. HRMS (ESI+) m/z calcd. For $[C_{38}H_{62}N_8Na_2O_{13}S]^{2+}$: 458.1971, found 458.1978.

Example V-3. Preparation of AGCF-Crizotinib (10c)

10c

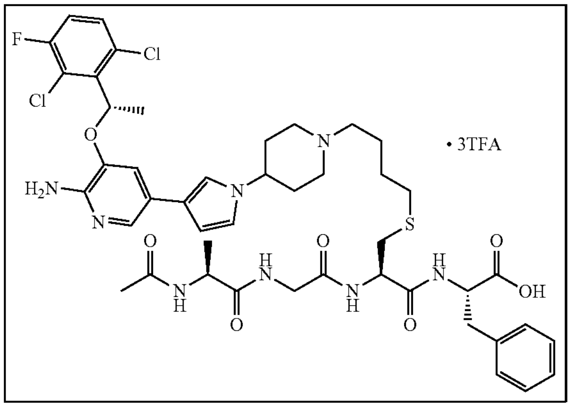

Compound 10c (19.3 mg, 75%) was obtained according to the preparation method of Example V.

$^1$H NMR (600 MHz, $CD_3OD$) δ 7.96 (s, 1H), 7.68 (s, 1H), 7.62 (d, J=1.8 Hz, 1H), 7.50 (dd, J=8.9, 4.8 Hz, 1H), 7.32-7.22 (m, 5H), 7.21-7.17 (m, 1H), 7.15 (d, J=1.7 Hz, 1H), 6.34 (q, J=6.7 Hz, 1H), 4.66 (dd, J=8.6, 5.1 Hz, 1H), 4.53 (dd, J=8.9, 5.3 Hz, 1H), 4.25 (q, J=7.1 Hz, 1H), 3.92 (d, J=16.8 Hz, 1H), 3.84 (d, J=16.8 Hz, 1H), 3.80-3.66 (m, 2H), 3.28-3.11 (m, 5H), 3.02 (dd, J=14.0, 8.6 Hz, 1H), 2.93 (dd, J=14.1, 5.3 Hz, 1H), 2.74 (dd, J=14.1, 8.9 Hz, 1H), 2.64-2.54 (m, 2H), 2.44-2.30 (m, 4H), 1.98 (s, 3H), 1.95 (d, J=6.7 Hz, 3H), 1.90-1.82 (m, 2H), 1.71-1.60 (m, 2H), 1.37 (d, J=7.2 Hz, 3H). $^{13}$C NMR (150 MHz, $CD_3OD$) δ 176.1, 174.2, 173.6, 172.4, 171.7, 162.8 (q, J=37.5) 159.9, 158.2, 148.4, 143.1, 138.3, 137.5, 136.6, 131.9, 130.4, 130.4 (d, J=3.6 Hz), 129.5, 127.8, 126.9, 123.0 (d, J=19.6 Hz), 122.7, 119.6 (d, J=7.5 Hz), 118.8 (d, J=23.4 Hz), 118.0 (q, J=304.5), 75.7, 57.6, 57.3, 55.2, 54.4, 52.7, 51.3, 43.7, 38.3, 34.5, 32.0, 30.8, 27.2, 24.0, 22.6, 19.0, 17.5. $^{19}$F NMR (376 MHz, $CD_3OD$) δ-77.0, −113.9. HRMS (ESI+) m/z calcd. For $[C_{44}H_{55}FN_9NaO_7S]^{2+}$: 482.6596, found 482.6595.

Example V-4. Preparation of MGCF-Pyranoside (10d)

10d

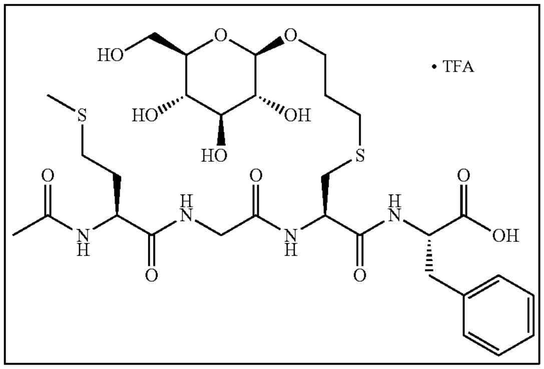

Compound 10d (11.0 mg, 66%) was obtained according to the preparation method of Example V.

$^1$H NMR (400 MHz, DMSO-$d_6$) δ 12.68 (br, 1H) 8.31 (d, J=7.9 Hz, 1H), 8.16 (t, J=5.7 Hz, 1H), 8.11 (d, J=7.6 Hz, 1H), 7.98 (d, J=8.4 Hz, 1H), 7.31-7.11 (m, 5H), 5.12-4.13 (m, 7H), 4.09-4.01 (m, 1H), 3.83-3.72 (m, 1H), 3.72 (d, J=5.7 Hz, 2H), 3.66-3.59 (m, 1H), 3.57-3.42 (m, 3H), 3.35-3.23 (m, 3H), 3.05 (dd, J=13.9, 5.3 Hz, 1H), 2.91 (dd, J=13.9, 8.7 Hz, 1H), 2.78 (dd, J=13.7, 4.9 Hz, 1H), 2.61-2.50 (m, 3H), 2.48-2.38 (m, 2H), 2.03 (s, 3H), 1.97-1.63 (m, 7H). $^{13}$C NMR (150 MHz, DMSO-$d_6$) δ 172.6, 171.8, 170.2, 169.7, 168.6, 137.4, 129.2, 128.3, 126.5, 103.5, 75.2, 73.4, 70.6, 68.2, 67.2, 60.4, 53.6, 52.2, 52.1, 41.8, 36.6, 33.6, 31.6, 29.6, 29.4, 28.0, 22.6, 14.6. $^{19}$F NMR (376 MHz, DMSO-$d_6$) 5-73.6. HRMS (ESI+) m/z calcd. For $[C_{30}H_{46}N_4NaO_{12}S_2]^+$: 741.2446, found: 741.2439.

[Experimental Example 1] Evaluation of Functional Group Resistance of Cysteine Selective Bond In order to evaluate the functional group resistance of a cysteine-selective bond at a protein level, it was confirmed whether the conjugate of the quinolinone derivative compound was produced for ubiquitin K63C (Ub K63C) and bovine serum albumin (BSA). $Q_{PEG}$ (5 mM) and Ub K63C (50 μM) or bovine serum albumin were put into a phosphate buffer containing 10% v/v of pH 7.5 DMSO and mixed, the mixture was irradiated with blue light (440 nm, 8.5 W) for 6 hours to directly bind to a cysteine residue, and the results were confirmed by LCMS. For confirming a binding site, an ESI-MS spectroscopy according to peptide mapping was used.

Figure 3:
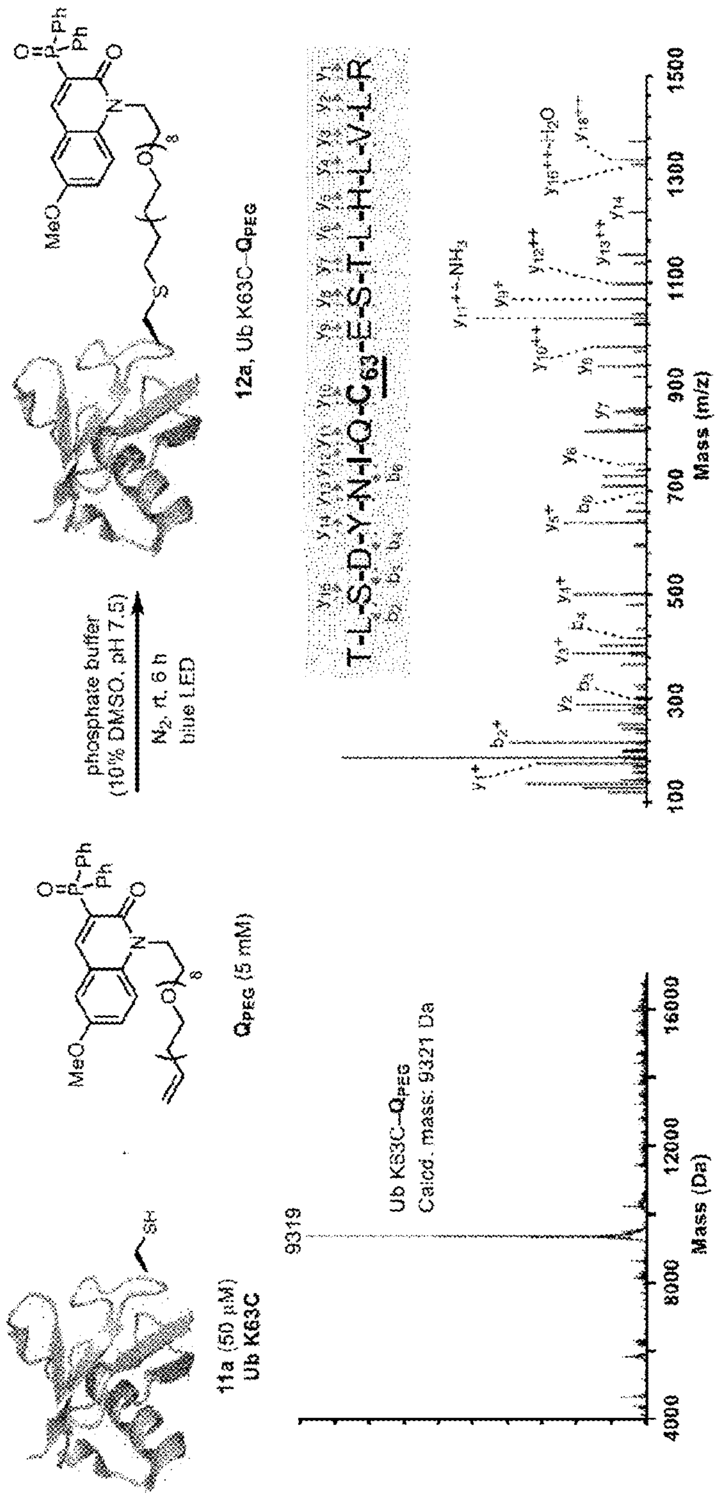
FIG. 3 confirms the results of a cysteine-selective conjugation reaction of ubiquitin protein (Ub K63C) and $Q_{PEG}$— by mass analysis.
Figure 4:
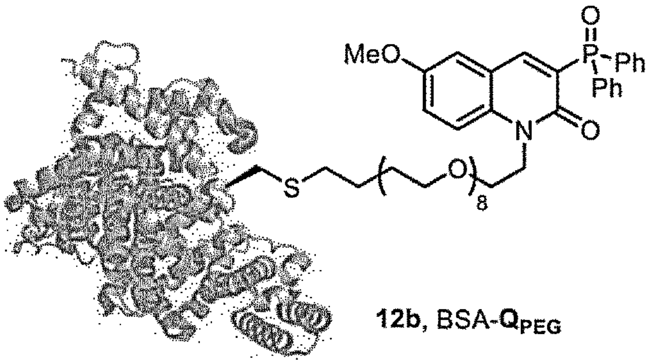
FIG. 4 confirms the results of a cysteine-selective conjugation reaction of bovine serum albumin (BSA) and $Q_{PEG}$— by mass analysis.
Figure 4:
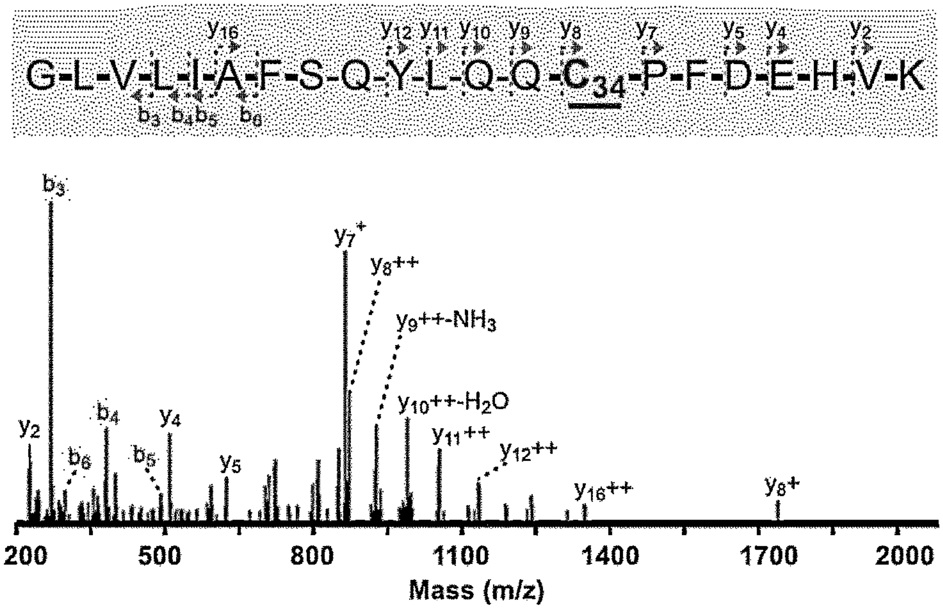
Figure 5:
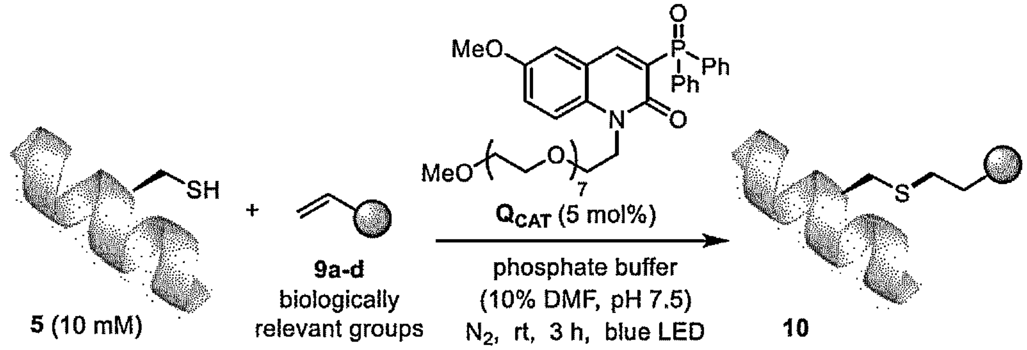
FIG. 5 shows a schematic diagram of a cysteine-selective conjugation reaction by photocatalysis of $Q_{CAT}$ according to the present disclosure.
Figure 6:
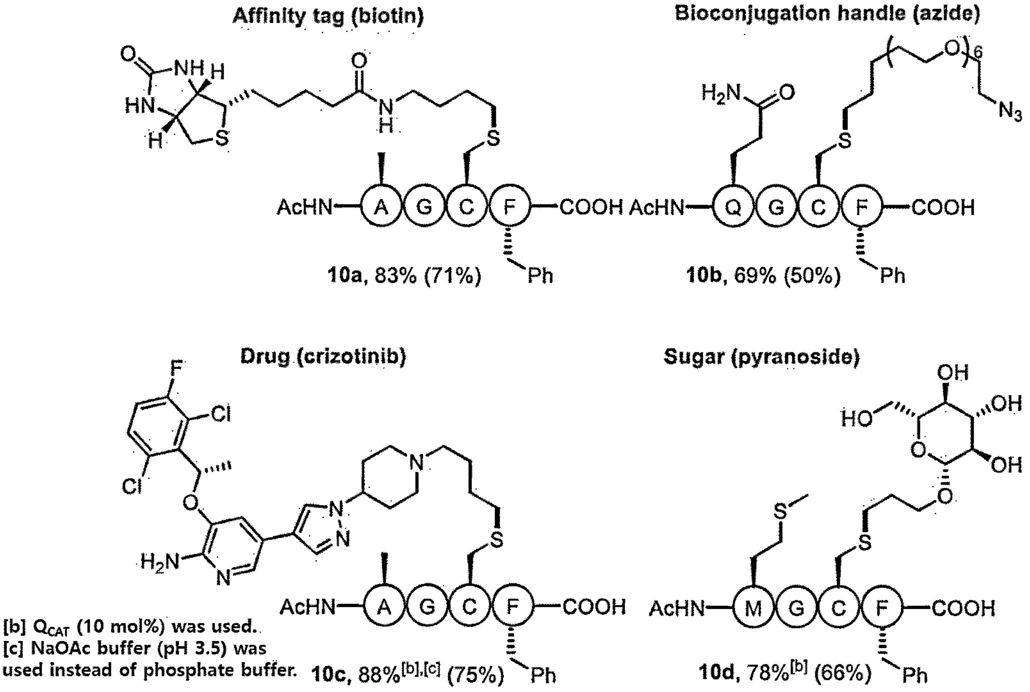
FIG. 6 shows a cysteine-selective conjugation reaction of various biomolecules by photocatalysis of $Q_{CAT}$ according to the present disclosure.
Figure 7:
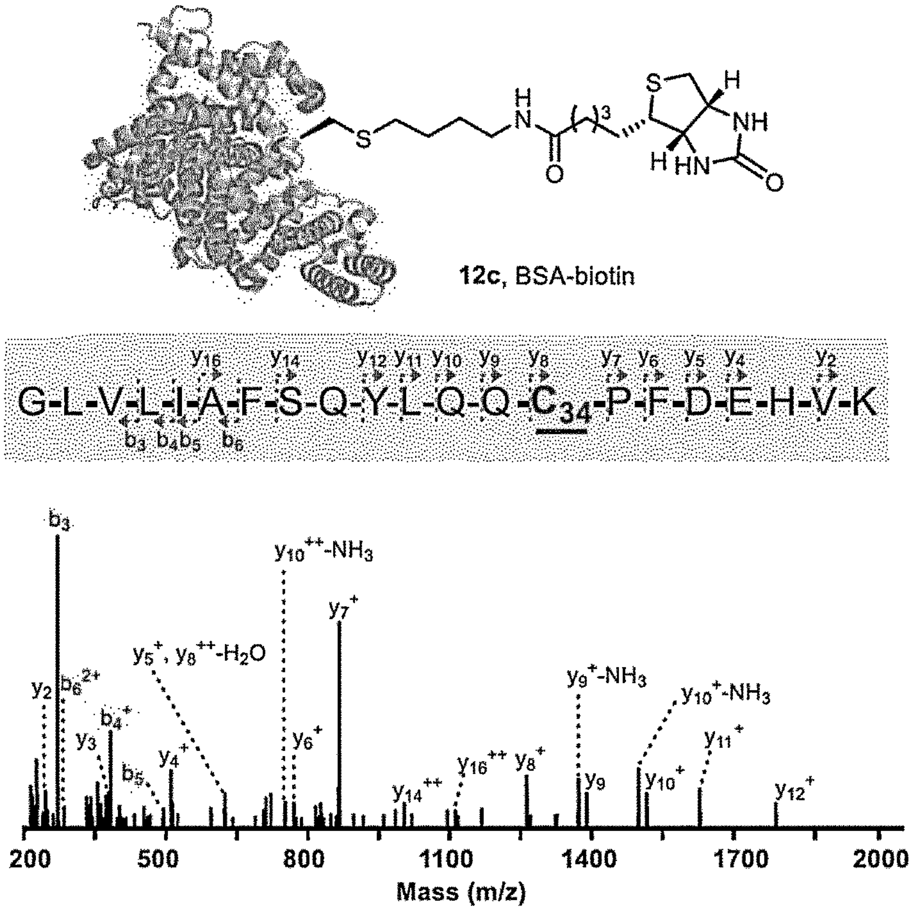
FIG. 7 confirms the results of cysteine-selective conjugation reaction of bovine serum albumin (BSA) and biotin by photocatalysis of $Q_{CAT}$ according to the present disclosure by mass analysis.

As the results are shown in FIGS. 3 and 4, production of a UbK63C-$Q_{peg}$ conjugate and a BSA-$Q_{peg}$ conjugate was confirmed.

While the preferred exemplary embodiment of the present disclosure has been described above, the present disclosure is not limited thereto, and various modification may be carried out within the claims, the description of the disclosure, and the attached drawings, which also belongs to the scope of the present disclosure, of course.

The invention claimed is:

1. A quinolinone derivative compound which selectively binds to cysteine, represented by the following Chemical Formula 1:

[Chemical Formula 1]

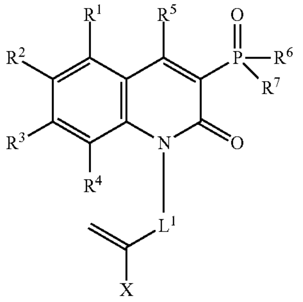

wherein $R^1$ to $R^5$ are independently of one another hydrogen, C1-C20 alkyl, C3-C20 cycloalkyl, C3-C20 heterocycloalkyl, C1-C20 alkoxy, C6-C20 aryl, or C3-C20 heteroaryl;

$R^6$ and $R^7$ are independently of each other hydrogen, C1-C20 alkyl, C1-C20 alkoxy, C6-C20 aryl, or C3-C20 heterocycloalkyl;

$L^1$ is C4-C20 alkylene or C1-C20 oxyalkylene;

X is hydrogen, halogen, C1-C10 alkyl, C1-C7 haloalkyl, C1-C10 alkoxy, C1-C10 haloalkoxyl, or C6-C20 aryl;

the heteroaryl and the heterocycloalkyl independently of each other contain one or more heteroatoms selected from nitrogen, oxygen, and sulfur.

2. The quinolinone derivative compound which selectively binds to cysteine of claim 1, wherein $R^1$ to $R^5$ are independently of one another hydrogen, C1-C7 alkyl, C3-C10 cycloalkyl, C3-C10 heterocycloalkyl, C1-C7 alkoxy, C6-C10 aryl, or C3-C10 heteroaryl;

$R^6$ and $R^7$ are independently of each other hydrogen, C1-C7 alkyl, C1-C7 alkoxy, C6-C10 aryl, or C3-C10 heterocycloalkyl;

$L^1$ is C4-C10 alkylene or C1-C20 oxyalkylene;

X is hydrogen, halogen, C1-C7 alkyl, C1-C7 haloalkyl, C1-C7 alkoxy, C1-C7 haloalkoxy, or C6-C10 aryl;

the heteroaryl and the heterocycloalkyl independently of each other contain one or more heteroatoms selected from nitrogen, oxygen, and sulfur.

3. The quinolinone derivative compound which selectively binds to cysteine of claim 1, wherein $R^1$ to $R^5$ are independently of one another hydrogen, C1-C7 alkyl, C1-C7 alkoxy, C6-C10 aryl, or C3-C10 heteroaryl;

$R^6$ and $R^7$ are independently of each other hydrogen, C1-C7 alkyl, C1-C7 alkoxy, or C6-C10 aryl;

$L^1$ is C4-C10 alkylene or includes 1 to 10-$OCH_2CH_2$-units;

X is hydrogen, halogen, C1-C7 alkyl, C1-C7 haloalkyl, C1-C7 alkoxy, or C1-C7 haloalkoxy;

the heteroaryl contains one or more heteroatoms selected from nitrogen, oxygen, and sulfur.

4. The quinolinone derivative compound which selectively binds to cysteine of claim 1, wherein $R^1$ to $R^5$ are independently of one another hydrogen, C1-C7 alkyl, or C1-C7 alkoxy;

$R^6$ and $R^7$ are independently of each other C1-C7 alkoxy or C6-C10 aryl;

$L^1$ is C4-C10 alkylene or includes 1 to 10-$OCH_2CH_2$-units;

X is hydrogen, halogen, C1-C7 alkyl, or C1-C7 haloalkyl.

5. An amino acid- or peptide conjugate represented by the following Chemical Formula 2:

[Chemical Formula 2]

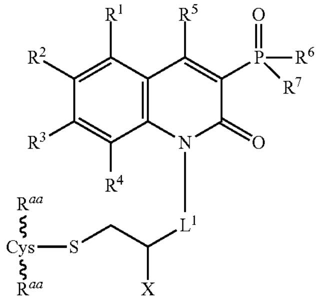

wherein

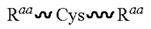

is a single amino acid, oligopeptide, polypeptide, or protein including cysteine residue;

$R^1$ to $R^5$ are independently of one another hydrogen, C1-C20 alkyl, C3-C20 cycloalkyl, C3-C20 heterocycloalkyl, C1-C20 alkoxy, C6-C20 aryl, or C3-C20 heteroaryl;

$R^6$ and $R^7$ are independently of each other hydrogen, C1-C20 alkyl, C1-C20 alkoxy, C6-C20 aryl, or C3-C20 heterocycloalkyl;

$L^1$ is C4-C20 alkylene or C1-C20 oxyalkylene;

X is hydrogen, halogen, C1-C10 alkyl, C1-C7 haloalkyl, C1-C10 alkoxy, C1-C10 haloalkoxyl, or C6-C20 aryl;

the heteroaryl and the heterocycloalkyl independently of each other contain one or more heteroatoms selected from nitrogen, oxygen, and sulfur;

alkyl, cycloalkyl, heterocycloalkyl, alkoxy, aryl, and heteroaryl of $R^1$ to $R^5$ may be further substituted by any one or more selected from the group consisting of —OR', —COR', —NR'R", —NR'COR", —NHCOR', —$NHCOCH_2NR'R"$, and —NR'PO(OR")(OH); and R' and R" are independently of each other any one selected from the group consisting of hydrogen, C1-C7 alkyl, $C_3$-$C_6$ cycloalkyl, $C_3$-$C_6$ alkenyl, and $C_3$-$C_6$ alkynyl.

6. The amino acid- or peptide conjugate of claim 5, wherein

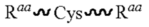

is a single amino acid, oligopeptide, polypeptide, or protein including cysteine residue;

$R^1$ to $R^5$ are independently of one another hydrogen, C1-C7 alkyl, C3-C10 cycloalkyl, C3-C10 heterocycloalkyl, C1-C7 alkoxy, C6-C10 aryl, or C3-C10 heteroaryl;

$R^6$ and $R^7$ are independently of each other hydrogen, C1-C7 alkyl, C1-C7 alkoxy, C6-C10 aryl, or C3-C10 heterocycloalkyl;

$L^1$ is C4-C10 alkylene or C1-C20 oxyalkylene;

X is hydrogen, halogen, C1-C7 alkyl, C1-C7 haloalkyl, C1-C7 alkoxy, C1-C7 haloalkoxy, or C6-C10 aryl;

the heteroaryl and the heterocycloalkyl independently of each other contain one or more heteroatoms selected from nitrogen, oxygen, and sulfur; and alkyl, cycloalkyl, heterocycloalkyl, alkoxy, aryl, and heteroaryl of $R^1$ to $R^5$ may be further substituted by —OH, —OR', —COR', —NR'R", —NR'COR", —NHCOR', —$NHCOCH_2NR'R"$, and —NR'PO(OR")(OH).

7. The amino acid- or peptide conjugate of claim 5, wherein

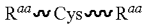

is a single amino acid, oligopeptide, polypeptide, or protein including cysteine residue;

$R^1$ to $R^5$ are independently of one another hydrogen, C1-C7 alkyl, C1-C7 alkoxy, C6-C10 aryl, or C3-C10 heteroaryl;

$R^6$ and $R^7$ are independently of each other hydrogen, C1-C7 alkyl, C1-C7 alkoxy, or C6-C10 aryl;

$L^1$ is C4-C10 alkylene or includes 1 to 10-$OCH_2CH_2$-units;

X is hydrogen, halogen, C1-C7 alkyl, C1-C7 haloalkyl, C1-C7 alkoxy, or C1-C7 haloalkoxy;

the heteroaryl contains one or more heteroatoms selected from nitrogen, oxygen, and sulfur; and alkyl, alkoxy, aryl, and heteroaryl of $R^1$ to $R^5$ may be further substituted by —OH, —OR', —COR', —NR'R", —NR'COR", —NHCOR', —$NHCOCH_2NR'R"$, and —NR'PO(OR")(OH).

8. The amino acid- or peptide conjugate of claim 5, wherein

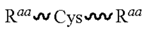

is a single amino acid or protein including cysteine residue;

$R^1$ to $R^5$ are independently of one another hydrogen, C1-C7 alkyl, or C1-C7 alkoxy;

$R^6$ and $R^7$ are independently of each other C1-C7 alkoxy or C6-C10 aryl;

$L^1$ is C4-C10 alkylene or includes 1 to 10-$OCH_2CH_2$-units;

X is hydrogen, halogen, C1-C7 alkyl, or C1-C7 haloalkyl; and alkyl or alkoxy of $R^1$ to $R^5$ may be further substituted by —OH, —OR', —COR', —NR'R", —NR'COR", —NH-COR', —$NHCOCH_2NR'R"$, and —NR'PO(OR")(OH).

9. The amino acid- or peptide conjugate of claim 5, wherein the protein is an antibody, a fragment of an antigenic polypeptide, or an artificial antibody.

10. An amino acid- or peptide conjugate represented by the following Chemical Formula 3 or Chemical Formula 4:

[Chemical Formula 3]

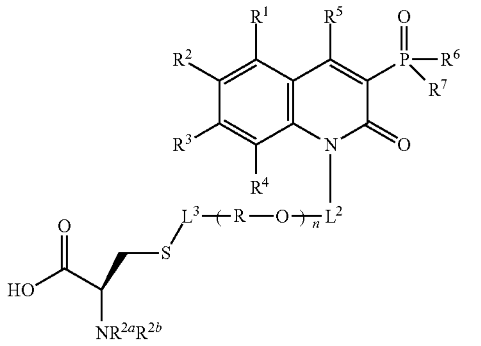

[Chemical Formula 4]

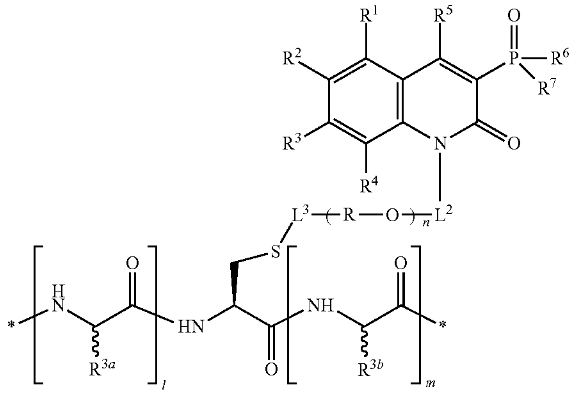

wherein $R^1$ to $R^5$ are independently of one another hydrogen, C1-C20 alkyl, C3-C20 cycloalkyl, C3-C20 heterocycloalkyl, C1-C20 alkoxy, C6-C20 aryl, or C3-C20 heteroaryl;

$R^6$ and $R^7$ are independently of each other hydrogen, C1-C20 alkyl, C1-C20 alkoxy, C6-C20 aryl, or C3-C20 heterocycloalkyl;

$L^2$, $L^3$, and R are $C_1$-$C_5$ alkylene, $L^2$, $L^3$, and R may be further substituted by one or more selected from halogen, C1-C10 alkyl, C1-C10 alkoxy, C1-C10 haloalkoxyl, C6-C20 aryl, and combinations thereof, in Chemical Formula 3, $R^{2a}$ and $R^{2b}$ are independently of each other hydrogen or an acetyl group, in Chemical Formula 4, $R^{3a}$ and $R^{3b}$ are identical or different side chains of amino acid, and n is an integer of 0 to 10, and 1 and m are integers of 0 to 400.

11. An antibody-drug conjugate comprising: the amino acid- or peptide conjugate of claim 5.

12. The antibody-drug conjugate of claim 11, wherein the drug is an immunomodulatory compound, an anticancer compound, an antiviral agent, an antibacterial agent, an antifungal agent, an anthelmintic agent, or a combination thereof.

13. An antibody-drug conjugate comprising: the amino acid- or peptide conjugate of claim 6.

14. An antibody-drug conjugate comprising: the amino acid- or peptide conjugate of claim 7.

15. An antibody-drug conjugate comprising: the amino acid- or peptide conjugate of claim 8.

16. An antibody-drug conjugate comprising: the amino acid- or peptide conjugate of claim 9.

17. An antibody-drug conjugate comprising: the amino acid- or peptide conjugate of claim 10.

* * * * *